US012637711B2

(12) United States Patent
Lindsay et al.

(10) Patent No.: US 12,637,711 B2
(45) Date of Patent: May 26, 2026

(54) DIRECT ELECTRICAL READOUT OF NUCLEIC ACID SEQUENCES

(71) Applicant: ARIZONA BOARD OF REGENTS ON BEHALF OF ARIZONA STATE UNIVERSITY, Scottsdale, AZ (US)

(72) Inventors: Stuart Lindsay, Phoenix, AZ (US); Bintian Zhang, Tempe, AZ (US); Hanqing Deng, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1180 days.

(21) Appl. No.: 17/620,566

(22) PCT Filed: Jun. 19, 2020

(86) PCT No.: PCT/US2020/038740
§ 371 (c)(1),
(2) Date: Dec. 17, 2021

(87) PCT Pub. No.: WO2020/257654
PCT Pub. Date: Dec. 24, 2020

(65) Prior Publication Data
US 2022/0316002 A1 Oct. 6, 2022

Related U.S. Application Data

(60) Provisional application No. 62/864,174, filed on Jun. 20, 2019.

(51) Int. Cl.
*C12Q 1/6869* (2018.01)
*C12Q 1/00* (2006.01)
*G01N 27/447* (2006.01)

(52) U.S. Cl.
CPC ........... *C12Q 1/6869* (2013.01); *C12Q 1/005* (2013.01); *C12Y 207/07007* (2013.01); *G01N 27/44791* (2013.01)

(58) Field of Classification Search
None
See application file for complete search history.

(56) References Cited

U.S. PATENT DOCUMENTS 5,198,543 A 3/1993 Blanco
6,022,688 A 2/2000 Jurinke et al.
(Continued)

FOREIGN PATENT DOCUMENTS

CN 1325490 A 12/2001
CN 1916630 A 2/2007
(Continued)

OTHER PUBLICATIONS

Carter et al., Functional protein materials: beyond elastomeric and structural proteins, Polym. Chem. 2019, 10:2952-2959.
(Continued)

*Primary Examiner* — J. Christopher Ball
(74) *Attorney, Agent, or Firm* — Casimir Jones, S.C.; Peter J. Schlueter

(57) ABSTRACT

Disclosed are devices, systems and methods for direct measurement of polymerase activity. In one example, a device includes at least a first electrode and a second electrode, the first and second electrode being separated by a gap; and a polymerase with two attachment sites, one for attaching to the first electrode and a second for attaching to the second electrode, wherein the two attachment sites are separated by a distance of at least about 1 nm and the distance does not significantly change with conformational changes of the polymerase.

29 Claims, 38 Drawing Sheets

Specification includes a Sequence Listing.

(56) References Cited

U.S. PATENT DOCUMENTS

| | | |
|---|---|---|
| 6,391,558 B1 | 5/2002 | Henkens et al. |
| 6,758,961 B1 | 7/2004 | Vogel et al. |
| 6,824,974 B2 | 11/2004 | Pisharody et al. |
| 7,632,671 B2 | 12/2009 | Tong |
| 7,785,785 B2 | 8/2010 | Pourmand et al. |
| 8,628,649 B2 | 1/2014 | Lindsay et al. |
| 8,753,893 B2 | 6/2014 | Liu et al. |
| 8,961,757 B2 | 2/2015 | Nuckolls et al. |
| 8,968,540 B2 | 3/2015 | Reinhart et al. |
| 9,140,682 B2 | 9/2015 | Lindsay et al. |
| 9,274,430 B2 | 3/2016 | Gyarfas et al. |
| 9,376,713 B2 | 6/2016 | Bashir et al. |
| 9,395,352 B2 | 7/2016 | Lindsay et al. |
| 9,593,372 B2 | 3/2017 | Lindsay et al. |
| 9,766,248 B2 | 9/2017 | Lindsay et al. |
| 9,810,681 B2 | 11/2017 | Lindsay et al. |
| 9,938,586 B2 | 4/2018 | Liang et al. |
| 10,036,064 B2 | 7/2018 | Merriman et al. |
| 10,047,392 B2 | 8/2018 | Ivankin et al. |
| 10,051,722 B2 | 8/2018 | Yamamoto et al. |
| 10,227,694 B2 | 3/2019 | Jin et al. |
| 10,378,103 B2 | 8/2019 | Jin et al. |
| 10,379,102 B2 | 8/2019 | Lindsay et al. |
| 10,422,787 B2 | 9/2019 | Lindsay et al. |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,648,941 B2 | 5/2020 | Merriman et al. |
| 10,712,334 B2 | 7/2020 | Choi et al. |
| 10,737,263 B2 | 8/2020 | Choi et al. |
| 10,913,966 B2 | 2/2021 | Merriman et al. |
| 11,630,098 B2 | 4/2023 | Lindsay et al. |
| 11,808,755 B2 | 11/2023 | Lindsay et al. |
| 11,959,905 B2 | 4/2024 | Lindsay et al. |
| 2003/0064390 A1 | 4/2003 | Schuelein et al. |
| 2003/0098248 A1 | 5/2003 | Vogel et al. |
| 2003/0124572 A1 | 7/2003 | Umek et al. |
| 2004/0146863 A1 | 7/2004 | Pisharody et al. |
| 2004/0249124 A1 | 12/2004 | Caruso et al. |
| 2005/0074871 A1 | 4/2005 | Albert et al. |
| 2005/0266456 A1 | 12/2005 | Williams et al. |
| 2005/0285275 A1 | 12/2005 | Son et al. |
| 2006/0154489 A1 | 7/2006 | Tornow et al. |
| 2008/0218184 A1 | 9/2008 | White et al. |
| 2009/0017571 A1 | 1/2009 | Nuckolls et al. |
| 2009/0215156 A1 | 8/2009 | Chung et al. |
| 2009/0226899 A1 | 9/2009 | Chen |
| 2009/0295372 A1 | 12/2009 | Krstic et al. |
| 2010/0084276 A1 | 4/2010 | Lindsay |
| 2010/0184062 A1 | 7/2010 | Steinmuller-Nethl et al. |
| 2010/0206731 A1 | 8/2010 | Lau et al. |
| 2010/0285514 A1 | 11/2010 | Claussen et al. |
| 2011/0098218 A1 | 4/2011 | Han et al. |
| 2011/0166034 A1 | 7/2011 | Kwong et al. |
| 2011/0312529 A1 | 12/2011 | He et al. |
| 2012/0228386 A1 | 9/2012 | Wu et al. |
| 2012/0231447 A1 | 9/2012 | Zhang et al. |
| 2012/0258870 A1 | 10/2012 | Schwartz et al. |
| 2012/0288948 A1 | 11/2012 | Lindsay et al. |
| 2013/0109577 A1 | 5/2013 | Korlach et al. |
| 2013/0302901 A1 | 11/2013 | Lindsay et al. |
| 2014/0141525 A1 | 5/2014 | Albert et al. |
| 2014/0231274 A1 | 8/2014 | Oki et al. |
| 2015/0010935 A1 | 1/2015 | Lindsay et al. |
| 2015/0017655 A1 | 1/2015 | Huang et al. |
| 2015/0086994 A1 | 3/2015 | Williams et al. |
| 2015/0142327 A1 | 5/2015 | Ashcroft et al. |
| 2015/0144506 A1 | 5/2015 | Lindsay et al. |
| 2015/0285818 A1 | 10/2015 | Banala et al. |
| 2015/0362459 A1 | 12/2015 | Chung et al. |
| 2016/0018384 A1 | 1/2016 | Lindsay et al. |
| 2016/0025702 A1 | 1/2016 | Lindsay et al. |
| 2016/0082739 A1 | 3/2016 | Takagiwa |
| 2016/0083789 A1 | 3/2016 | Turner et al. |
| 2016/0097759 A1 | 4/2016 | Lindsay et al. |
| 2016/0108002 A1 | 4/2016 | Zhang et al. |
| 2016/0146828 A1 | 5/2016 | Lindsay et al. |
| 2016/0177383 A1 | 6/2016 | Ashcroft et al. |
| 2016/0194698 A1 | 7/2016 | Lindsay |
| 2016/0258925 A1 | 9/2016 | Gyarfas et al. |
| 2016/0280723 A1 | 9/2016 | Zhang et al. |
| 2016/0282295 A1 | 9/2016 | Wang et al. |
| 2016/0319343 A1 | 11/2016 | Korlach et al. |
| 2017/0003245 A1 | 1/2017 | Lindsay et al. |
| 2017/0016852 A1 | 1/2017 | Lindsay et al. |
| 2017/0037462 A1 | 2/2017 | Turner et al. |
| 2017/0038333 A1 | 2/2017 | Turner et al. |
| 2017/0038369 A1 | 2/2017 | Lindsay et al. |
| 2017/0044605 A1 | 2/2017 | Merriman et al. |
| 2017/0067902 A1 | 3/2017 | Zhang et al. |
| 2017/0121761 A1 | 5/2017 | Eichen et al. |
| 2017/0137389 A1 | 5/2017 | Zhang et al. |
| 2017/0168039 A1 | 6/2017 | Lindsay et al. |
| 2017/0204066 A1 | 7/2017 | Lindsay et al. |
| 2017/0276678 A1 | 9/2017 | Ervin |
| 2017/0343558 A1 | 11/2017 | Lindsay et al. |
| 2018/0031549 A1 | 2/2018 | Chen et al. |
| 2018/0051332 A9 | 2/2018 | Esfandyarpour et al. |
| 2018/0073071 A1 | 3/2018 | Ju et al. |
| 2018/0095081 A1 | 4/2018 | Albert et al. |
| 2018/0120286 A1 | 5/2018 | Lindsay et al. |
| 2018/0155773 A1 | 6/2018 | Gunderson et al. |
| 2018/0180567 A1 | 6/2018 | Li et al. |
| 2018/0305727 A1 | 10/2018 | Merriman et al. |
| 2018/0340220 A1 | 11/2018 | Merriman et al. |
| 2019/0004003 A1 | 1/2019 | Merriman et al. |
| 2019/0041355 A1 | 2/2019 | Merriman et al. |
| 2019/0094175 A1 | 3/2019 | Merriman et al. |
| 2019/0112643 A1 | 4/2019 | Aran et al. |
| 2019/0234902 A1 | 8/2019 | Lima, Jr. et al. |
| 2019/0309008 A1 | 10/2019 | Ju et al. |
| 2019/0317040 A1 | 10/2019 | Lindsay et al. |
| 2019/0330695 A1 | 10/2019 | Guo et al. |
| 2019/0376135 A1 | 12/2019 | Mandell et al. |
| 2020/0157595 A1 | 5/2020 | Merriman et al. |
| 2021/0114025 A1 | 4/2021 | De Freitas Dias et al. |
| 2021/0208127 A1 | 7/2021 | Lindsay et al. |
| 2021/0269869 A1 | 9/2021 | Lindsay |
| 2021/0325379 A1 | 10/2021 | Lindsay et al. |
| 2021/0340614 A1 | 11/2021 | Lindsay |
| 2021/0372986 A1 | 12/2021 | Lindsay |
| 2022/0098635 A1 | 3/2022 | Lindsay et al. |
| 2022/0196646 A1 | 6/2022 | Lindsay et al. |
| 2022/0252542 A1 | 8/2022 | Merriman et al. |
| 2022/0389502 A1 | 12/2022 | Lindsay et al. |
| 2023/0243807 A1 | 8/2023 | Lindsay et al. |

FOREIGN PATENT DOCUMENTS

| | | | |
|---|---|---|---|
| CN | 101365827 A | | 2/2009 |
| CN | 101400800 A | | 4/2009 |
| CN | 102414560 A | | 4/2012 |
| CN | 104105797 A | | 10/2014 |
| CN | 104359946 | | 2/2015 |
| CN | 105283560 A | | 1/2016 |
| CN | 105378113 A | | 3/2016 |
| CN | 107082792 A | | 8/2017 |
| CN | 107666962 A | | 2/2018 |
| CN | 107683337 A | | 2/2018 |
| CN | 108018270 A | | 5/2018 |
| CN | 109154024 A | | 1/2019 |
| CN | 109891233 A | | 6/2019 |
| EP | 3976814 A1 | | 4/2022 |
| JP | H01248570 A | | 10/1989 |
| JP | H0719927 B2 | | 3/1995 |
| JP | 2012021972 A | | 2/2012 |
| JP | 2016188794 A | | 11/2016 |
| JP | 2018500905 A | | 1/2018 |
| TW | 201409690 A | | 3/2014 |
| WO | WO-2012050533 A1 | | 4/2012 |
| WO | WO 2013/038272 | | 3/2013 |
| WO | WO 2013/154999 | | 10/2013 |
| WO | WO 2014/074727 | | 5/2014 |

(56) References Cited

FOREIGN PATENT DOCUMENTS

| | | |
|---|---|---|
| WO | WO 2015/130781 | 9/2015 |
| WO | WO 2015/131073 | 9/2015 |
| WO | WO 2015/161119 | 10/2015 |
| WO | WO 2015/170784 | 11/2015 |
| WO | WO 2016/100635 A1 | 6/2016 |
| WO | WO 2016/161402 | 10/2016 |
| WO | WO 2016/210386 | 12/2016 |
| WO | WO-2017042038 A1 | 3/2017 |
| WO | WO 2017/084998 | 5/2017 |
| WO | WO 2017/123416 | 7/2017 |
| WO | WO-2017132567 A1 | 8/2017 |
| WO | WO-2017132586 A1 | 8/2017 |
| WO | WO-2017148861 A1 | 9/2017 |
| WO | WO 2017/189930 | 11/2017 |
| WO | WO 2018/026855 | 2/2018 |
| WO | WO-2018098286 A1 | 5/2018 |
| WO | WO 2018/132457 | 7/2018 |
| WO | WO 2018/200687 | 11/2018 |
| WO | WO 2018/208505 | 11/2018 |
| WO | WO 2019/046589 | 3/2019 |
| WO | WO 2019/086305 | 5/2019 |
| WO | WO-2019161381 A1 | 8/2019 |
| WO | WO 2019/211622 | 11/2019 |
| WO | WO 2019/217600 | 11/2019 |
| WO | WO 2019/222527 | 11/2019 |
| WO | WO 2020/160300 | 8/2020 |
| WO | WO-2020160300 A9 | 10/2020 |
| WO | WO 2020/243207 | 12/2020 |
| WO | WO 2020/257654 | 12/2020 |
| WO | WO 2021/163275 | 8/2021 |
| WO | WO 2021/173681 | 9/2021 |
| WO | WO 2021/222791 | 11/2021 |

OTHER PUBLICATIONS

Zhang et al., Electronic Transport in Molecular Wires of Precisely Controlled Length Built from Modular Proteins, ACS Nano 2022, 16(1): 1671-1680.

Anzai et al., "Avidin-biotin complexation for enzyme sensor applications" Trends in Analytical Chemistry, 1994, 13(5): 205-210.

Barhoumi et al., "Urease immobilization on biotinylated polypyrrole coated ChemFEC devices for urea biosensor development" IRBM, Apr. 1, 2008, 29(2-3): 192-201.

Castellarnau et al., "Integrated microanalytical system based on electrochemical detection and cell positioning" Materials Science and Engineering, 2006, 26: 405-410.

Disseration by Joshua Sadar, Top-Down and Bottom-Up Strategies to Prepare Nanogap Sensors for Controlling and Characterizing Single Biomolecules, Jul. 2019, 160 pages.

Hays et al., Development of capacitance based immunosensors on mixed self-assembled monolayers. Sensors and Actuators B: Chemical, Apr. 26, 2006, vol. 114, No. 2, pp. 1064-1070.

Hozel et al., "Trapping Single Molecules by Dielectrophoresis" Physical Review Letters, 2005, 128102-1-4.

Ihalainene et al., "Application of paper-supported printed gold eletrodes for impedimetric immunosensor development" Biosensors 2013, 3:1-17.

Krishnan et al., "Long-Range Conductivity in Proteins Mediated by Aromatic Residues" ACS Phys. Chem Au 2023, 3:444-455.

Lindsay et al., "Recognition tunneling" Nanotechnology 2010, 21:262001, 12 pp.

Maalouf R. et al., Label-Free Detection of Bacteria by Electrochemical Impedance Spectroscopy: Comparison to Surface Plasmon Resonance. Anal. Chem, May 25, 2007, vol. 79, No. 13, pp. 4879-4886.

Ouerghi et al., "Impedimetric immunosensor using avidin-biotin for antibody immobilization" Bioelectrochemistry, May 15, 2002, 56(1-2): 131-133.

Prodromidis et al., "Impedimetric immunosensors—A review Electrochimica Acta, May 30, 2010, 55(14): 4227-4233".

Sela-Culang et al., "The strutural basis of antibody-antigen recognition" Frontiers in Immunology, 2013, vol. 4, 13 pages.

Shimura & Yoshida, "Heterogeneous photocatalytic hydrogen production from water and biomass derivatives" Energy Environmental Science 2011, 4: 2467.

Uygun et al., "CRISPR-dCAS9 powered impedimetric biosensor for label-free detection of circulating tumor DNAs" Analytica Chimica Acta 2020, 1121:35-41.

Varga et al., "Binding of a Mouse Monoclonal IgE (anti-DNP) antibody to radio-derivatized polystyrene-DNP complexes" The FASEB Journal, Federation of American Societies for Experimental Biology, Jun. 1, 1990, 4(9): 2678-2683.

Yoon, "Hidden Markov Models and their Applications in Biological Sequence Analysis" Current Genomics, 2009, 10:402-415.

Arielly R., et al., "Real-Time Detection of Redox Events in Molecular Junctions," Journal of the American Chemical Society, Jan. 27, 2014, vol. 136, No. 6, pp. 2674-2680.

Artes J.M., et al., "Conductance Switching in Single Wired Redox Proteins," Small, Jul. 9, 2014, vol. 10, No. 13, pp. 2537-2541, Published Online: Mar. 13, 2014.

Bayer E.A., et al., "3-(N-Maleimido-Propionyl) Biocytin: A Versatile Thiol-Specific Biotinylating Reagent," Analytical Biochemistry, Academic Press, Amsterdam, NL, Sep. 1, 1985, vol. 149, No. 2, pp. 529-536, DOI: 10.1016/0003-2697(85)90609-8, ISSN: 0003-2697, XP024823414, [Retrieved on Sep. 1, 1985].

Beratan D.N., et al., "Charge Transfer in Dynamical Biosytems, or The Treachery of (Static) Images," Accounts of Chemical Research, Feb. 17, 2015, vol. 48, No. 2, pp. 474-481, (Published on: Oct. 13, 2014).

Bertazzon A., et al., "Scanning Tunneling Microscopy Imaging of Torpedo Acetylcholine Receptor," Proceedings of the National Academy of Sciences, USA, Oct. 15, 1992, vol. 89, No. 20, pp. 9632-9636.

Bogomolny E., et al., "Structure of Wave Functions of Pseudointegrable Billiards," Physical Review Letters, Jun. 18, 2004, vol. 92, No. 24, pp. 244102-1-1244102-4, (Published on: Jun. 16, 2004).

Bogomolny E.B., et al., "Models of Intermediate Spectral Statistics," Physical Review E, Feb. 1, 1999, vol. 59, No. 2, pp. R1315-R1318.

Chang S., et al., "Gap Distance and Interactions in a Molecular Tunnel Junction," Journal of American Chemical Society, 2011, vol. 133, No. 36, pp. 14267-14269, (Published on Aug. 12, 2011).

Chang S., et al., "Palladium Electrodes for Molecular Tunnel Junctions," Nanotechnology, Oct. 4, 2012, vol. 23, No. 42(425202), pp. 1-5, 6 Pages.

Chen X., "Palladium as electrode in DNA sequencing," Applied Physics Letters, Aug. 9, 2013, vol. 103, No. 063306, pp. 1-4 (5 Pages).

Chen Y-S., et al., "A Protein Transistor Made of an Antibody Molecule and Two Gold Nanoparticles," Nature Nanotechnology, Mar. 2012, vol. 7, pp. 197-203 (25 Pages), (Published Online on: Feb. 26, 2012).

Co-Pending U.S. Appl. No. 62/184,776, filed Jun. 25, 2015, 24 Pages.

Cui X., et al., "Layer-by-layer 1 Assembly of Multilayer Filme Composed of Avidin and Biotin-labeled Antibody for Immunosensing," Biosensors and Bioelectronics, Jan. 1, 2003, vol. 18, No. 1, pp. 59-67.

Dong X., et al., "(Alphav)(Beta3) Integrin Crystal Structures and Their Functional Implications," Biochemistry, Oct. 29, 2012, vol. 51, No. 44, pp. 8814-8828.

Engel G.S., et al., "Evidence for Wavelike Energy Transfer Through Quantum Coherence in Photosynthetic Systems," Nature, Apr. 12, 2007, vol. 446, No. 7137, pp. 782-786.

Extended European Search Report for European Application No. 20827063.7, mailed Jun. 19, 2023, 10 Pages.

Fan F-R.F., et al., "Electrochemical Detection of Single Molecules," Science, Feb. 10, 1995, vol. 267, No. 5199, pp. 871-874 (5 Pages).

Gerrits M., et al., "Cell-Free Synthesis of Defined Protein Conjugates by Site directed Cotranslational Labeling," NCBI Bookshelf, Madame Curie Bioscience Database [Internet]. Austin (TX) Landes Bioscience; 2000-2013, Jan. 1, 2013, 12 Pages, Retrieved from URL:https://ww.ncbi.nlm.nih.gov/books/NBK 6497.

(56) References Cited

OTHER PUBLICATIONS

Grden M., et al., "Electrochemical Behaviour of Palladium Electrode: Oxidation, Electrodissolution and Ionic Adsorption," Electrochimica Acta, Nov. 1, 2008, vol. 53, No. 26, pp. 7583-7806, 16 Pages.

Haiss W., et al., "Thermal Gating of the Single Molecule Conductance of Alkanedithiols," Faraday Discussions, 2006, vol. 131, pp. 253-264, (Published on Oct. 4, 2005).

Hoffman R., et al., "An Extended Huckel Theory I. Hydrocarbons," The Journal of Chemical Physics, Sep. 15, 1963, vol. 39, No. 6, pp. 1397-1412 (17 Pages).

Im J.O., et al., "Electronic Single-molecule Identification of Carbohydrate Isomers by Recognition Tunnelling," Nature Communications, Dec. 21, 2016, vol. 7, Article 13868, pp. 1-7.

Karachaliou C-E., et al., "IgY Technology: Methods for Developing and Evaluating Avian Immunoglobulins for the in Vitro Detection of Biomolecules," World Journal of Methodology, Sep. 20, 2021, vol. 11, No. 5, pp. 243-262 (24 Pages).

Kumar K.S., et al., "Long-range Tunneling Processes Across Ferritin-based Junctions," Advanced Materials, Mar. 2, 2016, vol. 28, No. 9, pp. 1824-1830, (Dec. 28, 2015).

Leatherbarrow R.J., et al., "Structure of Immunoglobulin G by Scanning Tunnelling Microscopy," Journal of Molecular Biology, Sep. 20, 1991, vol. 221, No. 2, pp. 361-365.

Lloyd S., "Quantum Coherence in Biological Systems," Journal of Physics: Conference Series, 2011, vol. 302, No. 012037, pp. 1-5 (6 Pages).

Lucie S., et al., "Clustering and Internalization of Integrin (Alphav)(Beta3) With a Tetrameric RGD-synthetic Peptide," Molecular Therapy, May 2009, vol. 17, No. 5, pp. 837-843, (Published Online on Mar. 3, 2009).

Luo B-H., et al., "Structural Basis of Integrin Regulation and Signaling," Annual Review of Immunology, 2007, vol. 25, pp. 619-647 (32 Pages), (Jan. 2, 2007).

Miodek A., et al., "Streptavidin-Polypyrrole Film as Platform for Biotinylated Redox Probe Immobilization for Electrochemical Immunosensor Application," Electroanalysis, 2016, vol. 28, No. 8, pp. 1824-1832, (Published Online on May 27, 2016).

Nature: "Protein Structure" Nature Education at the Scitable by Nature Education, 2014, 4 Pages, [Retrieved on Oct. 15, 2024] Retrieved from URL: https://www.nature.com/scitable/topicpage/protein-structure-14122136/.

Non-Final Office Action for U.S. Appl. No. 15/375,901, mailed Dec. 10, 2018, 30 Pages.

Notice of Allowance for U.S. Appl. No. 15/375,901, mailed Mar. 29, 2019, 11 Pages.

O'Boyle N.M., et al., "Open Babel: An Open Chemical Toolbox," Journal of Cheminformatics, Oct. 7, 2011, vol. 3, No. 33, pp. 1-14.

Onuchic J.N., et al., "Pathway Analysis of Protein Electron-Transfer Reactions," Annual Review of Biophysics and Biomolecular Structure, 1992, vol. 21, pp. 349-377 (31 Pages).

Palecek E., et al., "Electrochemistry of Nonconjugated Proteins and Glycoproteins. Toward Sensors for Biomedicine and Glycomics," Chemical Reviews, 2015, vol. 115, No. 5, pp. 2045-2108, (Published on Feb. 9, 2015).

Pang P., et al., "Fixed-gap Tunnel Junction for Reading DNA Nucleotides," ACS Nano, Nov. 7, 2014, vol. 8, No. 12, pp. 11994-12003 (20 Pages), (Including Supporting Material).

Partial European Search Report for European Application No. 23188136.8, mailed Nov. 30, 2023, 18 Pages.

Partial Supplementary European Search Report for European Application No. 20749683.7, mailed Oct. 7, 2022, 20 Pages.

Polizzi N.F., et al., "Physical Constraints on Charge Transport Through Bacterial Nanowires," Faraday Discussions, 2012, vol. 155, pp. 43-62, (Published on Oct. 17, 2011).

Roxin A., et al., "Flexible or Fixed: A Comparative Review of Linear and Cyclic Cancer-Targeting Peptides," Future Medicinal Chemistry, Aug. 2012, vol. 4, No. 12, pp. 1601-1618.

Simmons J.G., "Generalized Formula for the Electric Tunnel Effect Between Similar Electrodes Separated by a Thin Insulating Film," Journal of Applied Physics, Jun. 1963, vol. 34, No. 6, pp. 1793-1803 (12 Pages).

Stuchebrukhov A.A., "Toward AB Initio Theory of Long-Distance Electron Tunneling in Proteins: Tunneling Currents Approach," Advances in Chemical Physics, Jan. 1, 2001, vol. 118, pp. 1-44.

Thomson N.H., et al., "Molecular Images of Cereal Proteins by STM," Ultramicroscopy, Jul. 1992, vol. 42-44, (Part B), pp. 1204-1213.

Xiong J-P., et al., "Crystal Structure of the Extracellular Segment of Integrin (Alpha)v(Beta)3 in Complex With an Arg-gly-asp Ligand," Science, Apr. 5, 2002, vol. 296, No. 5565, pp. 151-155 (6 Pages), (Published Online on Mar. 7, 2002).

Zhang B., et al., "Observation of Giant Conductance Fluctuations in a Protein," Nano Futures, 2017, vol. 1, pp. 1-15.

Zhang Y., et al., "Biological Charge Transfer via Flickering Resonance," Proceedings of the National Academy of Sciences, USA, Jul. 15, 2014, vol. 111, No. 28, pp. 10049-10054, (Published Online: Jun. 25, 2014).

Ackerman et al., Massively multiplexed nucleic acid detection with Cas13. Nature. Jun. 2020;582(7811):277-282.

Adhikari et al., Conductivity of individual Geobacter pili. RSC Advances, 2016. 6: p. 8354-8357.

Alloway et al., Interface Dipoles Arising from Self-Assembled Monolayers on Gold: UV-Photoemission Studies of Alkanethiols and Partially Fluorinated Alkanethiols. J. Phys. Chem. B 2003, 107:11690-11699.

Altschul et al., Basic local alignment search tool. J Mol Biol. Oct. 5, 1990;215(3):403-10.

Altschul et al., Gapped BLAST and PSI-BLAST: a new generation of protein database search programs. Nucleic Acids Res. Sep. 1, 1997;25(17):3389-402.

Amdursky et al., Electronic transport via proteins. Adv Mater. Nov. 12, 2014;26(42):7142-61.

Amdursky et al., Solid-state electron transport via cytochrome c depends on electronic coupling to electrodes and across the protein. PNAS, Apr. 15, 2014, vol. 111, No. 15, pp. 5556-5561.

Artes et al., Transistor-like Behavior of Single Metalloprotein Junctions. Nano Lett.,2012, 12(6), pp. 2679-2684 (publication date (Web): Oct. 5, 2011).

Aubert et al., Intraprotein radical transfer during photoactivation of DNA photolyase. Nature. Jun. 1, 2000;405(6786):586-90.

Ausubel et al. Current Protocols in Molecular Biology, John Wiley & Sons, New York, 1998.

Bostick et al., Protein bioelectronics: a review of what we do and do not know. Rep Prog Phys. Feb. 2018;81(2):026601. 58 pages.

Chang et al., Chemical recognition and binding kinetics in a functionalized tunnel junction. Nanotechnology. Jun. 15, 2012;23(23):235101. 28 pages.

Chen, Y.-S., et al., "DNA sequencing using electrical conductance measurements of a DNA polymerase," Nature Nanotechnology, May 5, 2013, pp. 1-7; https://doi.org/10.1038/nnano.2013.71.

Chichil et al., Linkers in the structural biology of protein-protein interactions. Protein Sci. Feb. 2013;22(2):153-67.

Chin et al., Addition of p-Azido-I-phenylalanine to the Genetic Code of *Escherichia coli*. J. Am. Chem. Soc. 2002. 124,31, 9026-9027.

Choi et al. "Site-specific inhibition of integrin alpha v beta 3-vitronectin association by a serasp-val sequence through an Arg-Gly-Asp-binding site of the integrin." Proteomics, vol. 10, Issue 1, No. Jan. 1, 2010, pp. 72-80 (First published Oct. 30, 2009).

Choi et al., "Single-Molecule Lysozyme Dynamics Monitored by an Electronic Circuit," Science (2012) 335:319-324; DOI: 10.1126/science.1214824.

Cui et al., Reproducible measurement of single-molecule conductivity. Science. Oct. 19, 2001;294(5542):571-4.

Dellafiore et al., Modified Nucleoside Triphosphates for In-vitro Selection Techniques. Front Chem. May 4, 2016;4:18.

Duffy et al., Modified nucleic acids: replication, evolution, and next-generation therapeutics. BMC Biology, Sep. 2, 2020. 18:112. 14 pages.

(56)　　　　　References Cited

OTHER PUBLICATIONS

Extended European Search Report for PCT/US2019031394. Mailed Jan. 5, 2022. 7 pages.

Fairhead et al., Plug-and-play pairing via defined divalent streptavidins. J Mol Biol. Jan. 9, 2014;426(1):199-214.

Fujino et al., Chimeric RNA Oligonucleotides Incorporating Triazole-Linked Trinucleotides: Synthesis and Function as mRNA in Cell-Free Translation Reactions. J Org Chem. Oct. 7, 2016;81(19):8967-8976.

Fulton et al., Purification of monoclonal antibody against Ebola GP1 protein expressed in Nicotiana benthamiana. J Chromatogr A. Apr. 10, 2015;1389:128-32.

Garg et al., Interface Electrostatics Dictates the Electron Transport via Bioelectronic Junctions. ACS Appl Mater Interfaces. Dec. 5, 2018;10(48):41599-41607.

Giese et al., Direct observation of hole transfer through DNA by hopping between adenine bases and by tunnelling. Nature. Jul. 19, 2001;412(6844):318-20.

Giese et al., Long distance charge transport through DNA: quantification and extension of the hopping model. Chemphyschem. Dec. 15, 2000;1(4):195-8.

Gonnet et al., Exhaustive matching of the entire protein sequence database. Science. Jun. 5, 1992;256(5062):1443-5.

Guo et al., Tuning electronic transport via hepta-alanine peptides junction by tryptophan doping. Proc Natl Acad Sci U S A. Sep. 27, 2016;113(39):10785-90.

Hajian et al., Detection of unamplified target genes via CRISPR-Cas9 immobilized on a graphene field-effect transistor. Nat Biomed Eng. Jun. 2019;3(6):427-437.

Harriman. Further comments on the redox potentials of tryptophan and tyrosine. Journal of Physical Chemistry 1987. 91:6102-6104.

Hohl et al. Engineering a Polyspecific Pyrrolysyl-tRNA Synthetase by a High Throughput FACS Screen. Sci Rep. Aug. 19, 2019;9(1):11971.

International Search Report and Written Opinion for PCT/US19/31394. Mailed Sep. 10, 2019. 11 pages.

International Search Report and Written Opinion for PCT/US20/15931. Mailed Jul. 27, 2020. 17 pages.

International Search Report and Written Opinion for PCT/US20/38740. Mailed Oct. 2, 2020. 14 pages.

International Search Report and Written Opinion for PCT/US21/17583. Mailed May 3, 2021. 9 pages.

International Search Report and Written Opinion for PCT/US21/19428. Mailed May 6, 2021. 25 pages.

International Search Report and Written Opinion for PCT/US21/27650. Mailed Aug. 25, 2021. 9 pages.

International Search Report and Written Opinion for PCT/US21/30239. Mailed Sep. 27, 2021. 10 pages.

International Search Report and Written Opinion for PCT/US21/34698. Mailed Sep. 30, 2021. 10 pages.

International Search Report and Written Opinion for PCT/US21/63851. Mailed Feb. 17, 2022. 9 pages.

International Search Report and Written Opinion for PCT/US21/64501. Mailed Mar. 17, 2022. 9 pages.

Jeffrey, An Introduction to Hydrogen Bonding. Oxford University Press New York. 1997. TOC only. 6 pages.

Kluenker et al., Monitoring Thiol-Ligand exchange on Au nanoparticle surfaces. Langmuir. Jan. 30, 2018;34(4):1700-1710.

Kotlowski Fine discrimination of volatile compounds by graphene-immobilized odorant-binding proteins, Sensors and Actuatores B: Chemical 2018 (256): 564-72.

Kyte et al., A simple method for displaying the hydropathic character of a protein. J Mol Biol. May 5, 1982;157(1):105-32.

Lagunas et al., Long distance electron transfer through the aqueous solution between redox partner proteins. Nat Commun. Dec. 4, 2018;9(1):5157.

Lai et al., Monoclonal antibody produced in plants efficiently treats West Nile virus infection in mice. Proc Natl Acad Sci U S A. Feb. 9, 2010;107(6):2419-24.

Lai et al., Robust production of virus-like particles and monoclonal antibodies with geminiviral replicon vectors in lettuce. Plant Biotechnol J. Jan. 2012;10(1):95-104.

Leary et al., Unambiguous one-molecule conductance measurements under ambient conditions. Nano Lett. Jun. 8, 2011;11(6):2236-41.

Li et al., CRISPR-SE: a brute force search engine for CRISPR design. NAR Genom Bioinform. Feb. 23, 2021;3(1):lqab013.

Li et al., Synthesis and Photovoltaic effect on electron-withdrawing units for low band gap conjugated polymers bearing bi(thienylenevinylene) side chains. Polymers. 2019, vol. 11 iss 9 pp. 1-13.

Lindsay. Ubiquitous Electron Transport in Non-Electron Transfer Proteins. Life (Basel). May 20, 2020;10(5):72. 13 pages.

Liu et al., Vertical T cellimmunodomincance and epitope entropy determine HIV-1 escape. J Clin Invest. Jan. 2013;123(1):380-93.

Main et al., Design of stable alpha-helical arrays from an idealized TPR motif. Structure. May 2003;11(5):497-508.

Malvankar et al., Tunable metallic-like conductivity in microbial nanowire networks. Nat Nanotechnol. Aug. 7, 2011;6(9):573-9.

Marakova et al., An updated evolutionary classification of CRISPR-Cas systems. Nat Rev Microbiol. Nov. 2015;13(11):722-36.

McKenzie et al., Recent progress in non-native nucleic acid modifications. Chem Soc Rev. Apr. 26, 2021;50(8):5126-5164.

Mejias et al., Controlled nanometric fibers of self-assembled designed protein scaffolds. Nanoscale. Oct. 7, 2014;6(19):10982-8.

Metsky et al., Diagnostic design with machine learning model-based optimization. bioRxiv 2020.11.28.401877: 95 pages.

Mullegama et al., Nucleic Acid Extraction from Human Biological Samples. Methods Mol Biol 2019;1897:359-383.

Nitzan. Chemical dynamics in condensed phases. Oxford University Press., Oxford. 2006. TOC only. 13 pages.

Odella et al., Controlling Proton-Coupled Electron Transfer in Bioinspired Artificial Photosynthetic Relays. J Am Chem Soc. Nov. 14, 2018;140(45):15450-15460.

Olsen et al., "Electronic Measurements of Single-Molecule Processing by DNA Polymerase I (Klenow Fragment)," Journal of the American Chemical Society (Apr. 30, 2013); pp. 1-12; DOI: 10.1021/ja311603r.

Pang et al. "Fixed-Gap Tunnel Junction for Reading DNA Nucleotides" ACS Nano, 2014, 8(12), pp. 11994-12003 (Publication Date (Web): Nov. 7, 2014).

Pearson. Using the FASTA program to search protein and DNA sequence databases. Methods Mol Biol. 1994;24:307-31.

Quast et al., Cotranslational incorporation of non-standard amino acids using cell-free protein synthesis. FEBS Lett. Jul. 8, 2015;589(15):1703-12.

Ruiz et al., Bioengineering a Single-Protein Junction. J Am Chem Soc. Nov. 1, 2017;139(43):15337-15346.

Sambrook et al., Molecular Cloning: A Laboratory Manual, 3d ed., Cold Spring Harbor Press, 2001. TOC only. 23 pages.

Sano et al., Cooperative biotin binding by streptavidin. Electrophoretic behavior and subunit association of streptavidin in the presence of 6 M urea. J Biol Chem. Feb. 25, 1990;265(6):3369-73.

Seifert, Characterization of Streptavidin Binding to Biotinylated, Binary Self-Assembled Thio Monolayers-Influence of Component Ratio and Solvent, Langmuir, 2010, 26(9): 6386-93.

Sek et al., Conductance of alpha-helical peptides trapped within molecular junctions. J Phys Chem B. Oct. 5, 2006;110(39):19671-7.

Sequences of amino acids as found on the world wide web at bmrb.wisc.edu/referenc/choufas. 4 pages.

Smith. The hydrophilic nature of a clean gold surface. J. Colloid Interface Science 1980. 75:51-55.

Staals et al., RNA targeting by the type III-A CRISPR-Cas Csm complex of Thermus thermophilus. Mol Cell. Nov. 20, 2014;56(4):518-30.

Tripkovic et al., Standard hydrogen electrode and potential of zero charge in density functional calculations. Phys. Rev. B 2011. 84:115452.

Tuchband et al., Insulated gold scanning tunneling microscopy probes for recognition tunneling in an aqueous environment. Rev Sci Instrum. Jan. 2012;83(1):015102.

(56)     References Cited

OTHER PUBLICATIONS

Vaish et al., A novel, modification-dependent ATP-binding aptamer selected from an RNA library incorporating a cationic functionality. Biochemistry. Jul. 29, 2003;42(29):8842-51.

Vattay et al., Quantum Criticality at the Origin of Life. Journal of Physics: Conference Series 2015. 626: p. 012023. 11 pages.

Willner et al., Mediated electron transfer in glutathione reductase organized in self-assembled monolayers on Au electrodes. J. Am. Chem. Soc., 1992. 114: p. 10965-10966.

Xiao et al., Conductance titration of single-peptide molecules. J Am Chem Soc. May 5, 2004;126(17):5370-1.

Yang et al., Plant-produced Zika virus envelope protein elicits neutralizing immune responses that correlate with protective immunity against Zika virus in mice. Plant Biotechnol J. Feb. 2018;16(2):572-580.

Zhang et al., Engineering an Enzyme for Direct Electrical Monitoring of Activity. ACS Nano. Feb. 25, 2020;14(2):1360-1368.

Zhang et al., Electronic Conductance Resonance in Non-Redox-Active Proteins. J Am Chem Soc. Apr. 1, 2020;142(13):6432-6438.

Zhang et al., Electronic Decay Length in a Protein Molecule. Nano Lett. Jun. 12, 2019;19(6):4017-4022.

Zhang et al., Observation of Giant Conductance Fluctuations in a Protein. Nano Futures. 2017;1(3):035002. 25 pages.

Zhang et al., Role of contacts in long-range protein conductance. Proc Natl Acad Sci U S A. Mar. 26, 2019;116(13):5886-5891.

Zwolak et al. "Electronic Signature of DNA Nucleotides via Transverse Transport" NanoLett., 2005, 5(3), pp. 421-424 (Publication Date (Web): Feb. 12, 2005).

Kang Y., et al., "DC-Dielectrophoretic Separation of Biological Cells by Size", Biomedical Microdevices, vol. 10, pp. 243-249, 2008, pp. 243-249.

Shang L., et al., "Electrical Characterization of Nanowire Bridges Incorporating Biomolecular Recognition Elements", Nanotechnology, vol. 16, 2005, pp. 2846-2851.

Zhang B., et al., "Engineering an Enzyme for Direct Electrical Monitoring of Activity", ACS NANO, vol. 14, No. 2, Oct. 2019, 1360-1368, 14 Pages, XP055736319, US ISSN: 1936-0851, DOI: 10.1021/acsnano.9b06875.

Cecchetelli A., "Methods for Biotinylating Your Macromolecule of Interest", Plasmids 101: Biotinylation, Nov. 15, 2018, pp. 1-12.

Fig. 1Aii

Fig. 1Aiii

N Contact 1

N Contact 1     Contact 2

N Contact 2     Contact 2

5nm 6.5nm

N Contact 1:MGSSHHHHHHSSGLVPRGSGLNDIFEAQKIEWHEGASS    SEQ ID NO: 1
N Contact 2:MGSSHHHHHHSSGLVPRGSGLNDIFEAQKIEWHEGASSGNSTNGTSNGSS  SEQ ID NO: 2
Contact 2:   (E279)SSGLNDIFEAQKIEWHEGASS(D280)    SEQ ID NO: 3

5'CCCCCCCCCC AACTGGCCG TCGTTTTACA TATGTAAAC GACGGCCAGT T3'  SEQ ID NO: 6

ACATTTTGCTGCCGGTCAGCCCCCCCCCC 5'  SEQ ID NO: 7

ATGTAAACGACGGCCAGTT  SEQ ID NO: 8

5'AAAAAAAAAA AACTGGCCG TCGTTTTACA TATGTAAAC GACGGCCAGT T3'  SEQ ID NO: 9

ACATTTTGCTGCCGGTCAGAAAAAAAAAA 5'  SEQ ID NO: 10

ATGTAAACGACGGCCAGTT  SEQ ID NO: 8

5'CCCCCCCCCC AAAAAAAAAA AACTGGCCG TCGTTTTACA TATGTAAAC GACGGCCAGT T3'  SEQ ID NO: 11

ACATTTTGCTGCCGGTCAAAAAAAAAACCCCCCCCCC 5'  SEQ ID NO: 12

ATGTAAACGACGGCCAGTT  SEQ ID NO: 8

5'ATC ATC ATC ATC AACTGGCCG TCGTTTTACA TATGTAAAC GACGGCCAGT T3'  SEQ ID NO: 13

ACATTTTGCTGCCGGTCAGCTAGTAGTACTA 5'  SEQ ID NO: 14

ATGTAAACGACGGCCAGTT  SEQ ID NO: 8

Fig. 2

```
TACATTTGCTGCCGGTCAATGGCAT TAC (TAC)₉ TAAGGGGCATCATC 5'   SEQ ID NO: 15
                          |||||||
                          |||||||
                          |||||||
                          |||||||
                          |||||||
ATGTAAACGACGACGGCCAGTTACCGTA---(ATG)₉ATTCCGCGTAGTAG  3'
```

(Bold font is a primer, the primers only containing ATG of 9, 8 and 7 which would make the nick sizes of 3bp, 6bp and 9bp, respectively.) These are the sequences of three primers:

CAT-tail primers:

5'- ATGATGATGATGATGATGATGATGATGATTCCGCGTAGTAG  -3'  (ATG)₉   SEQ ID NO: 16

5'- ATGATGATGATGATGATGATGATGCTTACCGCGTAGTAG  -3'  (ATG)₈   SEQ ID NO: 17

5'- ATGATGATGATGATGATGATGCTTCCGAGTAGTAG  -3'  (ATG)₇   SEQ ID NO: 18

Fig. 4

SEQ ID NO: 19

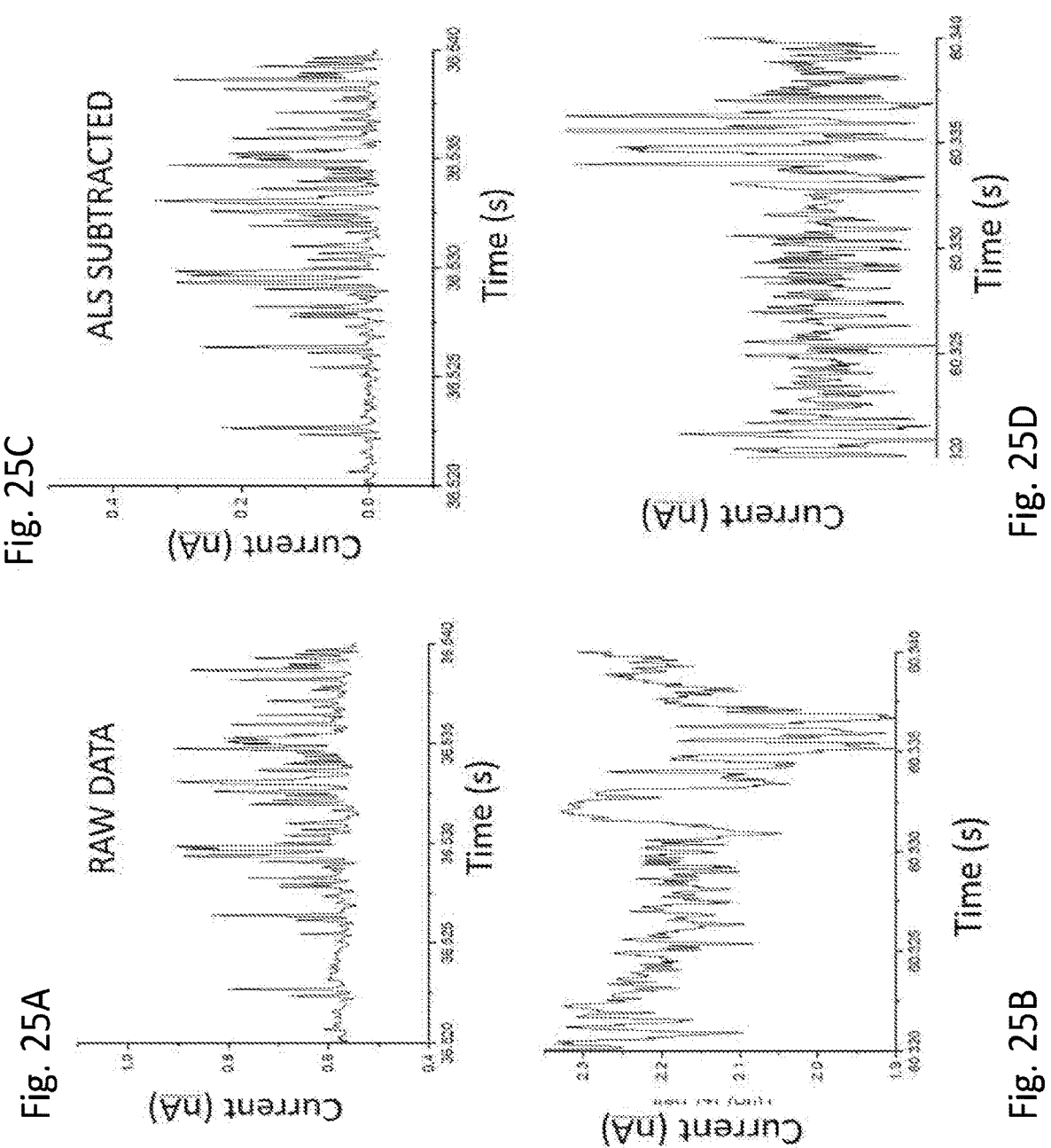

SEQUENCE LISTING

```
<160> NUMBER OF SEQ ID NOS: 22

<210> SEQ ID NO 1
<211> LENGTH: 38
<212> TYPE: PRT
<213> ORGANISM: Artificial Sequence
<220> FEATURE:
<223> OTHER INFORMATION: synthetic amino acid sequence

<400> SEQUENCE: 1

Met Gly Ser Ser His His His His His His Ser Ser Gly Leu Val Pro
1               5                   10                  15

Arg Gly Ser Gly Leu Asn Asp Ile Phe Glu Ala Gln Lys Ile Glu Trp
            20                  25                  30

His Glu Gly Ala Ser Ser
            35
```

```
<210> SEQ ID NO 2
<211> LENGTH: 50
<212> TYPE: PRT
<213> ORGANISM: Artificial Sequence
<220> FEATURE:
<223> OTHER INFORMATION: synthetic amino acid sequence

<400> SEQUENCE: 2

Met Gly Ser Ser His His His His His His Ser Ser Gly Leu Val Pro
1               5                   10                  15

Arg Gly Ser Gly Leu Asn Asp Ile Phe Glu Ala Gln Lys Ile Glu Trp
            20                  25                  30

His Glu Gly Ala Ser Ser Gly Asn Ser Thr Asn Gly Thr Ser Asn Gly
        35                  40                  45

Ser Ser
    50

<210> SEQ ID NO 3
<211> LENGTH: 21
<212> TYPE: PRT
<213> ORGANISM: Artificial Sequence
<220> FEATURE:
<223> OTHER INFORMATION: synthetic amino acid sequence

<400> SEQUENCE: 3

Ser Ser Gly Leu Asn Asp Ile Phe Glu Ala Gln Lys Ile Glu Trp His
1               5                   10                  15

Glu Gly Ala Ser Ser
            20

<210> SEQ ID NO 4
<211> LENGTH: 42
<212> TYPE: DNA
<213> ORGANISM: Artificial Sequence
<220> FEATURE:
<223> OTHER INFORMATION: synthetic oligonucleotide rolling circle
      template

<400> SEQUENCE: 4
ccgtacgatt cgtatctact atcgttcgat tcgcatcatc ta                    42

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotide primer

<400> SEQUENCE: 5
ggcatgctaa gcatagatga t                                            21

<210> SEQ ID NO 6
<211> LENGTH: 48
<212> TYPE: DNA
<213> ORGANISM: Artificial Sequence
<220> FEATURE:
<223> OTHER INFORMATION: synthetic DNA sequence

<400> SEQUENCE: 6
cccccccccc aactggccgt cgttttacat atgtaaacga cggccagt              48

<210> SEQ ID NO 7
<211> LENGTH: 30
<212> TYPE: DNA
<213> ORGANISM: Artificial Sequence
```

-continued

```
<220> FEATURE:
<223> OTHER INFORMATION: synthetic DNA sequence

<400> SEQUENCE: 7
acattttgct gcccggtcaa cccccccccc                                           30

<210> SEQ ID NO 8
<211> LENGTH: 19
<212> TYPE: DNA
<213> ORGANISM: Artificial Sequence
<220> FEATURE:
<223> OTHER INFORMATION: synthetic DNA sequence

<400> SEQUENCE: 8
atgtaaacga cggccagtt                                                       19

<210> SEQ ID NO 9
<211> LENGTH: 48
<212> TYPE: DNA
<213> ORGANISM: Artificial Sequence
<220> FEATURE:
<223> OTHER INFORMATION: synthetic DNA sequence

<400> SEQUENCE: 9
aaaaaaaaaa aactggccgt cgttttacat atgtaaacga cggccagt                       48

<210> SEQ ID NO 10
<211> LENGTH: 29
<212> TYPE: DNA
<213> ORGANISM: Artificial Sequence
<220> FEATURE:
<223> OTHER INFORMATION: synthetic DNA sequence

<400> SEQUENCE: 10
acattttgct gccggtcaaa aaaaaaaaa                                            29

<210> SEQ ID NO 11
<211> LENGTH: 59
<212> TYPE: DNA
<213> ORGANISM: Artificial Sequence
<220> FEATURE:
<223> OTHER INFORMATION: synthetic DNA sequence

<400> SEQUENCE: 11
cccccccccc aaaaaaaaaa aactggccgt cgttttacat atgtaaacga cggccacgt           59

<210> SEQ ID NO 12
<211> LENGTH: 39
<212> TYPE: DNA
<213> ORGANISM: Artificial Sequence
<220> FEATURE:
<223> OTHER INFORMATION: synthetic DNA sequence

<400> SEQUENCE: 12
acattttgct gccggtcaaa aaaaaaaaac ccccccccc                                 39

<210> SEQ ID NO 13
<211> LENGTH: 53
<212> TYPE: DNA
<213> ORGANISM: Artificial Sequence
<220> FEATURE:
<223> OTHER INFORMATION: synthetic DNA sequence

<400> SEQUENCE: 13
atcatcatca tcatcaactg gccgtcgttt tacatatgta aacgacggcc agt                 53
```

```
<210> SEQ ID NO 14
<211> LENGTH: 34
<212> TYPE: DNA
<213> ORGANISM: Artificial Sequence
<220> FEATURE:
<223> OTHER INFORMATION: synthetic DNA sequence

<400> SEQUENCE: 14
acattttgct gccggtcaac tactactact acta                                34

<210> SEQ ID NO 15
<211> LENGTH: 45
<212> TYPE: DNA
<213> ORGANISM: Artificial Sequence
<220> FEATURE:
<223> OTHER INFORMATION: synthetic DNA sequence

<400> SEQUENCE: 15
tacatttgct gccggtcaat ggcattacta ctaaggcgca tcatc                    45

<210> SEQ ID NO 16
<211> LENGTH: 44
<212> TYPE: DNA
<213> ORGANISM: Artificial Sequence
<220> FEATURE:
<223> OTHER INFORMATION: synthetic DNA sequence

<400> SEQUENCE: 16
atgatgatga tgatgatgat gatgatgatt ccgcgtagta gtag                     44

<210> SEQ ID NO 17
<211> LENGTH: 38
<212> TYPE: DNA
<213> ORGANISM: Artificial Sequence
<220> FEATURE:
<223> OTHER INFORMATION: synthetic DNA sequence

<400> SEQUENCE: 17
atgatgatga tgatgatgat gatgcttacg cgtagtag                            38

<210> SEQ ID NO 18
<211> LENGTH: 35
<212> TYPE: DNA
<213> ORGANISM: Artificial Sequence
<220> FEATURE:
<223> OTHER INFORMATION: synthetic DNA sequence

<400> SEQUENCE: 18
atgatgatga tgatgatgat gcttccgagt agtag                               35

<210> SEQ ID NO 19
<211> LENGTH: 49
<212> TYPE: RNA
<213> ORGANISM: Artificial Sequence
<220> FEATURE:
<223> OTHER INFORMATION: synthetic RNA sequence

<400> SEQUENCE: 19
ggcggaauca ucucacucua caucauggcc ggccggguaa ucggccggc                49

<210> SEQ ID NO 20
<211> LENGTH: 16
<212> TYPE: PRT
<213> ORGANISM: Artificial Sequence
<220> FEATURE:
<223> OTHER INFORMATION: synthetic peptide sequence
```

-continued

```
<400> SEQUENCE: 20

Gly Ala Ser Ser Gly Asn Ser Thr Asn Gly Thr Ser Asn Gly Ser Ser
1               5                   10                  15

<210> SEQ ID NO 21
<211> LENGTH: 42
<212> TYPE: DNA
<213> ORGANISM: Artificial Sequence
<220> FEATURE:
<223> OTHER INFORMATION: synthetic oligonucleotide primer

<400> SEQUENCE: 21
ccgtacgatt cgtatctact atcgttcgat tcgcatcatc ta                         42

<210> SEQ ID NO 22
<211> LENGTH: 21
<212> TYPE: DNA
<213> ORGANISM: Artificial Sequence
<220> FEATURE:
<223> OTHER INFORMATION: synthetic oligonucleotide primer

<400> SEQUENCE: 22
ggcatgctaa gcatagatga t                                                21
```

DIRECT ELECTRICAL READOUT OF NUCLEIC ACID SEQUENCES

CROSS REFERENCE TO RELATED APPLICATION

This disclosure claims the priority benefit of the earlier filing date of U.S. Provisional Patent Application No. 62/864,174 filed on Jun. 20, 2019, which is hereby incorporated by reference in its entirety.

ACKNOWLEDGMENT OF GOVERNMENT SUPPORT CLAUSE

This invention was made with government support under R21 HG010522 and R01 HG009180 awarded by the National Institutes of Health. The government has certain rights in the invention.

REFERENCE TO A SEQUENCE LISTING

This application incorporates by reference the Sequence Listing submitted in Computer Readable Form created on Jun. 19, 2020 and containing 6 kilobytes.

FIELD

This disclosure relates to sequencing, and in particular to devices, systems and methods for direct measurement of polymerase activity.

SUMMARY

Disclosed herein are devices, systems and methods for direct measurement of polymerase activity.

In some embodiments, a device is provided, the device comprising: at least a first electrode and a second electrode, the first and second electrode being separated by a gap; and a polymerase comprising two sites for attachment to the first and second electrodes, wherein the two attachment sites are separated by a distance of at least about 1 nm and the distance does not significantly change (that is a change in overall distance of less than 10%) with conformational changes of the polymerase, such as the two attachment sites have the same atomic coordinates when the polymerase is in an open or closed conformation.

In some embodiments, a system is provided, the system comprising a device as described herein and configured to practice one or more methods disclosed herein.

In some embodiments, a method of detecting incorporation of a nucleotide is provided, the method comprising: (a) introducing a solution comprising a nucleic acid template to a device as described herein; (b) measuring a first current generated when a bias is applied to the device; (c) introducing a solution comprising a dNTP to the device under conditions that allow for incorporation of the dNTP complementary to the nucleic acid template; (d) measuring a second current generated in step (c); (e) removing the solution comprising the unincorporated dNTP; (f) repeating steps (c) to (e); (g) obtaining a signal stream from the current generated in step (b) and step (d); (h) identifying a section of current signal that fluctuates between two levels of current for an amount of time greater than about 40 ms; and (i) detecting that the nucleotide has been incorporated if the signal stream comprises a pause.

In some embodiments, a method of determining the number of nucleic acids repeated in a nucleic acid template sequence is provided, the method comprising: (a) introducing a solution comprising a nucleic acid template to a device as described herein; (b) measuring a first current generated when a bias is applied to the device; (c) introducing a solution comprising a dNTP to the device under conditions that allow for incorporation of the dNTP complementary to the nucleic acid template; (d) measuring a second current generated in step (c); (e) removing the solution comprising the unincorporated dNTP; (f) repeating steps (c) to (e); (g) obtaining a signal stream from the current generated in step (b) and step (d), wherein the signal stream comprises at least one pause and at least one burst; (h) identifying sections of current signal that fluctuate between two levels of current an amount of time of greater than about 40 ms; and (i) determining that the nucleotide has been repeated in the nucleic acid template sequence if the signal stream comprises a pause that is about twice the length of a plurality of pauses in the signals stream.

In some embodiments, a method of determining the identity of a nucleotide being incorporated into a nucleic acid template sequence is provided, the method comprising: (a) introducing a solution comprising a nucleic acid template to a device as described herein; (b) measuring a first current generated when a bias is applied to the device; (c) introducing a solution comprising a dNTP to the device under conditions that allow for incorporation of the dNTP complementary to the nucleic acid template; (d) measuring a second current generated in step (c); (e) removing the solution comprising the unincorporated dNTP; (f) repeating steps (c) to (e); (g) obtaining a signal stream from the current generated in step (b) and step (d), wherein the signal stream comprises at least one pause and at least one burst; and (h) determining the identity of the incorporated nucleotide from the burst signal.

In some embodiments, a method of sequencing a nucleic acid sequence is provided, the method comprising: (a) introducing a solution comprising a nucleic acid template to a device as described herein, wherein the nucleic acid template comprises all possible 16 combinations of two sequential bases in the sequence; (b) introducing a solution comprising a dNTP to the device under conditions that allow for incorporation of the dNTP complementary to the nucleic acid template; (c) obtaining a signal stream from repeat sequences in the nucleic acid template, wherein the signal stream comprises at least one pause and at least one burst; (d) using a signal analysis to characterize the burst signal of each incorporated dNTP; and (e) applying the signal analysis for sequencing an unknown nucleic acid sequence.

The foregoing and other features of the disclosure will become more apparent from the following detailed description, which proceeds with reference to the accompanying figures.

BRIEF DESCRIPTION OF DRAWINGS

Embodiments will be readily understood by the following detailed description in conjunction with the accompanying drawings and the appended claims. Embodiments are illustrated by way of example and not by way of limitation in the figures of the accompanying drawings.

FIG. 1A-i shows Φ29 polymerase with a single Avitag at the N terminus (sequence N Contact 1). FIG. 1A-ii shows Φ29 polymerase with a second Avitag inserted between E279 and D280 (sequence Contact 2). FIG. 1Ai-iii shows Φ29 polymerase with the two Avitags and an additional flexible linker in the N terminus sequence (sequence N Contact 2).

FIG. 1B shows an SDS-PAGE gel showing the Gen III modified polymerase in lane 2. On incubating with strepta-vidin, the major product (red arrow) is a complex with a mass approximately equal to the polymerase plus two streptavidin molecules. Lane 4 is WT streptavidin.

FIG. 1C shows an agarose DNA gel showing elongation products from a rolling circle polymerization assay using (lane 1) the Gen III polymerase and (lane 4) the polymerase complexed with streptavidin. The rolling circle template is 5'-P-CCGTACGATTCGTATCTACTATCGTTCGATTCG-CATCATCTA-3' (SEQ ID NO: 4) and the primer for form-ing the double stranded region is 5'-GG-CATGCTAAGCATAGATGAT-3' (SEQ ID NO: 5).

FIG. 2 shows the sequences of the DNA templates used and their folded structures (SEQ ID NOs: 6-14).

FIG. 3A shows that A10 is sometimes fully extended as shown by the presence of some fully extended product in the first lane; C10 does not extend at all; and A10C10 may form a small amount of extended product, but polymerization usually halts abruptly at two locations. The homopolymer templates fail to extend fully. FIG. 3B shows that the non-homopolymer sequence (ATC)15 is readily extended to completion.

FIG. 4 shows a DNA sequence (SEQ ID NO: 15) and the primers that form nicks of 3, 6 and 9 base pairs (SEQ ID NOs: 16-18).

FIG. 8A shows raw data plotted in current vs. time. FIG. 8B shows a plot of derivative vs. time. This plot shows the irregular speed of the polymerase. FIG. 8C shows a high-resolution plot of current vs. time. This plot shows regular gaps in the signal at a mean interval of about 11.6 ms. FIG. 8D shows a pulse width distribution for a short segment of the data showing the gaps (width 0.5 ms) and the faster peaks between (width 0.2 ms).

(FIG. 14A) Gen I—one contact yields 2 peaks presumably because of additional contacts vis the surface cysteines on Φ29. (FIG. 14B) Gen II connected via thiolated streptavidins. (FIG. 14C) Gen III connected via WT streptavidin connected to the electrodes by thiolated biotin molecules. The red arrow points to the additional high conductance peak that appears as a conse-quence of the second contact point. (FIG. 14D) When a bare tip is used (Gen II, thio-streptavidin on the substrate) Peak 3 is no longer observed.

(FIG. 15A) Distri-bution in the absence of deoxynucleoside triphosphate (dNTPs) but with bound template. The polymerase is largely open. (FIG. 15B) In the presence of bound non-hydrolyzable dNTPs—the polymerase is locked in the close configuration. The highest conductance peak moves from 5.6 to ~15 nS.

FIG. 16A illustrates the current through the polymerase changes markedly over time as the STM probe drifts (curve 1602). This drifting baseline current is fitted with an asymmetric least squares (ALS) procedure to yield a smoothed background current (curve 1601 superimposed on curve 1602). (FIG. 16B) Subtraction of the fitted background shows the rapid changes in current that occur in an activated polymerase. Typically the dynamic signals occur in bursts (b-1603) interspersed with pauses (p-1604). FIG. 16C shows the current recorded vs time in the absence of the complementary nucleotide triphosphate 1605, and the ALS fit 1606. These data were chosen to have about the same DC conductance as the active polymerase in (FIG. 16A) and (FIG. 16B). FIG. 16D has the baseline subtracted signal shows that there is noise 1607 in the inactive system. The noise coincides with the formation of a contact to the polymerase in all cases, so it is not random. FIG. 16E shows an expanded portion of the noise signal measured from an activated polymerase showing two distinct noise compo-nents—large fluctuations (LF 1608) and small fluctuations (SF 1609). FIG. 16F is a histogram comparing the distribu-tion of spike heights from the active (+dTTP 1610) and inactive (−dTTP 1611) polymerase.

(FIG. 17D) In the presence of the complementary nucleo-tide, 9 out of 13 molecules showed a bimodal distribution of spike heights with $I_S$«$I_L$. (e) Values of $I_L$ (line 1701) and $I_S$ (line 1702) plotted vs the associated value of baseline current ($I_P$). Values of the single exponential distribution fitted for the −dTTP experiments are shown around line 1703. Lines are linear fits yielding $L_F$=0.25(±0.03)$I_p$ and $L_S$ 0.07(±0.01)$I_p$. The small fluctuations have essentially the same dependence on $I_p$ in the control experiments (−dTTP).

(FIG. 18C) and (FIG. 18G) FWHM distributions for ~1 s of signal traces (exponential fits are shown as the thin lines). (FIG. 18D) and (FIG. 18H) Interval between signals spikes, fitted with log-normal distributions (lines).

FIG. 19A shows the conductance distribution for thiolated streptavidin measured with a bare probe at a gap of 2.5 nm. Almost no data is collected when the gap is increased to 3.5 nm (see FIGS. 20A and 20B). FIG. 19B shows that after the addition of the mono-biotinylated Gen I polymerase, a quite different conductance distribution is obtained at a larger gap (3.5 nm). FIG. 19C shows the conductance distributions for the Gen III bisbiotinylated polymerase contacted via thiolated streptavidin to the electrodes and FIG. 19D as bound to WT streptavidin connected to the electrodes via thio-biotin ligands.

FIG. 20A shows conductance distributions as a function of gap size for Gen I monobiotinylated Φ29 bound to streptavidin on the electrodes. FIG. 20B shows conductance distributions as a function of gap size for streptavidin alone.

FIG. 22 shows a conductance distribution for Φ29 in the presence of template and dNTPs. The highest conductance feature has moved from ~6 nS (–dNTPs) to 12 nS. This increases to 15 to 20 nS when the polymerase is frozen in the closed configuration with non-hydrolyzable dNTPs.

FIG. 23 shows an example of an IV curve obtained from an active polymerase (see FIG. 22). Arrows point to large noise spikes in the normally quiet region below ±100 mV (compare to FIG. 13).

FIG. 24A provides current vs time with bound template, but no dNTPS. The highest current region is expanded in FIG. 24B. There are many jumps in the baseline, but no obvious two-level telegraph noise. FIG. 24C is a current-time recording with dNTPs added. Noise spikes are more evident and, when an expanded trace is plotted FIG. 24D clear bursts of two-level random telegraph noise are present. FIG. 24E is a histogram of burst duration, clearly longer for the +dNTP case. Note: in these plots current is increasing in the downward direction.

FIGS. 25A-25D illustrate the effect of background subtraction on polymerase signals. Effect of ALS background subtraction (smoothing factor=0.1 ms). FIGS. 25A and 25C are raw and subtracted data for a region of relatively flat baseline. FIG. 25B (raw) and FIG. 25D (subtracted) illustrate how the noise features are well-preserved even in the presence of large baseline variations.

FIGS. 26A and 26B show the difficulty of starting the polymerase on homopolymer teplates. The templates all contain hairpins, so, on a denaturing gel (20% polyacrylamide—8M Urea), the product shows up as a sharp higher molecular weight band if fully extended. FIG. 26A, the homopolymers: $A_{10}$ is sometimes fully extended as shown by the presence of some fully extended product in the first lane. $C_{10}$ does not extend significantly. $A_{10}C_{10}$ may form a small amount of extended product, but polymerization usually halts abruptly at two locations. FIG. 26B the non-homopolymer sequence $(ATC)_{15}$ is readily extended to completion. The length of the extended product was verified by running a gel with a synthetic control of the extended length.

FIG. 27A is a typical noise sample in a dense signal burst. FIG. 27B shows pulses that are closely spaced (~1 ms) and contain both fast (0.05 ms) and slower (0.2 ms) features in the distribution of pulse widths shown in FIG. 27C.

DETAILED DESCRIPTION OF DISCLOSED EMBODIMENTS

Figure 1A:
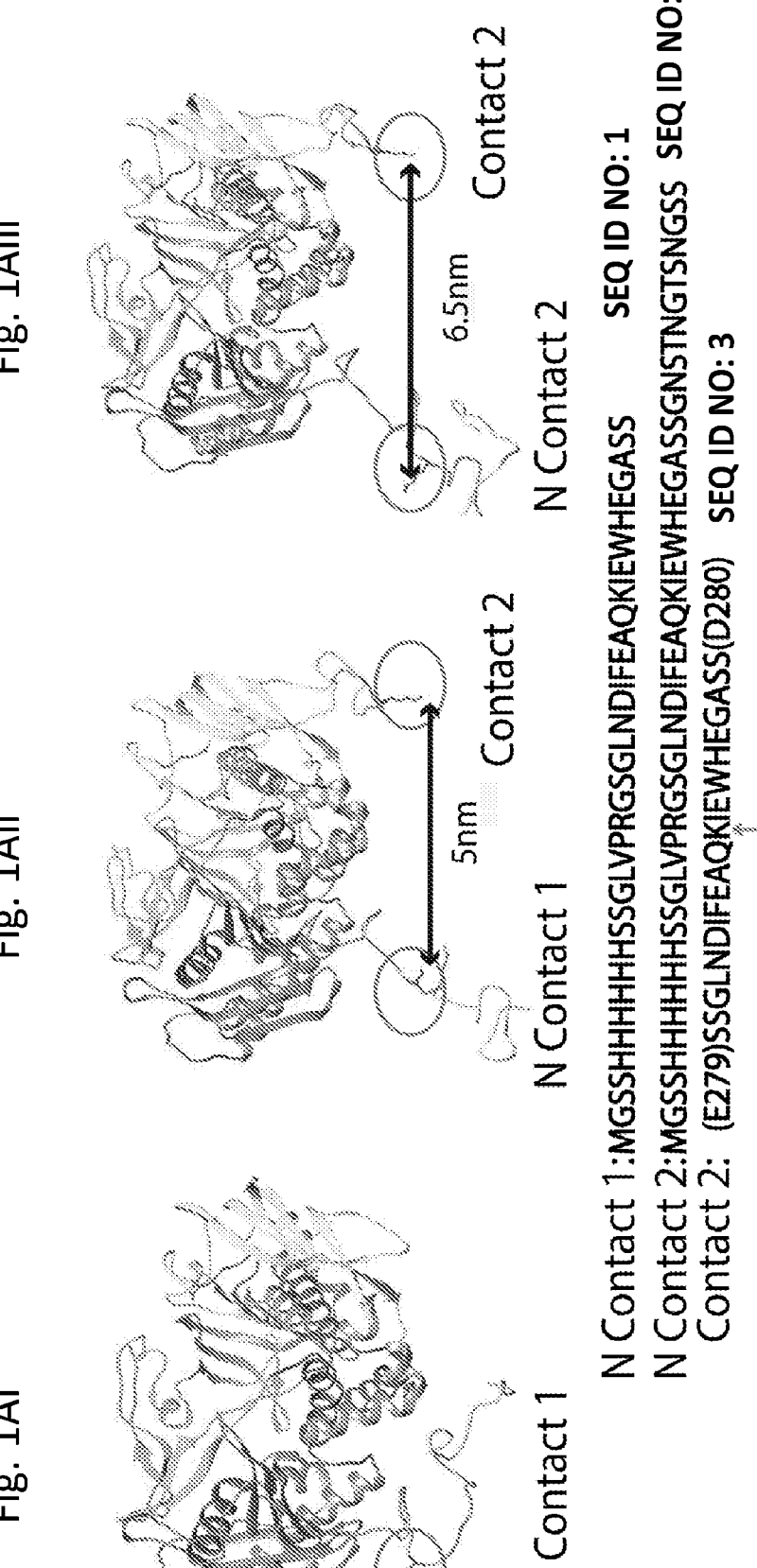
FIGS. 1Ai-1Aiii show schematics diagram of a polymerase having at least one contact.

In the following detailed description, reference is made to the accompanying drawings that form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The term "a" or "an" may mean more than one of an item.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

The term "about" means within plus or minus 10% of a stated value. For example, "about 100" would refer to any number between 90 and 110.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Other methods and materials similar or equivalent to those described herein can be used. In addition, the materials, methods, and examples are illustrative only and not intended to be limiting.

To facilitate review of the various embodiments of the disclosure, the following explanations of specific terms are provided:

Biological sample: A biological specimen containing genomic DNA, RNA (such as mRNA), protein, or combinations thereof, obtained from a subject. Examples include, but are not limited to, saliva, peripheral blood, urine, tissue biopsy, surgical specimen, and autopsy material. In embodiments, the biological sample is a bodily fluid, such as blood, or a component thereof, such as plasma or serum.

Burst: The term "burst" refers to a section of a current stream in which the measured current changes between two levels more frequently relative to a pause, typically being in the high state for half the time of a pause. In embodiments, the measured current of the peaks in a burst is greater than about 20% of the baseline current passing through the molecule. Typically, a burst is observed when a nucleotide is being incorporated into a template sequence in that the high state of the signal occurs at the incorporation of a nucleotide.

Chemical Modification: A number of various processes involving the alteration of the chemical constitution or structure of molecules. In one example, a chemically-modified electrode is an electrode that has a surface chemically converted to change the electrode's properties, such as its' physical, chemical, electrochemical, optical, electrical, and/or transport characteristics.

Contacting: Placement in direct physical association, including both a solid and liquid form.

Complementarity: The ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

Current stream: The term "current stream" refers to the current signal generated over time from a device described herein.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" may be understood to have been purified by standard purification methods. The term also embraces nucleic acid molecules and proteins prepared by recombinant expression in a host cell as well as chemically synthesized nucleic acid molecules and proteins.

Label: An agent capable of detection, for example, a label can be attached to a nucleic acid molecule or protein (indirectly or directly), thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, New York, 1989) and Ausubel et al. (In Current Protocols in Molecular Biology, John Wiley & Sons, New York, 1998).

Linked or linker: The term "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g., electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker" (a molecule or group of atoms positioned between two moieties).

In several embodiments, linked components are associated in a chemical or physical manner so that the components are not freely dispersible from one another. For example, two components may be covalently bound to one another so that the two components are incapable of separately dispersing or diffusing.

Nick: A discontinuity in a double stranded DNA molecule where there is no phosphodiester bond between adjacent nucleotides of one strand typically through damage or enzyme action. Nicks allow for release of torsion in the strand during DNA replication. Nicks may also play a role in the DNA mismatch repair mechanisms that fix errors on both the leading and lagging daughter strands. By creating nicks, the DNA forms a circular shape.

Non-naturally occurring or engineered: Terms used herein as interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

Nucleic acid: A deoxyribonucleotide or ribonucleotide polymer, which can include analogues of natural nucleotides that hybridize to nucleic acid molecules in a manner similar to naturally occurring nucleotides. In a particular example, a nucleic acid molecule is a single stranded (ss) DNA or RNA molecule, such as a probe or primer. In another particular example, a nucleic acid molecule is a double stranded (ds) nucleic acid, such as a target nucleic acid. The term "nucleotide" refers to a base-sugar-phosphate combination and includes ribonucleoside triphosphates ATP, UTP, CTG, GTP and deoxyribonucleoside triphosphates such as dATP, dCTP, dITP, dUTP, dGTP, dTTP, or derivatives thereof.

Optional: "Optional" or "optionally" means that the subsequently described event or circumstance can but need not occur, and that the description includes instances where said event or circumstance occurs and instances where it does not.

Pause: The term "pause" refers to a section of a current stream in which the fluctuations in measured current are interrupted by a slower feature of about twice the duration of the neighboring features. Typically, a pause is observed before and after a nucleotide has been incorporated into a template sequence, and the duration of the pause relative to the neighboring pulses of current increases as the concentration of nucleotide triphosphates is lowered.

Polymerase: An enzyme that synthesizes long chains of polymers or nucleic acids. DNA polymerase and RNA polymerase are used to assemble DNA and RNA molecules, respectively, by copying a DNA template strand using base-pairing interactions or RNA by half ladder replication.

Primer: a short nucleic acid molecule, for instance DNA oligonucleotides 10-100 nucleotides in length, such as 5, 6, 7, 8, 9, 10, 11, 12, or more in length. Primers can be annealed to a complementary target nucleic acid strand by nucleic acid hybridization to form a hybrid between the primer and the target nucleic acid strand. Primers can be used for amplification of a nucleic acid sequence, such as by PCR or other nucleic acid amplification methods known in the art.

Probe: A short sequence of nucleotides, such as at least 8, at least 10, at least 15, at least 20, or at least 21 nucleotides in length, used to detect the presence of a complementary sequence by molecular hybridization. In particular examples, oligonucleotide probes include a label that permits detection of oligonucleotide probe:target sequence hybridization complexes. Laboratory standards and values can be set based on a known or determined population value and can be supplied in the format of a graph or table that permits comparison of measured, experimentally determined values.

Protein: The terms "protein," "peptide," "polypeptide" refer, interchangeably, to a polymer of amino acids and/or amino acid analogs that are joined by peptide bonds or peptide bond mimetics. The twenty naturally-occurring amino acids and their single-letter and three-letter designations are as follows: Alanine A Ala; Cysteine C Cys; Aspartic Acid D Asp; Glutamic acid E Glu; Phenylalanine F Phe; Glycine G Gly; Histidine H His; Isoleucine I He; Lysine K Lys; Leucine L Leu; Methionine M Met; Asparagine N Asn; Proline P Pro; Glutamine Q Gln; Arginine R Arg; Serine S Ser; Threonine T Thr; Valine V Val; Tryptophan w Trp; and Tyrosine Y Tyr. In one embodiment, a peptide is an antibody or fragment or part thereof, for example, any of the fragments or antibody chains listed above. In some embodiments, the peptide may be post-translationally modified.

Under conditions sufficient to: A phrase that is used to describe any environment that permits the desired activity.

II. Devices, Systems and Methods of Use

The present disclosure provides devices, systems and methods for direct measurement of polymerase activity. In some embodiments, a device for direct measurement of polymerase activity is provided. In embodiments, the polymerase is a DNA polymerase. In some embodiments, the polymerase is an RNA polymerase.

In embodiments, the device comprises a first and a second electrode, the first and second electrode being separated by a gap; and a polymerase attached to one or both electrodes; wherein the first electrode and the second electrode have an opening formed therethrough.

In embodiments, the device comprises a first and a second electrode, the first and second electrode being separated by a gap; and a polymerase attached to one or both electrodes.

In some embodiments, the device comprises:

(a) a dielectric substrate;

(b) a first electrode disposed on the dielectric substrate;

(c) an insulating dielectric layer disposed on the first electrode;

(d) a second electrode disposed on the insulating dielectric layer;

(e) a passivation layer disposed on the second electrode; and (f) a polymerase attached to one or both the electrodes; wherein the first electrode, the insulating dielectric layer, the second electrode and passivation layer have an opening formed therethrough.

In some embodiments, the device comprises:

(a) a dielectric substrate;

(b) a first electrode disposed on the dielectric substrate;

(c) a second electrode disposed on the insulating dielectric layer;

(d) a passivation layer disposed on top of the electrodes; and (e) a polymerase attached to one or both the electrodes; wherein the passivation layer has an opening formed therethrough.

In some embodiments, the device comprises:

(a) a first and a second electrode, the first and second electrode being co-planar and separated by a gap and lying in a plane together with the second electrode;

(b) a polymerase attached to at least one of the first or second electrodes, such as attaching to the first electrode by a first attachment site and to the second electrode at a second attachment site so that the first attachment site and the second attachment site do not move relative to each other when the polymerase undergoes open-to-closed conformational changes; and wherein the first electrode and the second electrodes are configured for contact with a sample to be analyzed.

In embodiments in which the electrodes are planar, the device advantageously does not require a dielectric layer. Devices requiring dielectric layers can suffer from drawbacks. Dielectric layers require adhesion layers to adhere to the electrodes. These adhesion layers can oxidize upon exposure to air, which, in effect, increases the size of the gap between the electrodes. To compensate for this effect, the dielectric layer can be made thinner. However, a thin dielectric layer is susceptible to pinholes, which can be difficult to eliminate.

In each of the device embodiments described herein, the first and/or second electrode comprise a metal selected from the group consisting of gold, platinum, palladium, and ruthenium or alloy thereof. In some embodiments, the metal is palladium.

In some embodiments, the gap has a width of about 1.0 nm to about 20.0 nm. In some embodiments, the gap has a width of about 1.0 nm to about 10.0 nm. In some embodiments, the gap has a width of about 1.0 nm to about 7.5 nm. In some embodiments, the gap has a width of about 1.0 nm to about 5.0 nm. In some embodiments, the gap has a width of about 4.0 nm to about 5.0 nm.

Attachment Points on the Polymerase

The polymerase can be attached to one electrode in one embodiment and to both electrodes in a second embodiment. The polymerase can be attached to the electrode(s) either directly or indirectly. In some embodiments, the polymerase is attached to the first electrode at a first attachment site and to the second electrode at a second attachment site. In some embodiments, the polymerase is attached to an electrode at a first site of the polymerase, such as at the n-terminus of the polymerase and a second site which is in the inactive region of the polymerase. In some embodiments, a first attachment site is specifically modified for attachment at one electrode and a second attachment site that is non-specific, but within an inactive region in the polymerase. In some embodiments, the polymerase is attached to the electrode(s) via a linker. In some embodiments, the polymerase is attached to the electrode indirectly via interactions with a ligand attached to the electrode. In some embodiments, the polymerase is modified to incorporate a ligand-binding site. In some aspects, the polymerase is a biotinylated polymerase. In some aspects, the polymerase comprises an Avitag. In some aspects, the polymerase is a biotinylated polymerase and is attached to the electrode via streptavidin. In some embodiments, the polymerase is modified to incorporate a Streptag.

In some embodiments, the polymerase is modified to incorporate an amino acid residue that allows for click-chemistry attachment of other chemical groups to the electrodes (e.g., 4-Azido-L-phenylalanine). When the polymerase is attached to both electrodes, the distance between the two attachment points is at least about 1 nm to about the overall size of the polymerase. In one embodiment, the distance is from about 1 nm to about 20 nm. In embodiments, the distance is about 1 nm to about 10 nm. In embodiments, the distance is about 1 nm to about 5 nm. In embodiments, the distance is from about 3 nm to about 7 nm. In another embodiment, the distance is from about 5 nm to about 6 nm. In embodiments, the distance is about 1 nm, about 2 nm, about 3 nm, about 4 nm, about 5 nm, about 6 nm, about 7 nm, about 8 nm, about 9 nm, about 10 nm. In embodiments, the distances is no more than about 10 nm, such as no more than 10 nm, 9 nm, 8 nm, 7 nm, 6 nm, 5 nm, 4 nm or 3 nm.

When the polymerase is attached to both electrodes, the two attachment points must not move relative to each other, when the polymerase undergoes open-to-closed conformational changes. The crystal structure of many polymerases is available (see, for example, www.rcsb.org/) in both open and closed forms. Thus, when selecting the two attachment points, the two residues (e.g., attachment points) must be separated from each other and have the same atomic coordinates in both the open and closed forms. In embodiments, the attachment sites are in the inactive region of the polymerase.

Figure 1C:
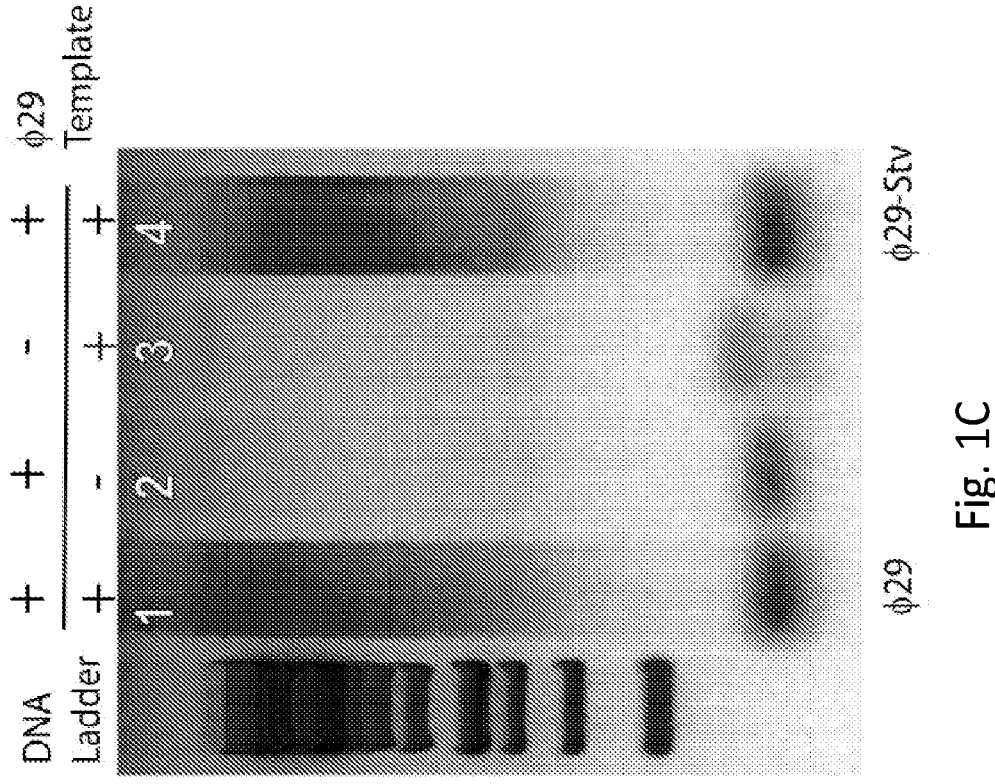
Figure 1B:
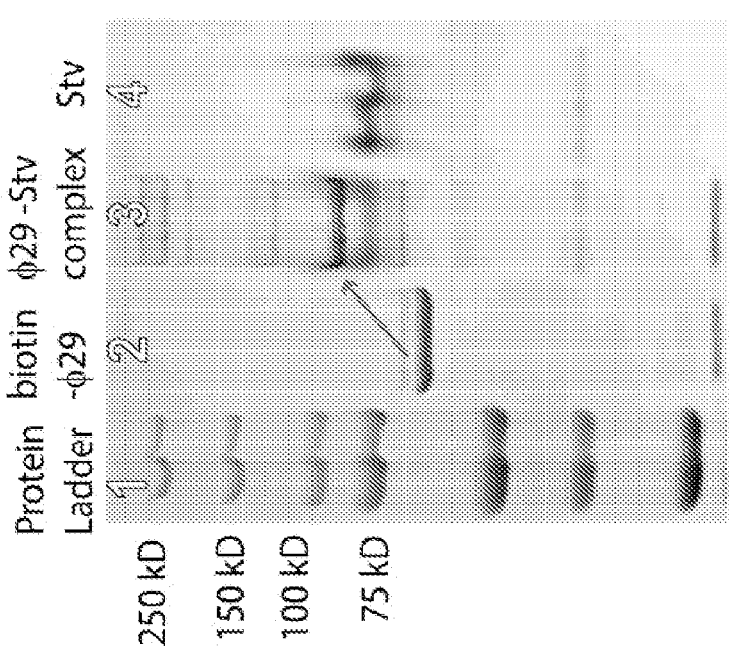

When the polymerase comprises two Avitag linkers, the ability to bind two streptavidin molecules is demonstrated by the formation of the appropriate product on a protein gel, as shown in FIG. 1B.

The polymerase, as modified, must function efficiently, as shown by a rolling-circle amplification assay in FIG. 1C. Note that this assay shows that the modified polymerase, attached to the streptavidin molecular wires, performs continuously and repeatedly polymerization on a circular template. Therefore, circular templates can be used for repeated sequencing of a given molecule.

In some embodiments, the polymerase incorporates an inserted flexible sequence as shown in FIG. 1A. It is contemplated that any peptide can be used as the flexible sequence as long as (a) it does not form an alpha helix or a beta sheet and (b) the residues in the sequence do not substantially change the pI relative to the pI of the unmodified polymerase (i.e., a change is smaller that one pH point). An exemplary flexible sequence is GASSGN-STNGTSNGSS (SEQ ID NO: 20).

The Polymerase Template

In some embodiments, the device further comprises a nucleic acid template. The nucleic acid template is a DNA template in one embodiment and an RNA template in a second embodiment, such as a nucleic acid template with 9 or more nucleotides or bases, such as 9, 10, 11, 12, 13, 14, 15, 16, 17, 18, 19 or 20 etc. nucleotides or bases.

For the polymerase to operate at maximum speed, and for the electrical signals to be readily processed, it is a requirement that the polymerase not be stalled or obstructed by secondary structures formed by the DNA template. This is particularly true in the case where the template contains single stranded regions. FIG. 2 as well as the Example section provides exemplary primer templates that can be used. FIG. 3 shows the products of polymerization reaction on a denaturing gel. Because the templates are self-primed by hairpins (FIG. 2), full extension of the template by a polymerase results in only one product at the molecular weight of the fully polymerized chain. FIG. 3 shows that this is only the case for the homopolymer d(ATC)5.

In order for the technique to work on genomic DNA, templates must be double stranded to remove the secondary structures formed by single-stranded DNA. It is expected that obstructions will, nonetheless remain. Methods to identify those regions from the signal are discussed below. Polymerase Φ29 has excellent strand displacement activity but does not start efficiently at a nick of only one nucleotide. To address this, primer libraries with larger nicks can be used. Exemplary primers are provided in FIG. 4.

The present disclosure also provides a system for direct measurement of a polymerase activity. The system comprises a device as described herein; a means for introducing a nucleic acid template and dNTPs; a means for applying a bias between the first and second electrode of value; and a means for monitoring fluctuations that occur as a dNTP interacts with a polymerase.

Methods of Use

The present disclosure provides methods of using the devices described herein. In a first embodiment, the present disclosure provides a method for detecting the incorporation of a nucleotide. In a second embodiment, the present disclosure provides a method of determining the number of nucleotides repeated in a nucleic acid template. In a third embodiment, the present disclosure provides a method of determining the identity of a nucleotide being incorporated into a nucleic acid template sequence. In a fourth embodiment, the present disclosure provides a method of sequencing a nucleotide. Also disclosed are methods for sequencing a homopolymer sequence by counting the number of repeats of a pause-burst-pause sequence in the presence of a single nucleotide. Further, methods to analyze current signals in the case where more than one molecule is present in the gap/junction are disclosed in which signal levels are counted, such as a signal level of 2 indicates 1 molecule is present in the junction, a signal level of 3 indicates 2 molecules are present etc.

The signature of an active polymerase is the presence of current fluctuations on the millisecond timescale that are 25% or more of the DC current flowing through the polymerase. See "Engineering an Enzyme for Direct Electrical Monitoring of Activity". Small fluctuations, on the order of 10% of the DC current are always present, even in the absence of components critical to the function of the polymerase. As such, fluctuations of 10% or less indicate the polymerase is inactive. 50 to 70% of the molecules studied are active when wired into a circuit. A second limitation occurs in functionalizing "wider" electrodes so that that there is sufficient space for more than one polymerase molecule to bridge the electrode gap and attach to both electrodes. For example, if the electrode lengths are 10 nm, only one polymerase could attach to both electrodes. However, if the electrode lengths are 20 nm, 2 polymerase molecules could attach to both electrodes.

Figures 5A, 5B:
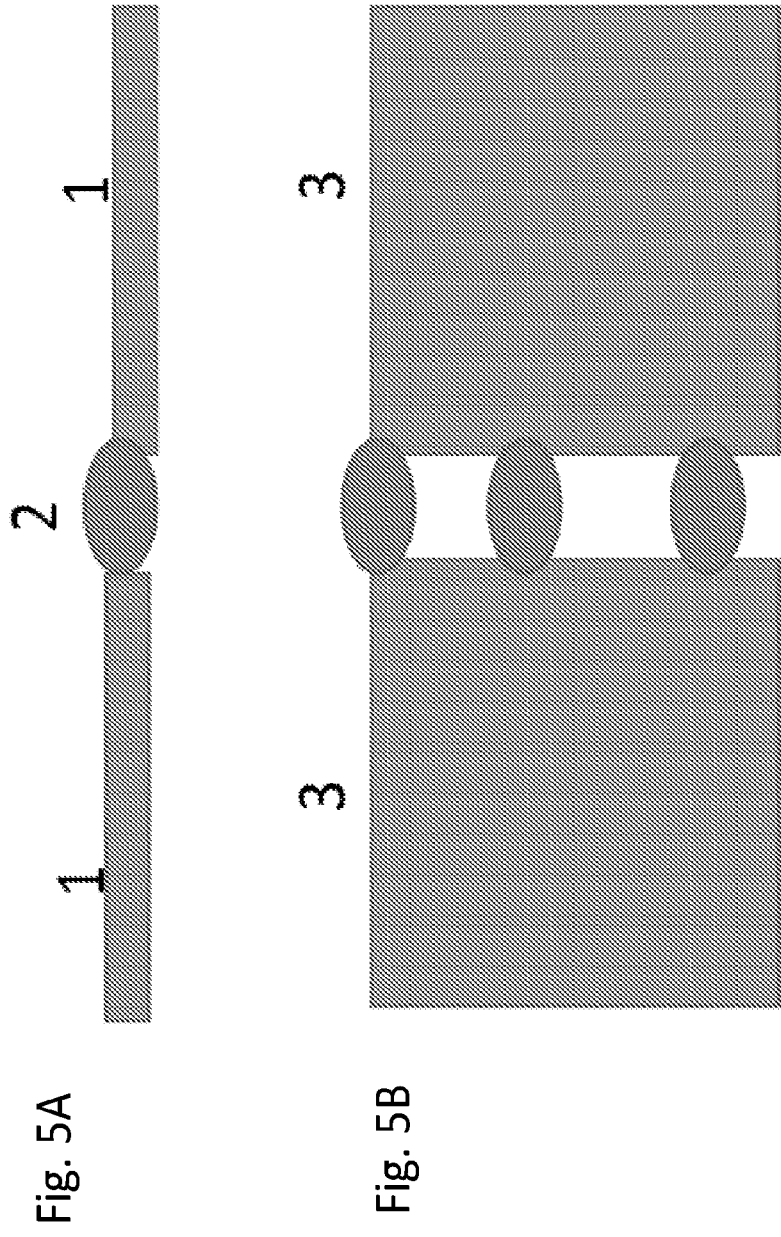
FIG. 5A shows a schematic diagram of a pair of electrodes bridged by a polymerase.
FIG. 5B shows a schematic diagram of a pair of electrodes bridged by three polymerase molecules.
Figure 6:
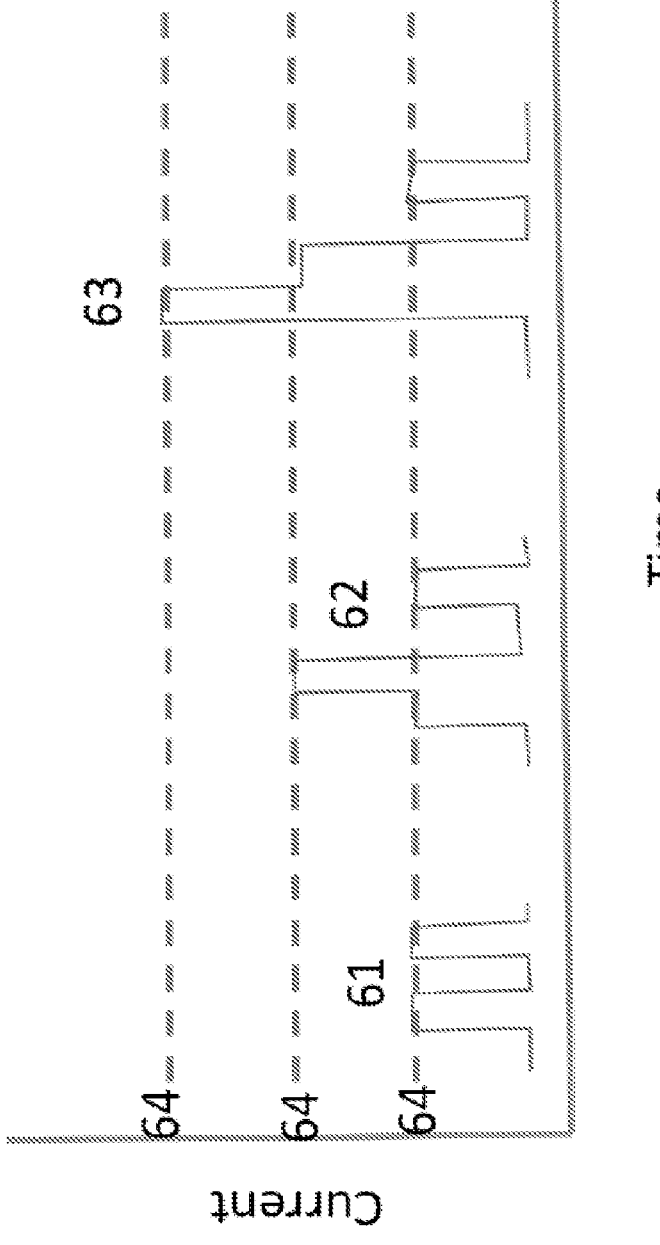
FIG. 6 shows a plot of current vs. time obtained from a device as described herein comprising one (61), two (62) or three (63) polymerase molecules attached to both electrodes. Each polymerase molecule generates a signal.

Referring to FIG. 5, it is possible to ensure that only one molecule (2) bridges a gap in electrode (1) by making the electrodes sufficiently narrow. However, functionalizing narrow electrodes is difficult because the probability that a suitable coupling geometry exists in a narrow gap is small. However, in wider electrodes (3) more than one polymerase may bind. However, as discussed below, the preferred signals generated by an active polymerase consisting of two well defined signal levels. With more than one molecule in the gap, signals are additive, as illustrated in FIG. 6 which shows representative signals for one (61), two (62), and three (63) molecules in one device. Because the currents from each molecule consist of two levels, identifying devices that contain more than one molecule is straightforward. Furthermore, the number of molecules in each device can be counted by counting the discrete current levels (64). For a few (2, 3 or 4) molecules, a machine-learning algorithm' can be trained, using known template sequences, to recognize these more complicated signals from multiple molecules in the gap.

Filtering Signals

Figures 3A, 3B:
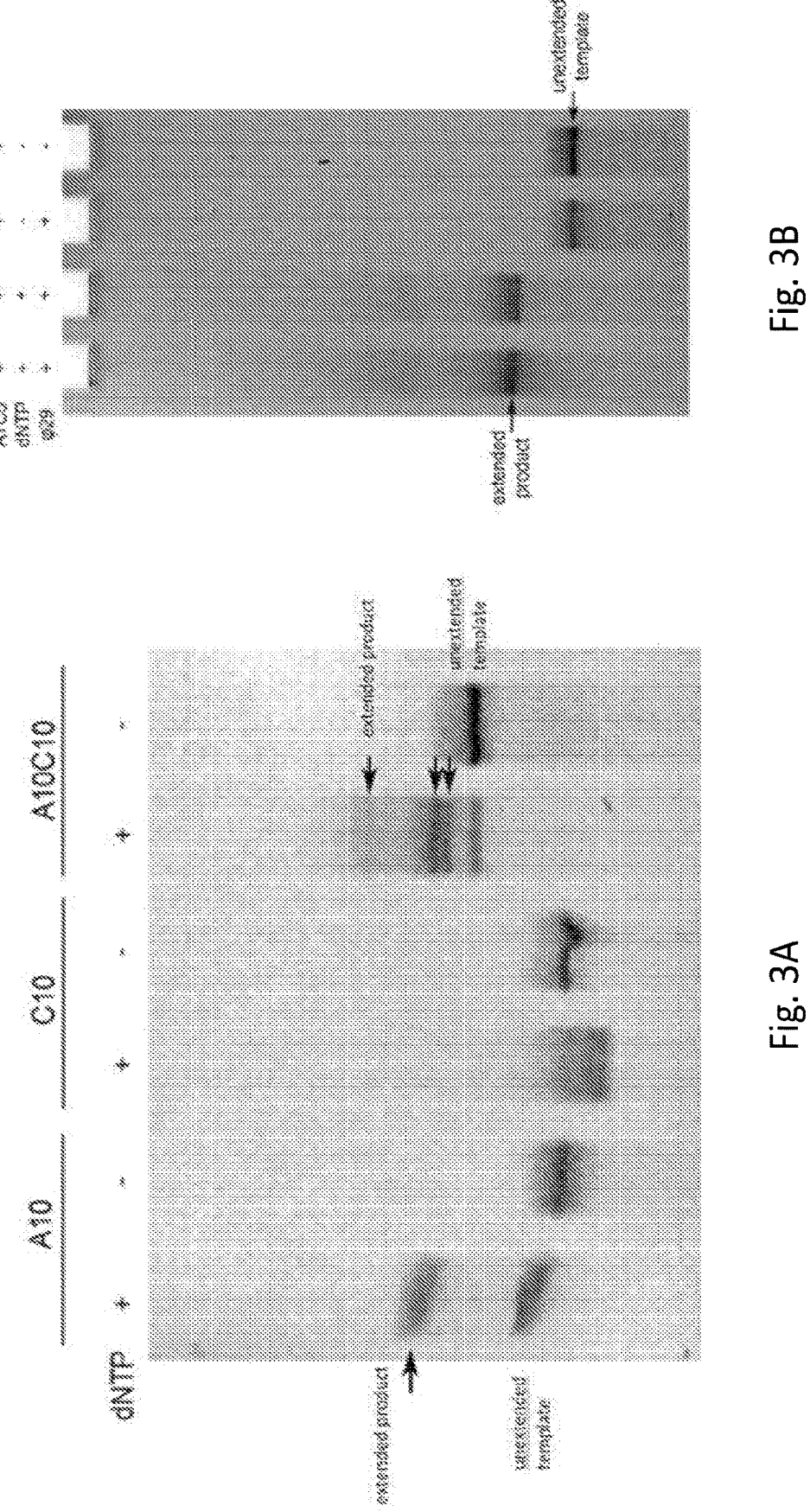
FIGS. 3A and 3B show urea-PAGE gel (denaturing gel) (20% polyacrylamide-8M Urea) for a homopolymer sequence (FIG. 3A) and a non-homopolymer sequence (FIG. 3B). The templates all contain hairpins, so, on a denaturing gel (20% polyacrylamide-8M Urea), the product shows up as a sharp higher molecular weight band if fully extended.

The large signals are only observed for active polymerases, but the nature of the signal changes drastically, depending on the ability of the polymerase to process a template. As shown in FIG. 3A, the d(C)10 templates are hardly extended at all and the d(A)10 templates are extended sporadically. The d(ATC)5 templates are extended efficiently (FIG. 3B). Correspondingly, signals from d(A)10 templates and d(C)10 templates are irregular, fluctuating in amplitude and pulse width, signals labeled as "chaotic" in FIGS. 7A and 7B. In contrast, signals obtained with the efficiently processed d(ATC)5 are uniform in amplitude with time (FIG. 7C) and labeled as "Processive". Processive signals are those in which the polymerase is working its way through a template whereas chaotic signals indicate the polymerase is attempting to mount a template. The disclosed devices, systems and methods allow the differences between the two to be evaluated.

Figures 7A, 7B, 7C, 7D, 7E:
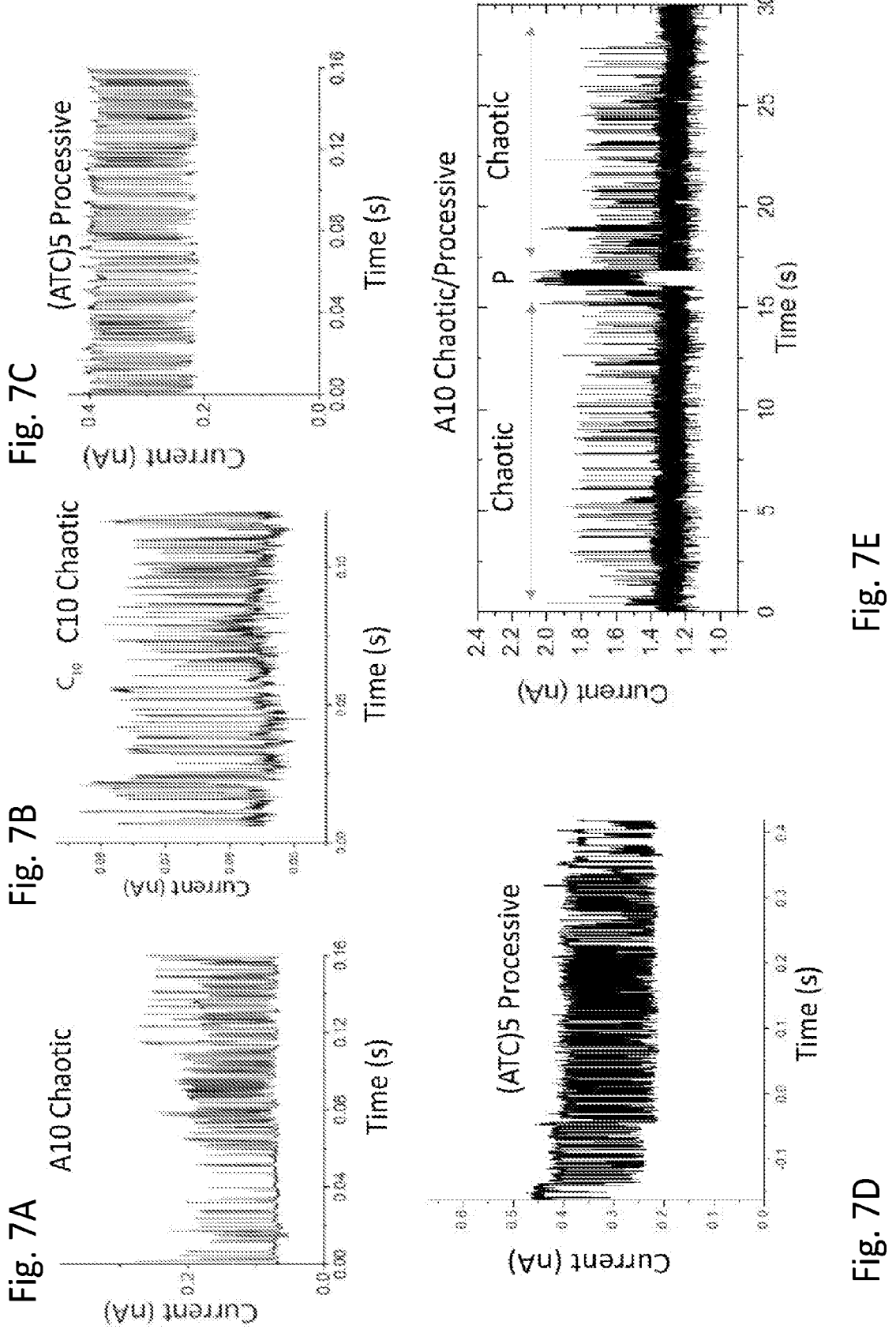
FIGS. 7A-7E show examples of chaotic and processive signals.

Processive signals continue over extended times if the template is efficiently processed as shown by the longer run in FIG. 7E. In templates that are at least partially fully processed (i.e. d(A)10—FIG. 3A) chaotic signals are interspersed with processive signals (FIG. 7E). Sequencing is greatly simplified on double stranded templates where many types of sequence are efficiently processed by Φ29 polymerase, resulting in long runs of processive signals. Even in double stranded DNA, secondary structure will stall a polymerase, for example in a run of G bases where G tetraplexes form. These structures are readily identified by a return to the chaotic signal type. In embodiments, the chaotic spikes are removed/rejected.

Interpreting Signals

Figures 8A, 8B, 8C, 8D:
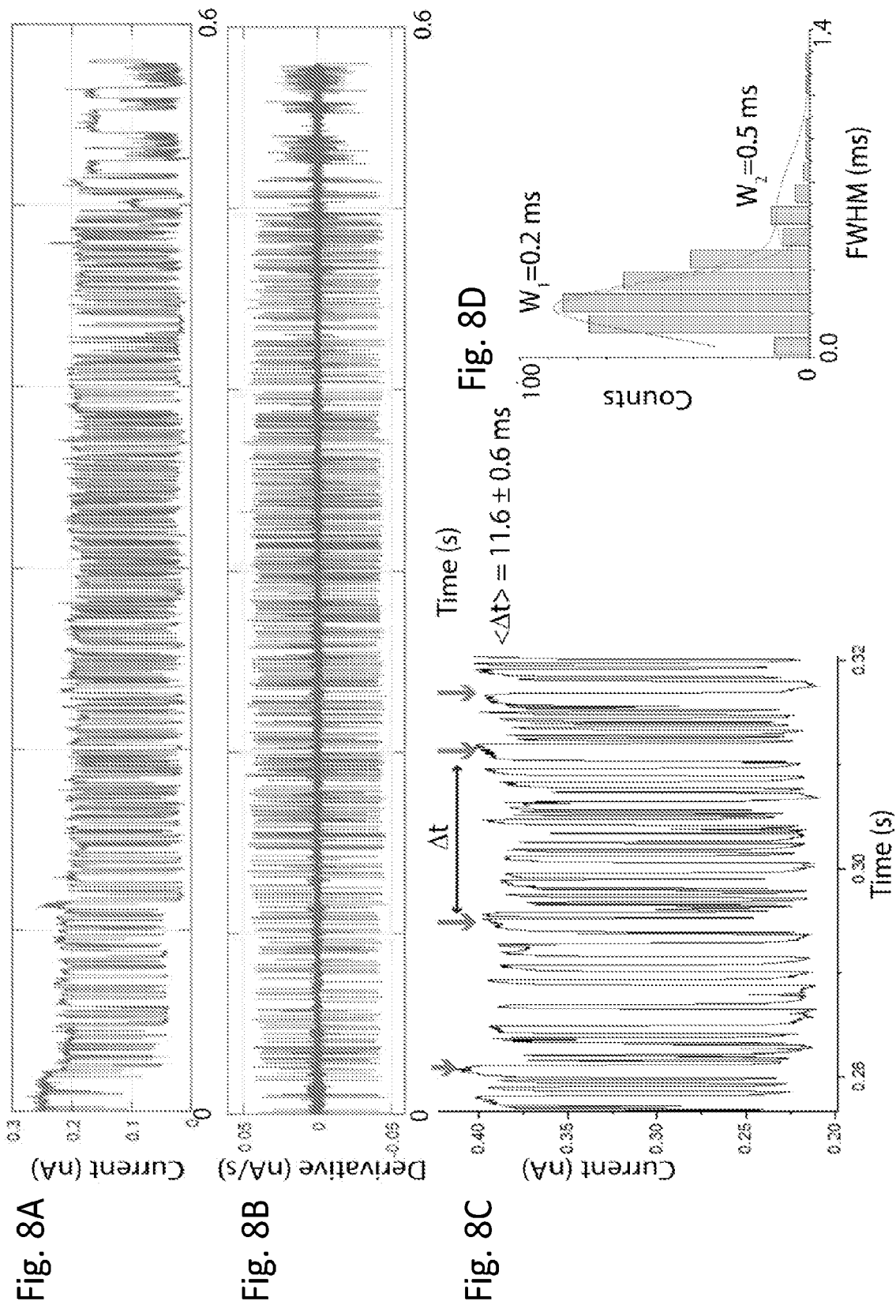
FIGS. 8A-8D show data the electrical signal obtained when a polymerase is processing a repeated (ATC) sequence.
Figure 9:
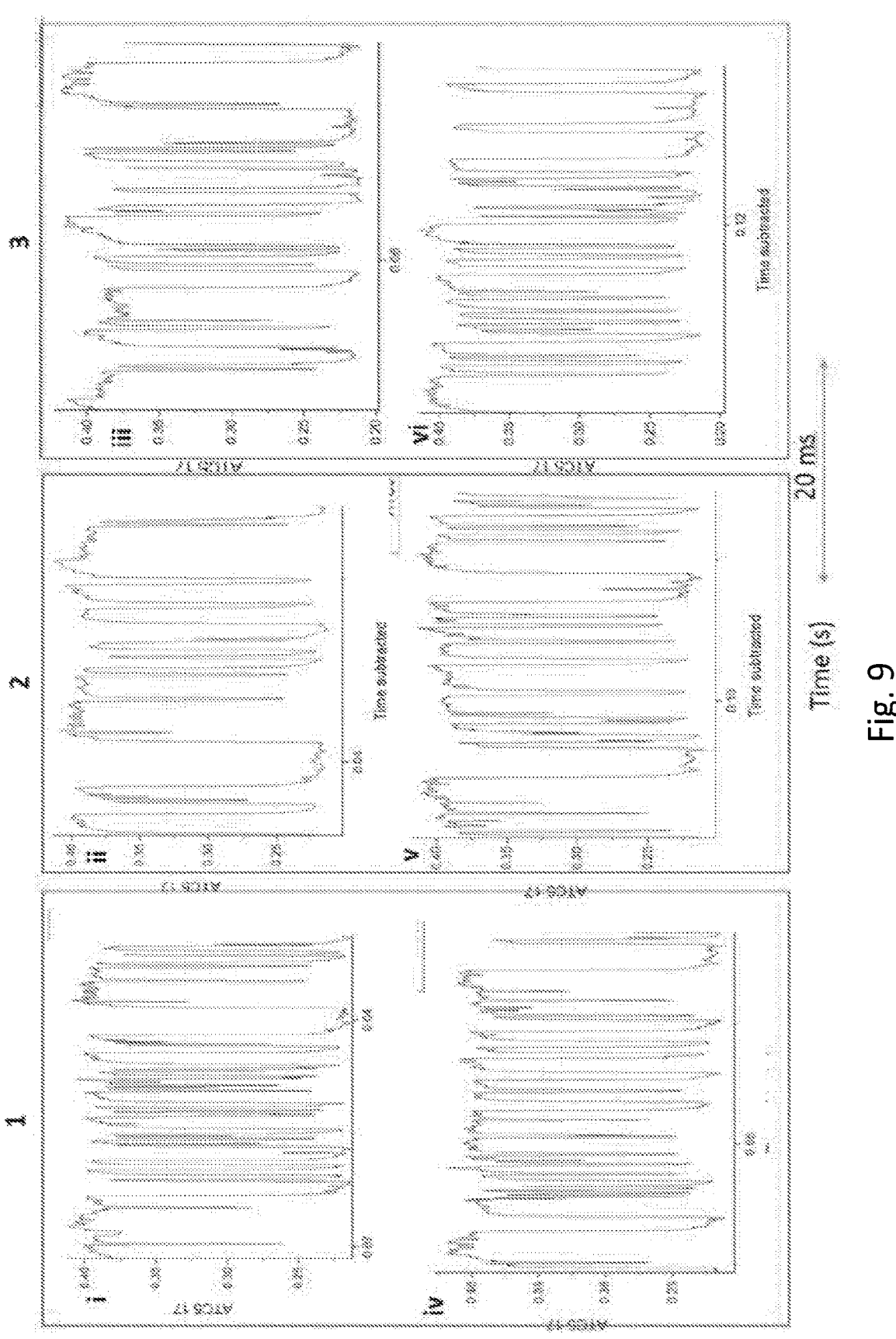
FIG. 9 shows plots of current vs. time for a DNA template consisting of (ATC) repeats. Repeated motifs are observed in panels i and iv and ii and v, consistent with the threefold sequence repeat.

Processive runs are straightforward to interpret. A high time resolution signal is shown in FIG. 8. There are distinct pauses at intervals of about 12 ms, corresponding to the known nucleotide incorporation rate of Φ29 polymerase4 in the saturating concentrations of dNTP used here (marked by the arrows in FIG. 8C). Thus, the processive signals allow for a straightforward way of counting each nucleotide incorporation. This is extremely advantageous in interpreting signals from runs of repeated sequence, notoriously difficult to analyze with present methods. More interesting yet is the rich detail inside each pulse. FIG. 9 shows a time sequence of pulses from the d(ATC)5 polymer, acquired in the time sequence shown by the Roman numerals. There is clearly a threefold repeat in the signal (labeled 1,2,3).

The presence of a threefold repeat in a polymer with a threefold repeat in its sequence is not, by itself, enough to identify bases in a heteropolymer. A major factor in polymerase selectivity is stacking between the penultimate base and the dNTP being incorporated so that contacts with the polymerase do not change much between the four nucleotides—that is to say, polymerase-nucleotide contacts (which could generate a nucleotide specific signal) are not themselves very nucleotide specific. There are sequence-specific differences in incorporation kinetics whereas measurable differences in the incorporation kinetics of the various combinations of dNTP and penultimate base have been shown, as a consequence of base-stacking interactions in the polymerase binding pocket as the incoming dNTP is loaded on top of the previously incorporated nucleotide. Each pulse is a nucleotide incorporation.

The method for decoding these signals comprises:
(a) constructing double stranded templates comprising repeats of all possible 16 base stacking combination (e.g., A on A, A on T, A on C, A on G and so on);
(b) introducing a solution comprising a dNTP to the device under conditions that allow for incorporation of the dNTP complementary to the nucleic acid template;
(c) obtaining a signal stream from all 16 combinations of repeat sequences, wherein the signal stream comprises at least one pause and at least one burst;
(d) training a machine learning algorithm (Chang, S.; Huang, S.; Liu, H.; Zhang, P.; Liang, F.; Akahori, R.; Li, S.; Gyarfas, B.; Shumway, J.; Ashcroft, B.; He, J.; Lindsay, S., Chemical recognition and binding kinetics in a functionalized tunnel junction. *Nanotechnology* 2012, 23 (23), 235101 which is hereby incorporated by reference in its entirety) to recognize the burst associated with each of the 16 types of signal; and
(e) using the algorithm to identify each nucleotide in the signal from a heteropolymer by finding the best fit to the training model developed with the 16 possible stacking combinations. The starting point, that is to say the nucleotide immediately before the first new nucleotide incorporated is known because the sequence of the primer template is known.

The algorithm analyzes the signal stream to characterize the bursts in between each pause, by the number of pulses, their durations, sharpness as characterized by Fourier transforms, the intervals between them, and then training a machine-learning algorithm to associate signal features with a particular nucleotide or nucleic acid sequence.

Other Nucleic Acids

Figures 10A, 10B, 10C:
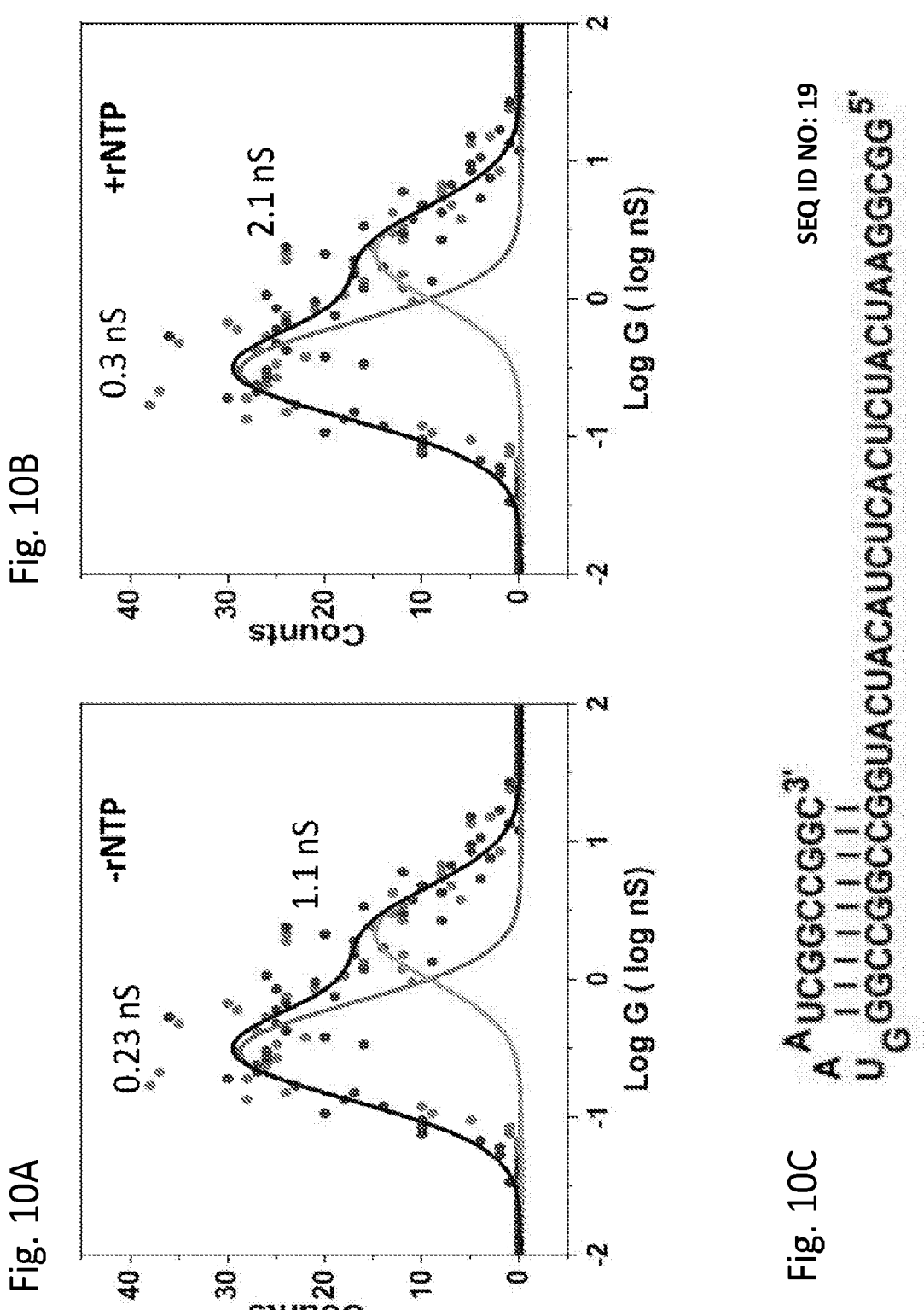
FIGS. 10A and 10B shows conductance distributions for 3D RNA polymerase in the absence (FIG. 10A) and pres-ence (FIG. 10B) of ribonucleotide triphosphates.
FIG. 10C shows the sequence of the RNA template being processed (SEQ ID NO. 19).
Figures 11A, 11B:
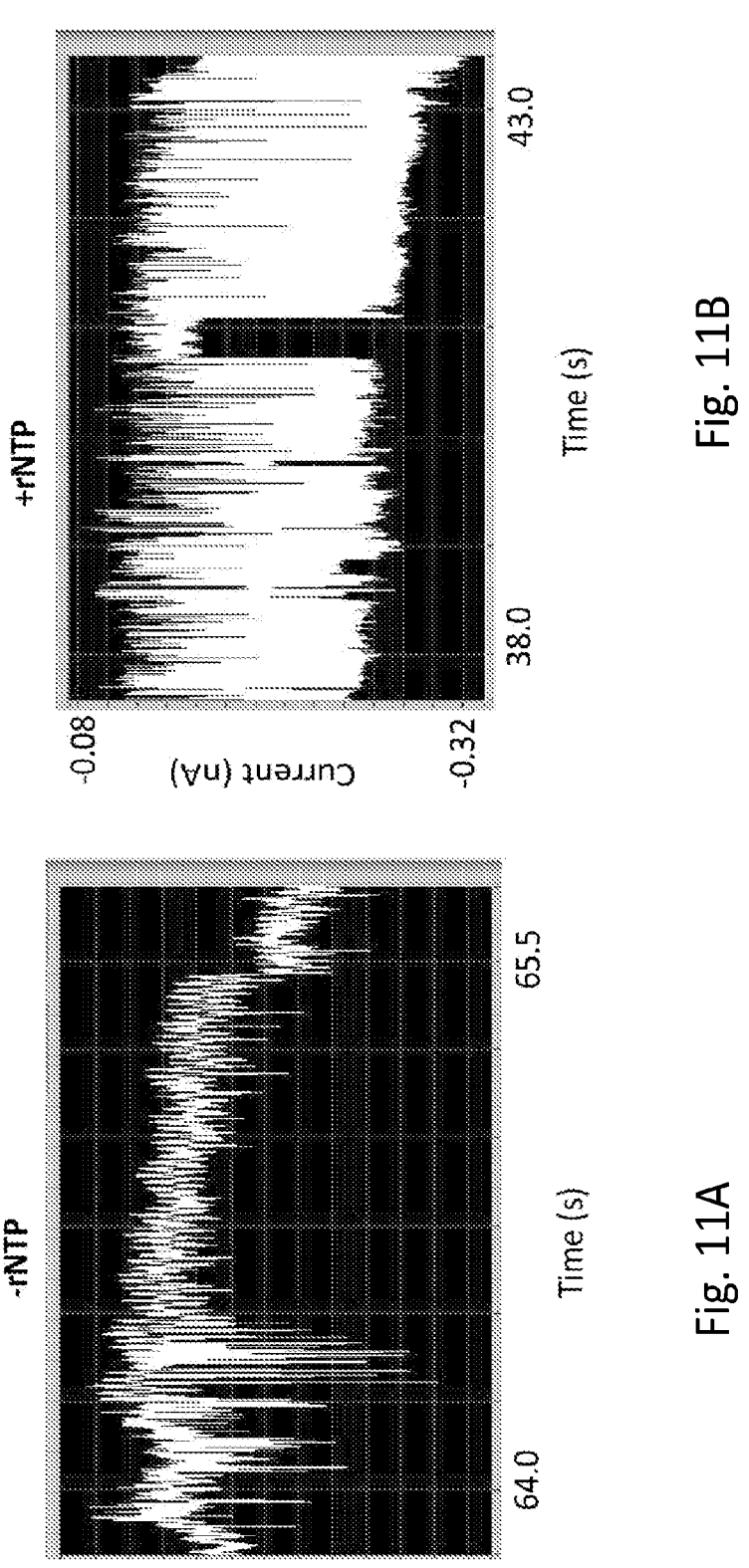
FIGS. 11A and 11B show current vs. time recordings for 3D RNA polymerase in the absence (FIG. 11A) and presence (FIG. 11B) of ribonucleotide triphosphates.

FIG. 10 shows conductance distributions measured on an RNA dependent RNA polymerase, polio virus 3D pol (RSCPDB structure 1RDR). This polymerase has been modified to include the peptide sequence known as a Strep tag at its C-terminus. This binds streptavidin, allowing a single specific connection to an electrode, as described in the Examples below. FIG. 11 shows conductance distributions for 3D pol primed with a hairpin RNA template (FIG. 10C). The conductance of the polymerase is increased dramatically, greater than 25% of the baseline current passing through the polymerase when it is active, as previously observed for DNA polymerase. Similarly, large current fluctuations are only observed when the polymerase is polymerizing the RNA template, as shown in FIG. 11.

EXAMPLES

Example 1

Materials and Methods for Example 2 and Representative Embodiments

This Example provides the materials and methods utilized for the studies disclosed in Example 2 and for representative embodiments disclosed herein.

Expression and purification of Avitag φ29 DNA polymerase. *E. coli* strain BL21 (DE3) (Novagen) was transformed with different versions of the φ29 gene embedded in pET15b plasmid and grown on an LB agar plate (1% tryptone, 0.5% yeast extract, 0.5% NaCl, and 1.5% agar) containing ampicillin (50 μg/ml) to select the transformants. Cells were grown in LB medium (20 ml) at 37° C. with shaking for 12 hours. A part of the culture was diluted 1:1000 into fresh LB medium (1 L) and grown at 37° C. with shaking. The 1 L culture was induced by adding 0.5 mM IPTG when the $OD_{600}$ reached 0.6 and kept shaking overnight at 18° C. Cells were harvested in a 1 L centrifuge bottle by centrifugation at 5,710 g for 20 minutes at 4° C. and stored at −80° C. until required.

Biontinylation of Avitag φ29 DNA polymerase. For subsequent BirA biotinylation, the purified protein was exchanged to a buffer containing 20 mM potassium phosphate buffer pH 7.0, 200 mM L-Glutamic acid potassium salt and 1 mM DTT. The in vitro enzymatic biotinylation was performed by incubating 100 μg of polymerase in the same buffer with 10 mM ATP, 10 mM Mg(OAc)₂, 50 mM biotin and 15 units of BirA (Avidity) for 1 hour at 30° C. Free biotin was removed by a desalting column (GE Life Sciences).

Rolling circle replication (RCR) ssDNA template and primer. Linear single strand oligonucleotides RCR (5'-p-CCGTACGATTCGTATCTACTATCGTTCGATTCGCAT-CATCTA-3'; SEQ ID NO: 21) was used to form circular RCR template by enzymatic self-ligation with Circligase (Epicentre). 0.1 nmol linear single strand RCR DNA was mixed with 100 Units Circligase in 1× reaction buffer containing 50 μM ATP and 2.5 mM MnCl₂. After 2 hours incubation at 60° C., the product was heated up to 80° C. for 10 minutes to inactivate the Circligase. The linear ssDNA left in the solution was digested by Exo I (NEB). The RCR template was analyzed by electrophoresis on a denaturing gel containing 8 M urea and 20% polyacrylamide for quality control. 2.5 pmols of RCR template was annealed with 50 pmols RCR primer (5'-GGCATGCTAAGCATAGATGAT-3'; SEQ ID NO: 22) by heating up to 95° C. for 5 minutes and gradually cooling down to room temperature (decreasing 0.1° C./s) and stored at −20° C. for later use.

Activity assay of Avitag φ29 DNA polymerase. A rolling circle replication reaction was performed for the activity test of all versions of φ29 DNA polymerase. 1.25 pmols RCR template and primer complex was mixed with 500 μM dNTP and 4 pmols φ29 DNA polymerase in 1× reaction buffer containing 50 mM Tris-HCl ph7.5, 10 mM MgCl₂, 10 mM (NH₄)₂SO₄, 4 mM DTT. The mixture was incubated at 30° C. for 1 hour. The product was visualized on 0.8% agarose gel by GelRed (Biotium) staining.

Functionalizing substrates and STM probes. Palladium substrates for STM measurement were prepared by evaporating a 200 nm palladium film onto a silicon wafer using an electron-beam evaporator (Lesker PVD 75), with a 10 nm titanium adhesion layer. The substrates were treated with a hydrogen flame immediately before functionalizing and then immersed in solutions of thiolated streptavidin (Protein-Mods) or thiolated biotin overnight. The thiolated biotin was prepared and dissolved in freshly degassed pure ethanol to a final concentration of 50 μM. 1 μM thiolated streptavidin solutions in 1 mM PB buffer were used for substrate functionalization. All the buffers and solutions were prepared in Milli-Q water with a conductivity of 18.2 MΩ. For all measurements, the 1 mM PB buffer (pH 7.4) was degassed with argon to avoid interference from oxygen. The polymerization buffer was 1 mM phosphate buffer, pH=7.4, 4 mM TCEP, 10 mM MgCl₂ with 1 mM dNTPs and 1 μM template. Sequences of the self-priming templates used are shown in FIG. 1Ai-1Aiii. Substrate functionalization was characterized by Fourier transform infrared (FTIR) spectroscopy. STM probes were etched from a 0.25 mm Pd wire (California Fine Wires) by an AC electrochemical method. To avoid current leakage, probes were insulated with high-density polyethylene following the method described earlier for gold probes. Each probe was tested by STM in 1 mM phosphate buffer (pH 7.4) at +0.5 V bias to ensure the leakage current was <1 pA. For functionalization, the probe was immersed in ligand solutions for 4 h or overnight. After that, it was taken out, rinsed with water, gently blown dry with nitrogen gas, and used immediately. Cyclic voltammetry was used to check that the potential regions used (+50 to −50 mV vs Ag/AgCl, 10 mM KCl) were free from Faradaic currents in the presence of the various components of the assembly.

STM Measurements. STM measurements were carried out on a PicoSPM scanning probe microscope (Agilent Technologies), using a DAQ card (PCI-6821 or PCIE-7842R, National Instruments) for data acquisition. The Teflon cell, in which buffer solution and analytes were added, was cleaned with Piranha solution and then sonicated in Milli-Q water three times to remove residues (Note that Piranha solution is highly corrosive and must be handled with extreme care). In order to better control the surface potential, an Ag/AgCl reference electrode with a 10 mM KCl salt bridge was connected onto the substrate. The probe was firstly engaged to 4 pA setpoint current with a bias of −0.2 V and then left to stabilize for 2 h before measurement. For STM IV sweep measurements, the servo system was first turned off and the probe was retracted by AZ nm with a speed of 1 nm/s. After that, the probe was suspended at that height for 1 minute, during which a custom Labview program was used to monitor the current change. Once the current exceeded a threshold of 50 pA, we considered it as a binding event and IV sweeps were started from −0.2 V to +0.2 V and then back, with a sweep rate of 1 V/s, followed by a 0.2 s resting. Subsequently, the current was checked again. If the current was still more than twice the noise level (6 pA), IV curves were continuously recorded until the bound protein molecule escaped. After one-minute of measurement, the servo system was turned on to re-engage the probe and then the whole process repeated. In each measurement, at least 1000 IV curves were collected, from which curves that reproduced on the up sweep and down sweep were selected (80% of the total) to construct the conductance distribution histogram. Current vs. time traces were recorded by another Labview program with a similar procedure except that the bias was held constant during the probe holding process. The analog-to-digital sampling rate is 50 KHz, about 5 times the intrinsic response of the STM electronics.

Example 2

Proteins have been shown to be electrically-conductive if tethered to an electrode by means of a specific binding agent, opening the possibility of building electronic devices that exploit the remarkable chemical versatility of enzymes by direct read-out of activity. Single-molecule conductance increases tenfold if two specific contacts are made (as is possible with bivalent antibodies). Here, the problem of forming contacts with proteins that, unlike antibodies, do not possess a multiplicity of native binding sites was addressed. In particular, contact points were engineered into a Φ29 polymerase, with the points chosen so as to leave the active site free. Contacts are formed by introducing biotinylatable peptide sequences into Φ29 and functionalizing electrodes with streptavidin. Φ29 connected by one biotinylated contact and one non-specific contact showing rapid small fluctuations in current when activated. Signals were greatly enhanced with two specific contacts, a feature in the conductance distribution changing by >9 nS between the open and closed conformations of the polymerase. Polymerase activity is accompanied by large changes in conductance over the millisecond timescale.

Proteins are widely assumed to be insulators. Reports of metallic conduction in bacterial wires and long range conduction in protein multilayers were thought to be exceptions. However, a number of proteins, chosen only for their redox inactivity (i.e. no electron transport function, no redox active centers) conduct very well if contacted by binding agents that can inject charge carriers into their interiors. This conductance is limited to electrons (or holes) because the proteins we have studied to date act to passivate electrodes in cyclic voltammetry studies. Furthermore, the internal conductance of the protein is sensitive to conformational changes. Key to these experiments was the use of antibodies together with electrodes that were functionalized with an epitope to which the two binding domains of the antibody could bind. The spread of conductances (owing to the range of contact geometries) was measured by recording current-voltage (IV) curves from approximately 1000 molecules, and plotting histograms of the conductances derived from the IV curves. Distributions for antibodies had two peaks, one at ~0.2 nS (similar to the value of the single peak observed for proteins bound by only one ligand) with a second peak at ~10× the conductance (~2 nS). The second peak was interpreted as owing to specific binding events at each binding domain of the antibody, attached so that the antibody bridges the electrode gap. This interpretation was confirmed using Fab fragments (one binding head) or functionalizing only one of the two electrodes with an epitope. It was also found that the internal conductance of proteins contacted via specific bindings agent is higher than the conductance associated with contact regions, so that that the measured electronic properties do not change much with gap size, until contact is lost with the protein. Proteins are remarkably versatile molecular machines, capable of molecular recognition, highly selective catalysis, directional energy transfer, directed polymer synthesis and many other functions, so integration of proteins into bioelectronic devices has been a long sought-after goal, and here the problem of making specific contacts to proteins that do not have multiple ligand binding sites was addressed, with the goal of demonstrating a device that transduces enzyme activity into electrical signals directly.

Φ29 polymerase was selected to be evaluated. It is a preferred polymerase for DNA sequencing applications because it is highly processive, has a high strand displacement activity (needing only a nick to initiate polymerization) and is very accurate (1 part in $10^6$). It is also fast, turning over 100 nucleotides per second at saturating concentrations of nucleotidetriphosphates (dNTP) and template. The major motion of the enzyme involves the closing of a "finger" domain into the "palm" and "thumb" once template and matching dNTP are assembled and ready for incorporation. At some point over the open-closed-open transition, the enzyme translocates the template so that the next available site is positioned for binding of the complementary dNTP.

Here, the engineering of specific binding sites for electrical contacts into Φ29 polymerase is reported using insertion of the Avitag sequence into a clone for the polymerase, and subsequently biotinylating the lysine within the Avitag peptide sequence using the BirA enzyme. This then allows for strong, and specific binding to Streptavidin. Initially a Φ29 biotinylated was tested just at the N terminus (Gen I), and bound to electrodes that had been covered with thiolated Streptavidin. Biotin-bound Streptavidin makes an excellent molecular wire and also serves to keep the Φ29 (with its seven surface cysteines) away from the metal electrodes. A second contact was introduced about 5 nm distant from the first (Gen II), at a site in the (inactivated) exonuclease domain. A third type of polymerase (Gen III) was made by incorporating a flexible linker next to the N-terminal Avitag. Finally, direct tethering of a thiolated Streptavidin to the electrodes was compared, with indirect tethering, using a thiolated biotin molecule to functionalize the electrodes. Both conductance distributions (by recording current-voltage, IV, curves) were measured and dynamic responses by recording current vs. time (I(t)) for bound polymerases in a gap of nominally constant size. The introduction of two binding sites introduced a new high conductance feature in the conductance distribution, analogous to the second peak found naturally for antibodies with two binding domains. It was also found that the indirect connection of streptavidin via thiolated biotin gives higher conductance than direct connection via surface thiolation of the streptavidin. The conductance of the Φ29 was found to increase greatly in the closed conformation. The change in DC conductance measured the between open and closed states is consistent with the scale of large dynamic swings in the current recorded through the enzyme as a function of time when the enzyme is active.

Results and Discussion

Recombinant Φ29 DNA Polymerase Constructs with Inserted Avitag

The starting enzyme was a Φ29 DNA polymerase, rendered exonuclease-deficient with D12A and D66A mutations. A Q5 site-directed mutagenesis kit (NEB) was used to insert the Avitag DNA sequence into a pET15b plasmid containing the mutant polymerase gene. The equivalent inserted peptide sequence is shown with flanking linker sequences, in FIGS. 1Ai-1C. The epsilon-amine of the central lysine (K, marked by an arrow on FIG. 1Aii-iii) was biotinylated using the BirA enzyme. Three generations of modified enzyme were tested. The first (FIG. 1Ai) was biotinylated only at the N terminus of the protein. The second (FIG. 1Aii) contained a second Avitag approximately 5 nm from the N terminus between E279 and D280. This second site is located in the deactivated exonuclease domain and was chosen because its position does not change with respect to the N terminus over the open to closed transition. The third (FIG. 1Aiii) contained an additional flexible linking sequence (GNSTNGTSNGSS; SEQ ID NO: 22) adjacent to the N-terminal Avitag to allow for greater flexibility in contact geometry. Biotinylation was verified with a SDS-PAGE gel analysis of the free- and streptavidin bound polymerases. FIG. 1B shows the increase in molecular weight that occurs as two streptavidins are bound to the Gen III polymerase (yet higher molecular weight features are likely polymer aggregates of alternating polymerase and streptavidin). The activity of the modified polymerases was verified in vitro using a rolling circle amplification assay (FIG. 1C).

Scanning Tunneling Microscope Conductance Measurements

Figure 12:
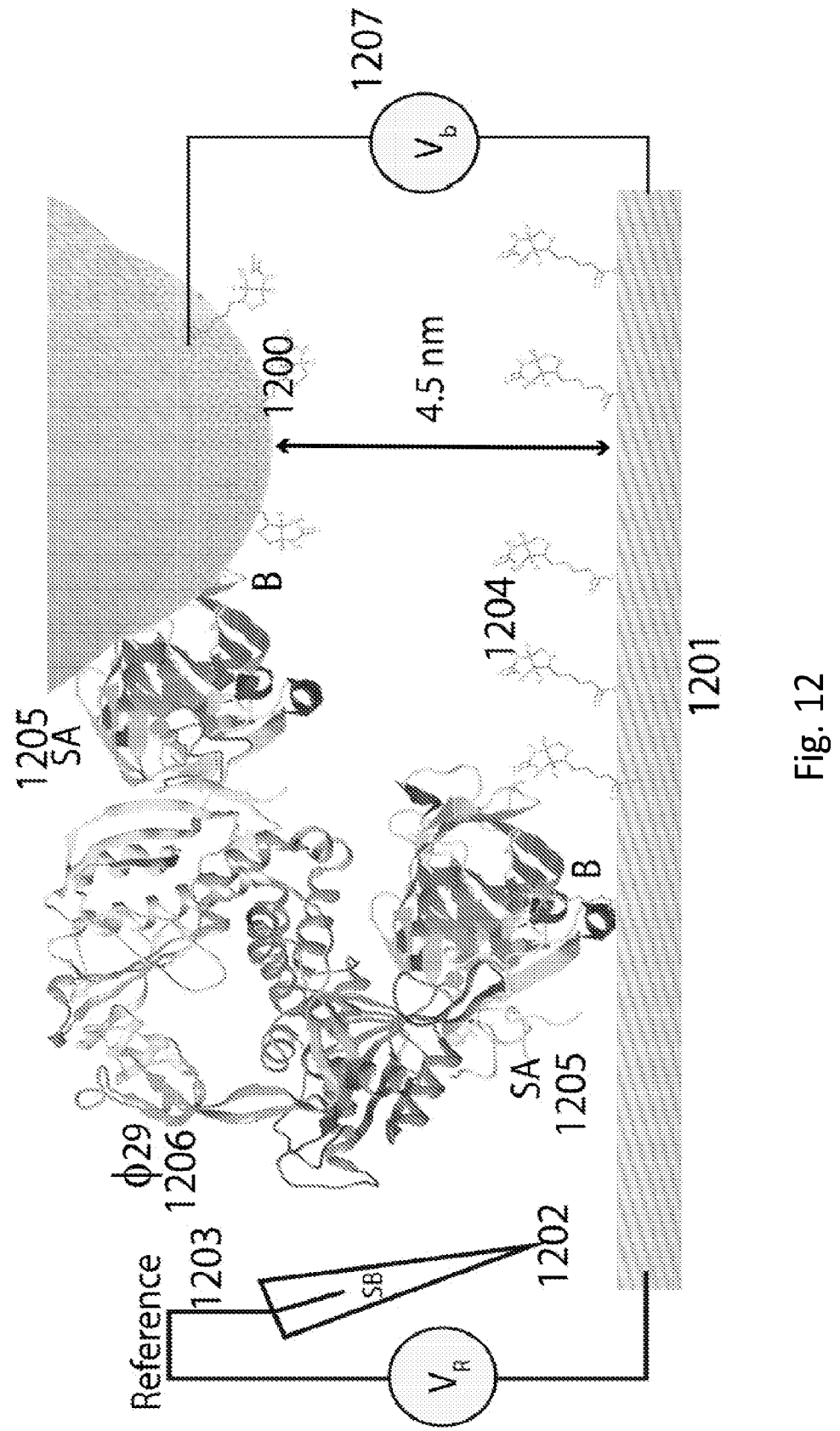
FIG. 12 is a schematic illustrating polymerase with streptavidin contacts bridging a pair of electrodes in accor-dance with embodiments provided herein.

Measurements were made using an electrochemical scanning tunneling microscope (Pico STM, Agilent) with insulated palladium (Pd) probes and a Pd substrate, both held under potential control using a salt-bridged reference electrode (FIG. 12). Electrodes were modified with either a thiolated biotin (SH-biotin) or thiolated streptavidin, and then incubated with a solution of the biotinylated polymerase (Methods). Measurements were made in a reaction buffer containing $MgCl_2$ and tris(2-carboxyethyl)phosphine) (TCEP) to prevent polymerase oxidation. Nucleotide triphosphates were added to activate the polymerases. Current-voltage (IV) characteristics were measured using a fixed gap (no servo control). The gap remained constant to within about 0.1 nm over approximately 1 minute, and the bias was swept between –0.2 and +0.2V and back again at a rate of 1 V/s. No attempt was made to fish for proteins or to push or pull them. Thus, the trapped proteins that yielded signals were molecules that bound across the gap in equilibrium, or near equilibrium conformations. After 1 minute, the gap was returned to the set-point value. This cycle was repeated to obtain further IV sweeps. 80% of these sweeps reproduced exactly on reversing the sweep direction. (In a number of runs, the current was recorded before re-engaging the servo to check that there had been no significant drift.)

In the present example, both probe and substrate are functionalized with streptavidin. In consequence, two streptavidin molecules can contact each other across the gap. When contacts are successfully made with streptavidin, they recapitulate the distribution observed for single streptavidin molecules and no signals are observed from streptavidin alone for gaps larger than 3.5 nm. However, when biotinylated polymerase is allowed to complex with the streptavidin, significant currents are measured out to gap distances >4.5 nm with conductance distributions that are quite distinct from that of streptavidin. The data reported in this Example were obtained with a gap of 4.5 nm unless noted otherwise.

FIG. 12 shows polymerase with streptavidin contacts bridging a pair of electrodes. As illustrated in FIG. 12, an STM probe 1200 is held ~4.5 nm above a conducting substrate 1201, immersed in electrolyte and under potential control via a salt bridge (SB) 1202 connected to an Ag/AgCl reference 1203. The electrodes are functionalized with thiolated biotin 1204 which captures streptavidin molecules (SA) 1205 which then trap a polymerase (Φ29) 1206. A bias Vb 1207 is applied between the electrodes. Potentials are maintained so as to avoid Faradaic currents.

Figure 13:
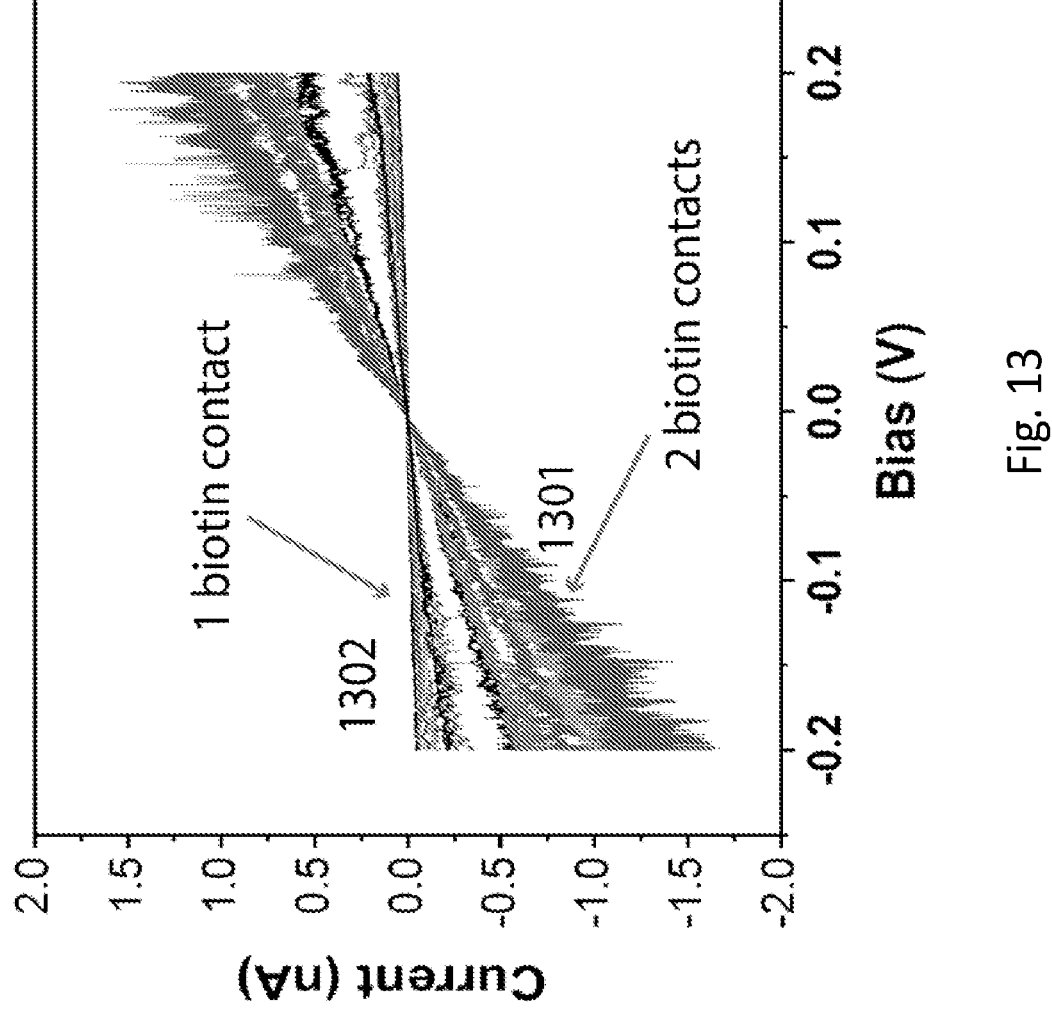
FIG. 13 shows current-voltage curves for different con-nections between the molecular complex and the electrodes.

FIG. 13 shows a selection of IV curves for a Gen I and Gen II polymerase. Forward and reverse sweeps are superimposed demonstrating reproducibility. Typical current-voltage curves from a trapped single molecule of polymerase. Each trace is for a sweep from –0.2V to +0.2V and then back to –0.2V. The conductances for individual molecules are obtained from the slope of these traces. Currents are increased by about an order of magnitude for Gen III polymerase (2 biotin contacts FIG. 1Aiii—scans are labeled 1301) compared to Gen I polymerase (1 biotin contact FIG. 1Ai—scans are labeled 1302).

The response is linear, with the exception of noise spikes that appear above ±100 mV as a consequence of voltage-induced contact fluctuations. The slope of each trace was used to calculate a conductance, G=I/V and histograms of conductance (based on ~1000 measurements each) are shown for the three generations of polymerase in FIGS. 14A-14D.

Figures 14A, 14B, 14C, 14D:
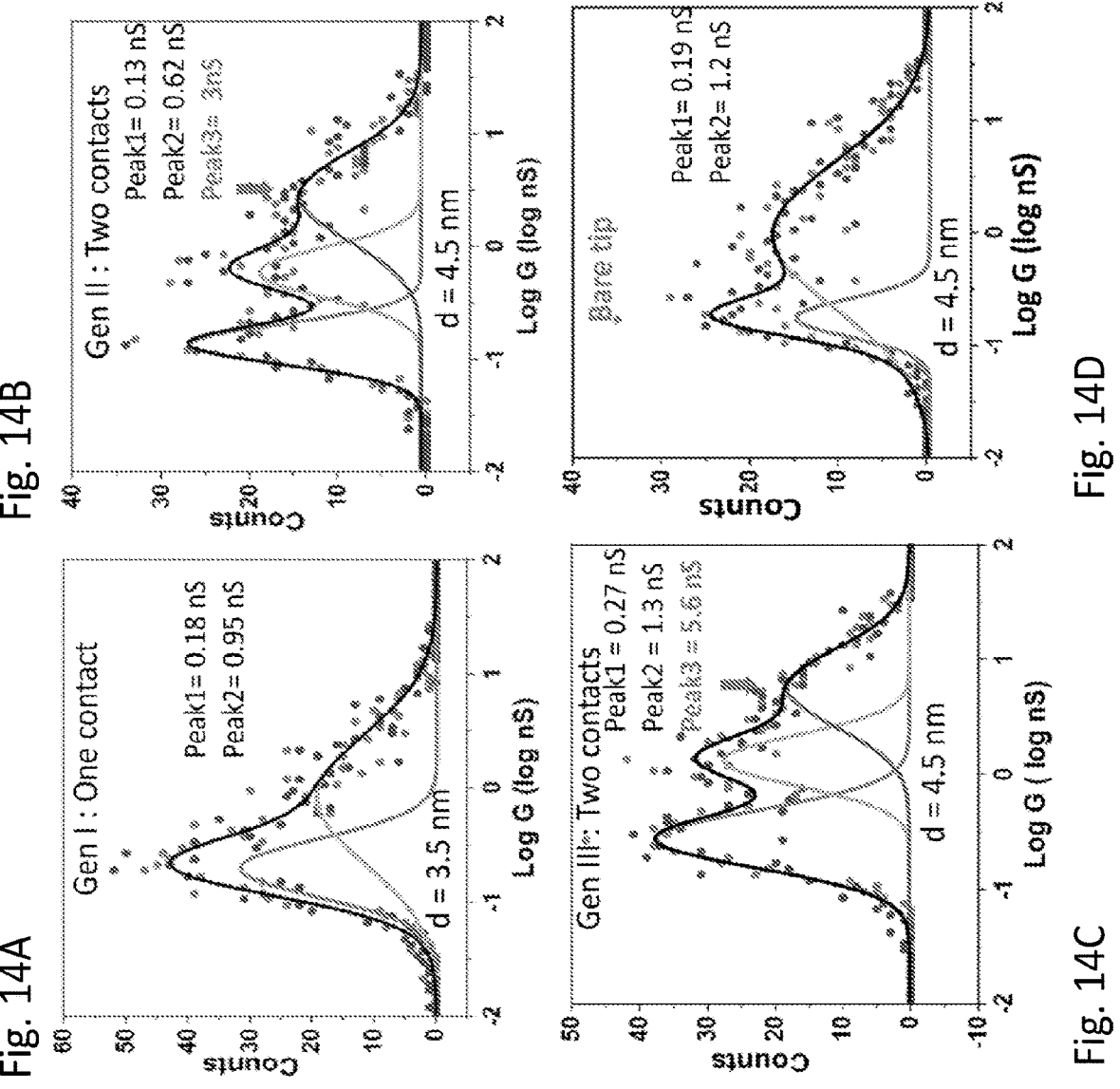
FIGS. 14A-14D show conductance distributions for the three generations of polymerase.

The Gen I polymerase forms only one specific contact, but in contrast to what we have observed in the past for proteins with a single binding site, there are two peaks in the conductance distribution, one at about 0.2 nS (characteristic of a weak, non-specific binding) and a second peak at ~1 nS. It is believed that the second peak is a consequence of additional surface linkages owing to the seven surface cysteines in this polymerase (conductance via a thiolated streptavidin is highly unlikely at this gap size). This second peak only appears when a polymerase is present, and the current distribution is quite different from that measured through streptavidin alone at a smaller gap size. As observed for other proteins, these distributions change very little with gap size until contact with the protein is lost. FIG. 14D shows the conductance distribution measured for a Gen II with thiolated streptavidin on the surface but with a bare (unfunctionalized) probe. The 3 nS peak observed in FIG. 14B is now absent. Taken together, these experiments show that an additional high conductance feature occurs in the conductance distribution when (a) the polymerase has two biotinylated contacts and (b) streptavidin is present on both the probe and substrate. Therefore, this highest conductance peak is attributed to biotin-mediated binding events that bridge the electrode gap.

Figures 19A, 19B, 19C, 19D:
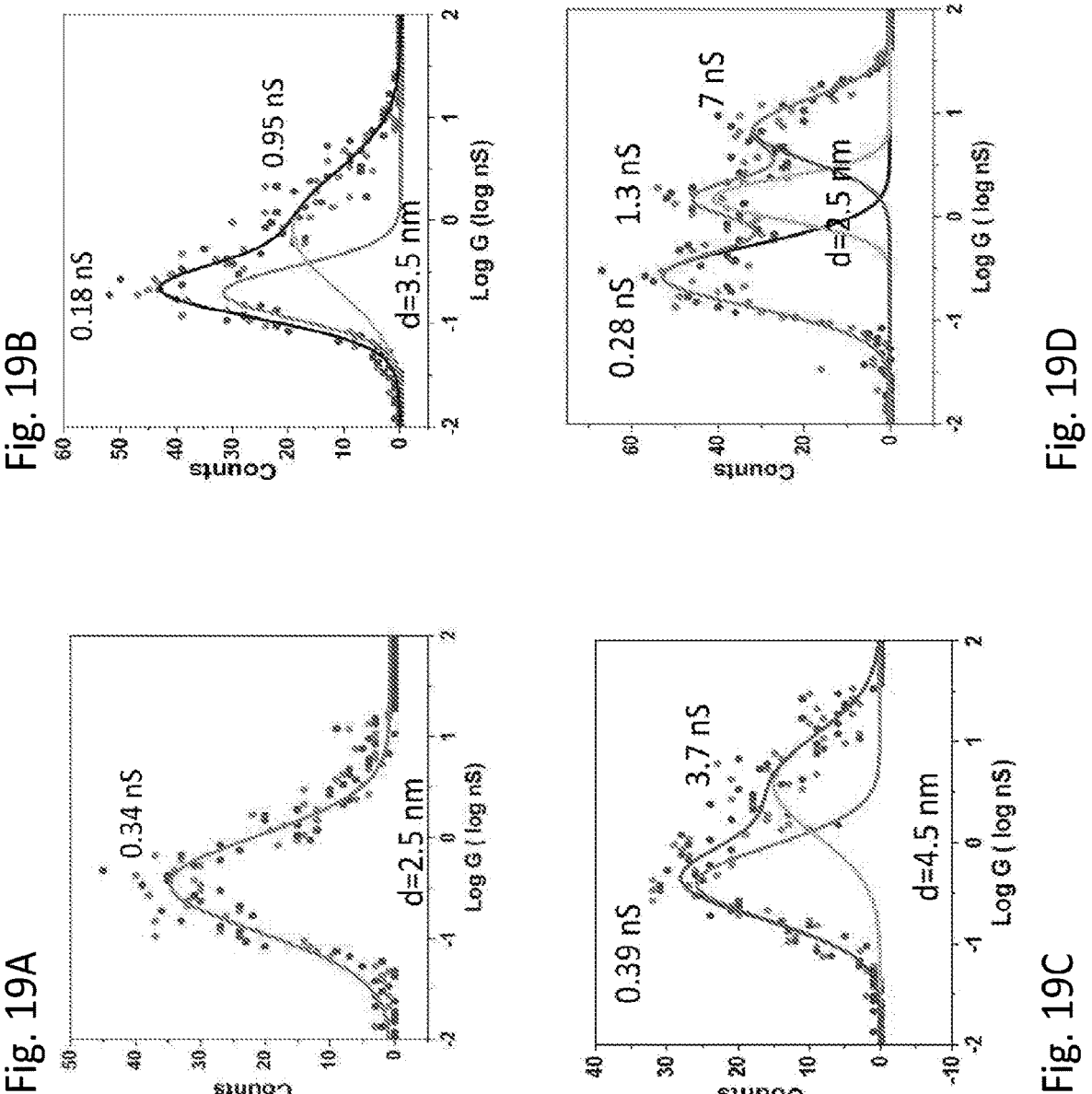
FIGS. 19A-19D illustrate effects of biotin binding on the conductance of streptavidin.
Figures 20A, 20B:
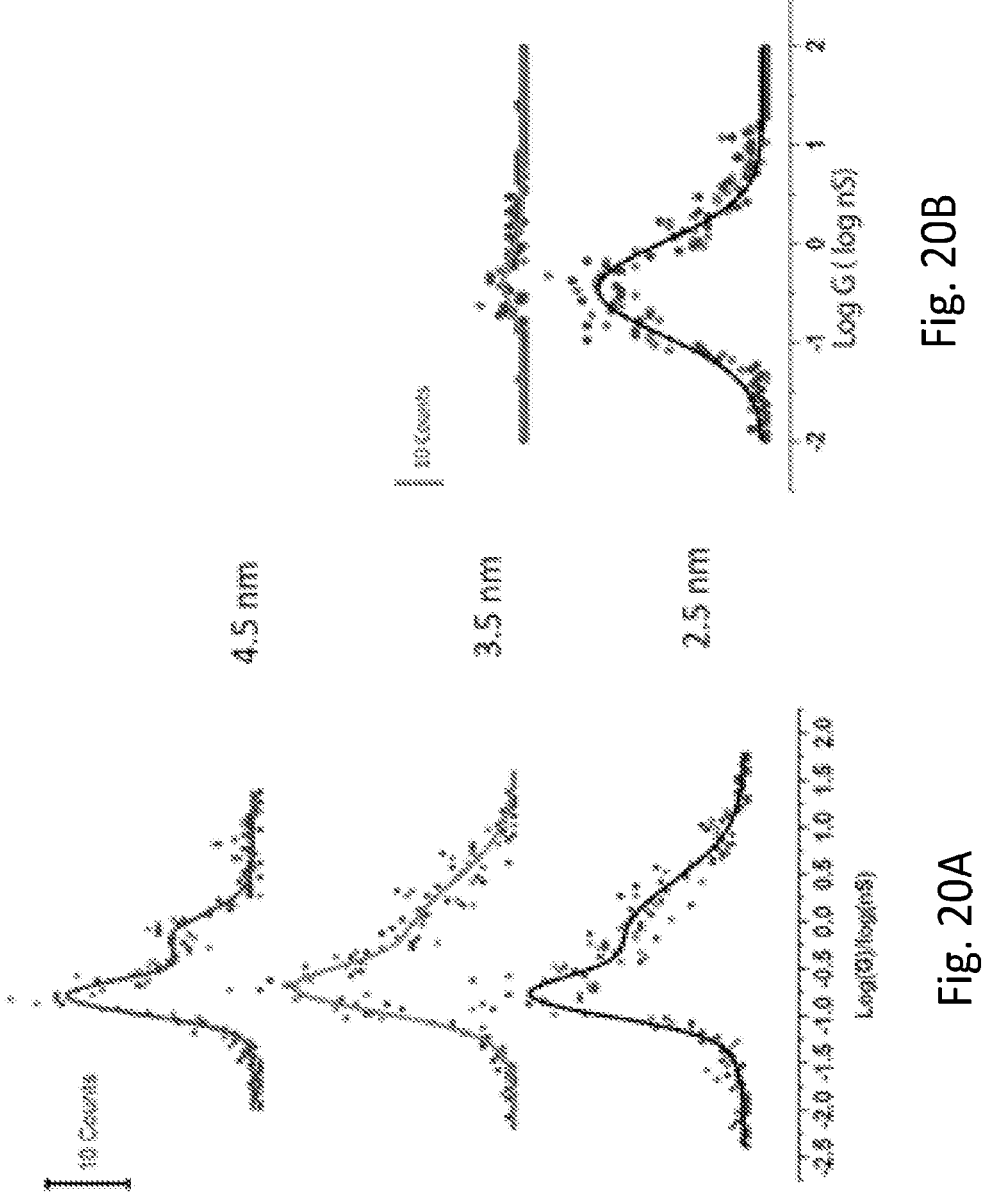
FIGS. 20A and 20B illustrate conductance distributions for Φ29 and streptavidin.

FIG. 14C shows a conductance histogram for a Gen III polymerase, using a thiolated biotin molecule to attach Streptavidin to the electrode surface. The highest conductance feature has moved out to 5.6 nS. This is a consequence of the biotin-mediated attachment of the streptavidin to the electrodes. FIGS. 19A-19C show conductance distributions for the Gen III polymerase as connected by thiolated streptavidin (19C—larger peak=3.7 nS), or wild type (WT) streptavidin bound to biotinylated electrodes (19D—peak 3=7 nS) showing the increase in conductance when a specific ligand is used for a contact. In addition, it is concluded that the introduction of the additional flexible linker has reduced the overall conductance of the complex a little for a given coupling chemistry (5.6 nS for Gen III— FIG. 14C, vs 7 nS for Gen II— FIG. 19D—with biotin mediated coupling to the electrodes in both cases). These data demonstrate the successful engineering of a bis-functionalized polymerase that retains polymerase activity while showing increased electrical conductivity.

Figure 15B:
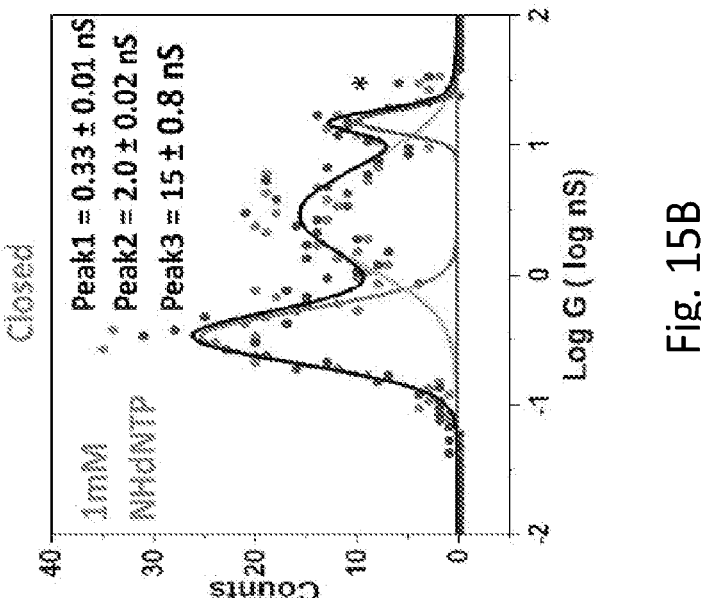
FIGS. 15A-15B shows closed (15A) to open (15B) tran-sition changes polymerase conductance.
Figure 15A:
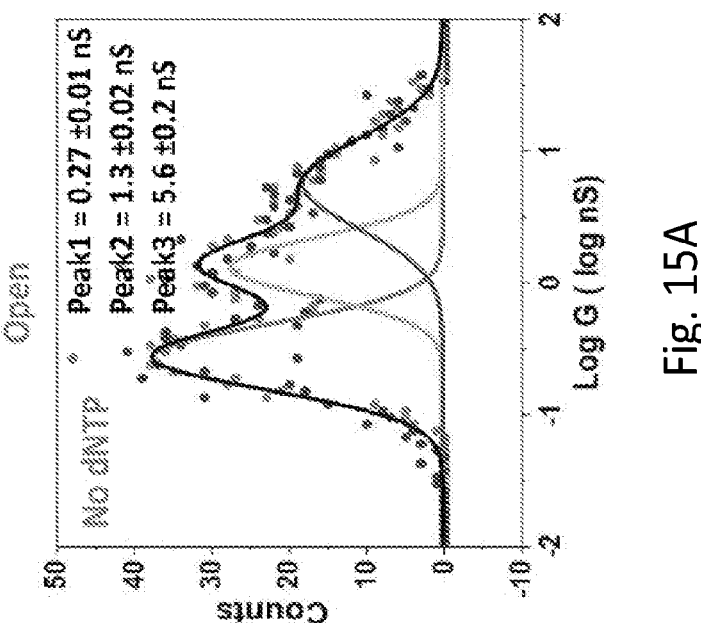

The conformational sensitivity of the electronic signals was next evaluated. It was shown earlier that ligand binding changes the conductance distribution of a streptavidin molecule significantly: is the same true of a polymerase? In order to probe this, a Gen III polymerase was generated to be stabilized in the closed form by incubating a template-bound polymerase with nonhydrolzable nucleotide triphosphates (NH-dNTPs). The NH-dNTP binds the template-polymerase complex, closing the polymerase, which then remains in the closed configuration because of the non-hydrolyzable triphosphate. Conductance distributions for the normal, open (–dNTP) and closed (+NHdNTP) forms are shown in FIGS. 15A and 15B. There is a very large change in the highest conductance feature (from 5.6 to approximately 15 nS).

Figure 21:
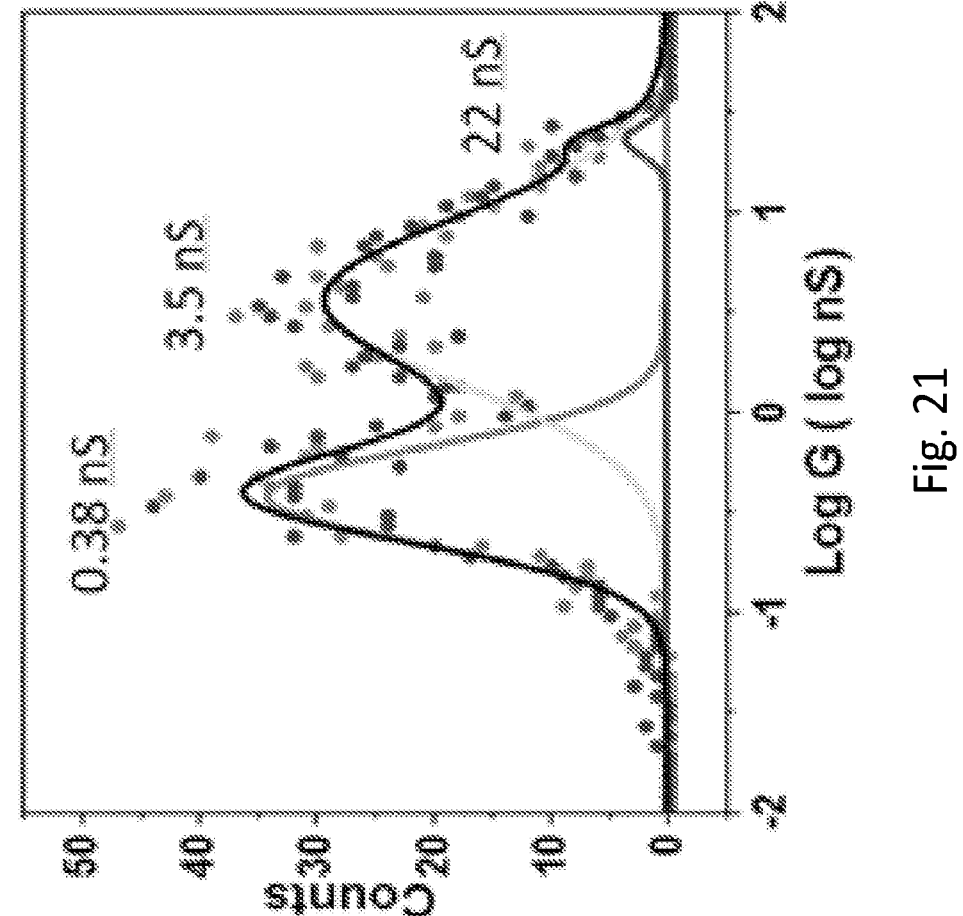
FIG. 21 illustrates a repeated measurement of the conductance distribution for Φ29 in the closed form.
Figure 22:
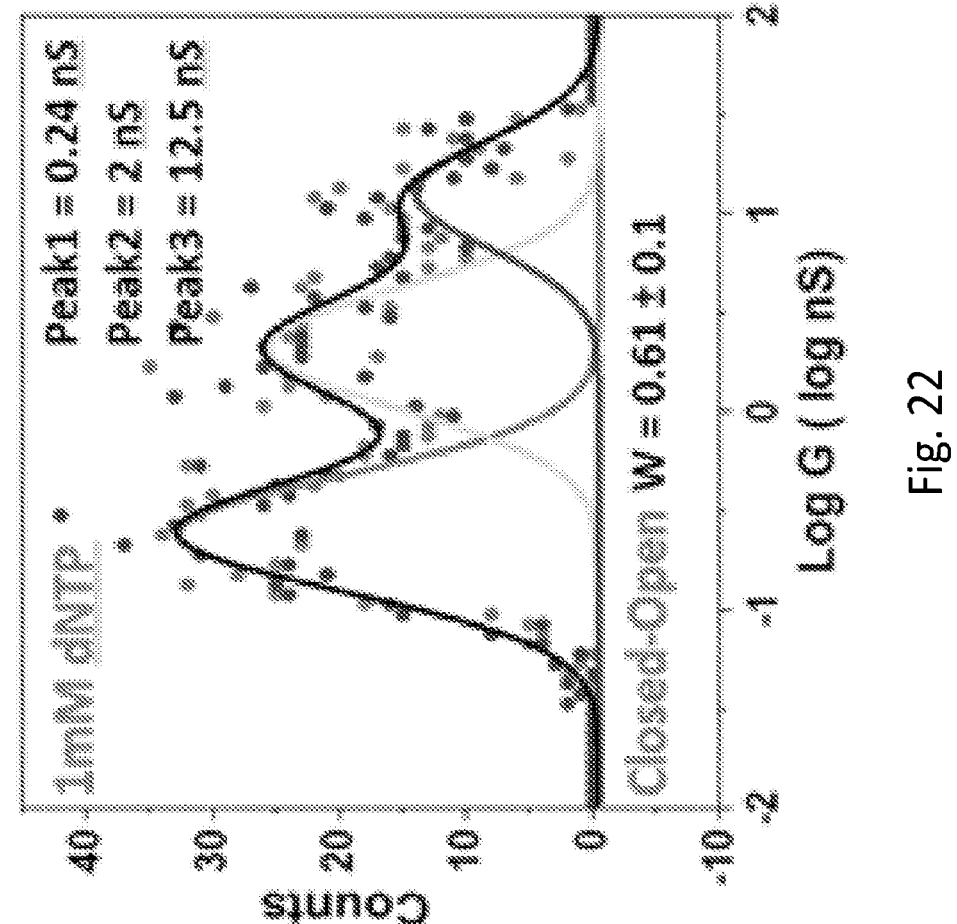
FIG. 22 illustrates conductance distributions for an active polymerase.
Figure 23:
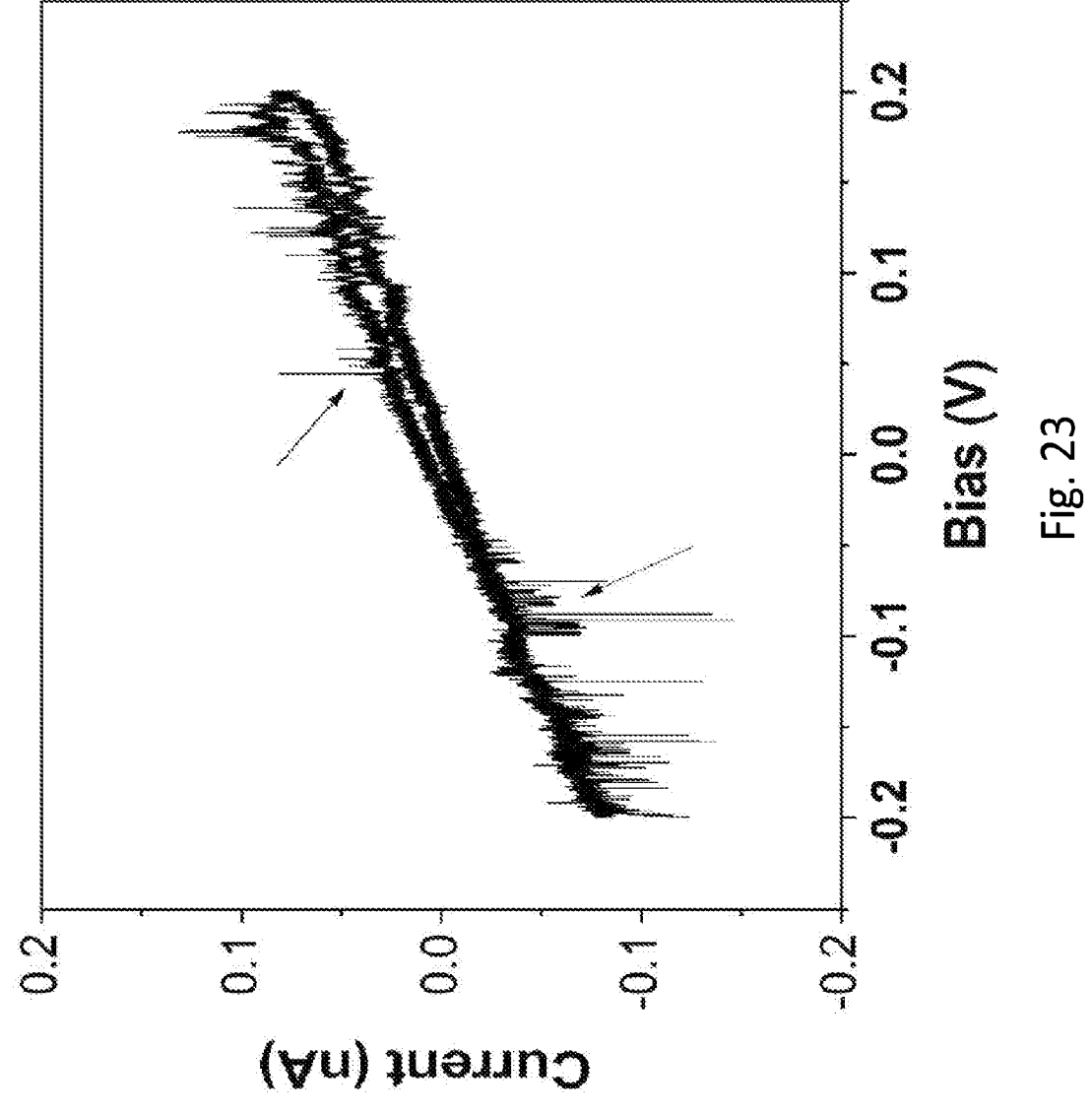
FIG. 23 provides a current-voltage curve for an active polymerase.

The highest conductance feature is quite small, so the experiment was repeated to verify its existence (FIG. 21). Interestingly, IV curves taken on the active form (using normal dNTPs) yield an intermediate conductance (FIG. 22), implying that an active polymerase may stay in a high conductance state for long enough to yield increased conductance in an IV measurement (which takes 0.4 s). Taken together, these measurements indicate that the conductance distribution is affected by the conformation of the polymerase. One interesting consequence of measuring IV curves on an active enzyme (as in FIG. 22) is that noise now appears on the curves in the usually quiet region below 100 mV (FIG. 23).

Figures 16A, 16B, 16C, 16D, 16E, 16F:
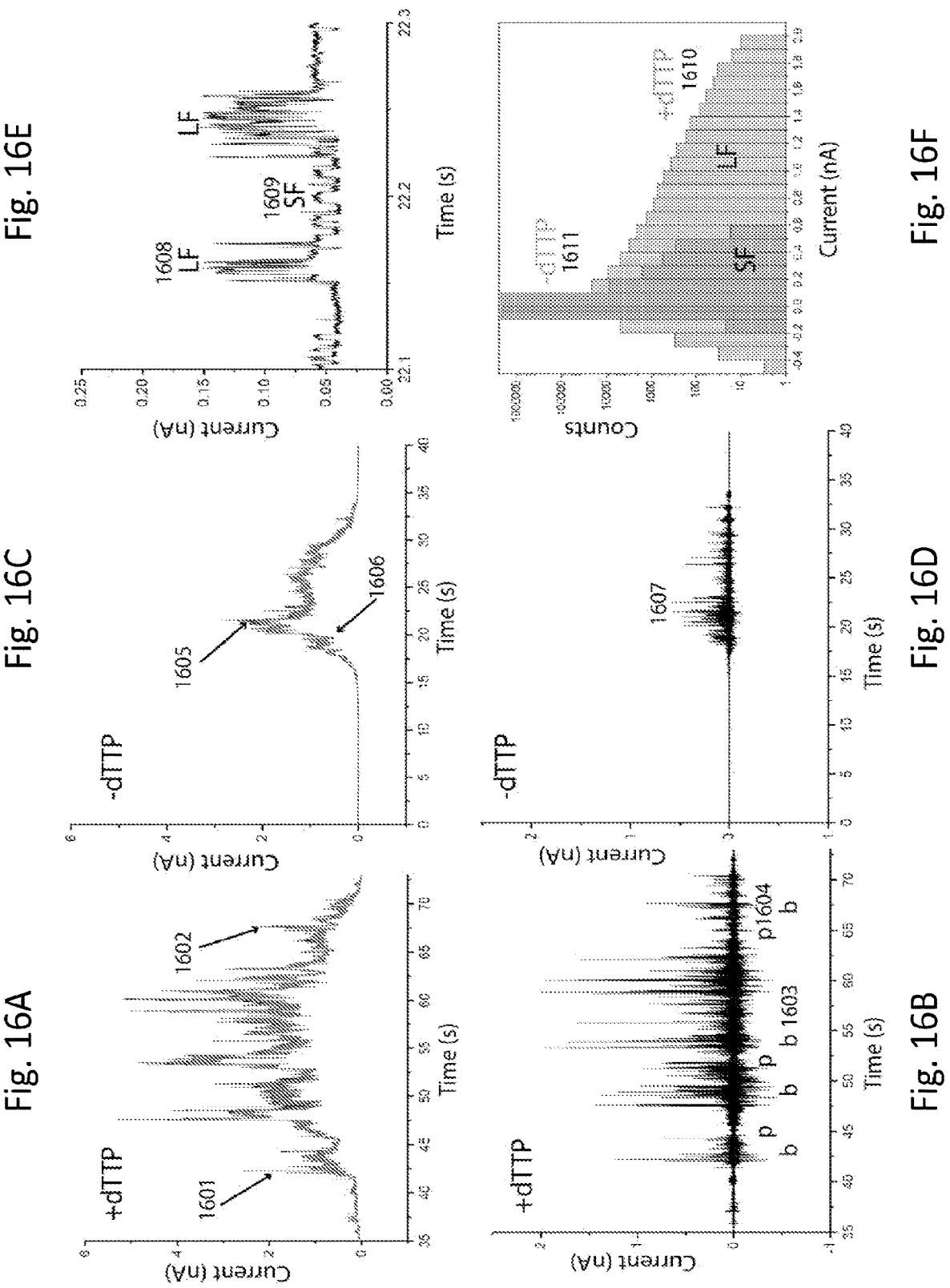
FIGS. 16A-16F show characterizing the signals generated when polymerase is activated.

Taken together, these observations indicate that it may be possible to observe signs of polymerase activity in a recording of current taken over time (I(t)), as the polymerase incorporates incoming nucleotides. I(t) was recorded at a constant 50 mV bias (below the threshold for contact noise) for a single stranded template primed by a 15 base pair hairpin (Methods). To do this, the same procedure outline above was followed for obtaining IV curves, but holding the bias constant, and recording current for 90 s before withdrawing the probe and reestablishing servo control. A gap of 2.5 nm under servo control was started with, increasing the gap to 6 nm, and then brought the tip down to 4.5 nm and then recorded current for 60 s. Typically, no current was recorded for the first 10-20 s, after which a contact formed and an I(t) curve was obtained. Contacts were formed with molecules in >50% of these "fishing" attempts. The currents jumped suddenly on contact with the molecule, but then changes substantially as the contact point drifts. A typical current-time trace is shown in FIG. 16A. By comparing the distribution of currents measured in current-time traces with the conductance distributions obtained from many repeated contacts with the molecule, we have shown that the variation in the current-time trace can be accounted for by variations in the contact point.

Noise Analysis

Figures 24A, 24B:
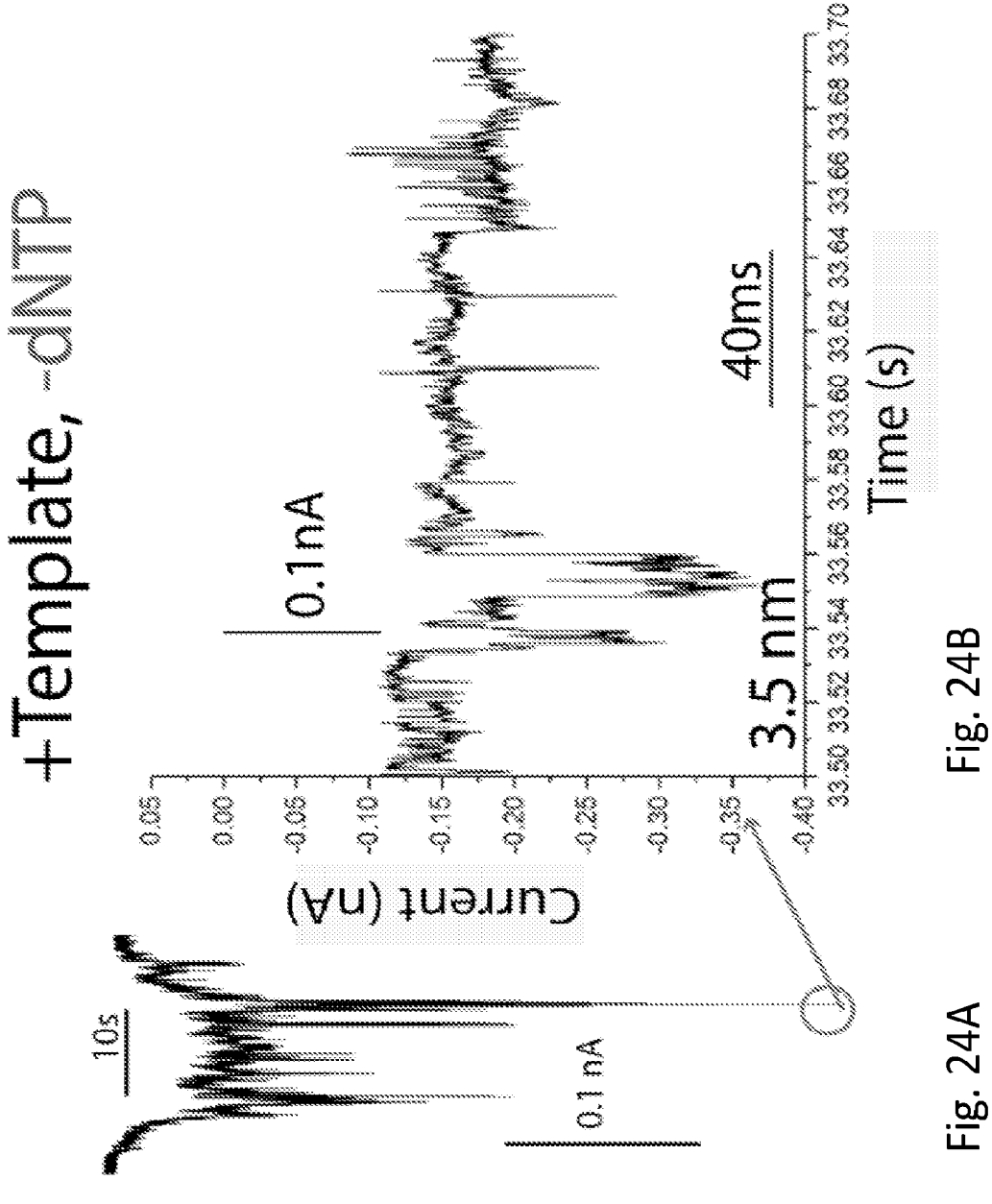
FIGS. 24A-24E illustrate signals obtained from a mono-biotinylated polymerase. Noise signals obtained with the Gen I monobiotinylated polymerase.
Figures 24C, 24D:
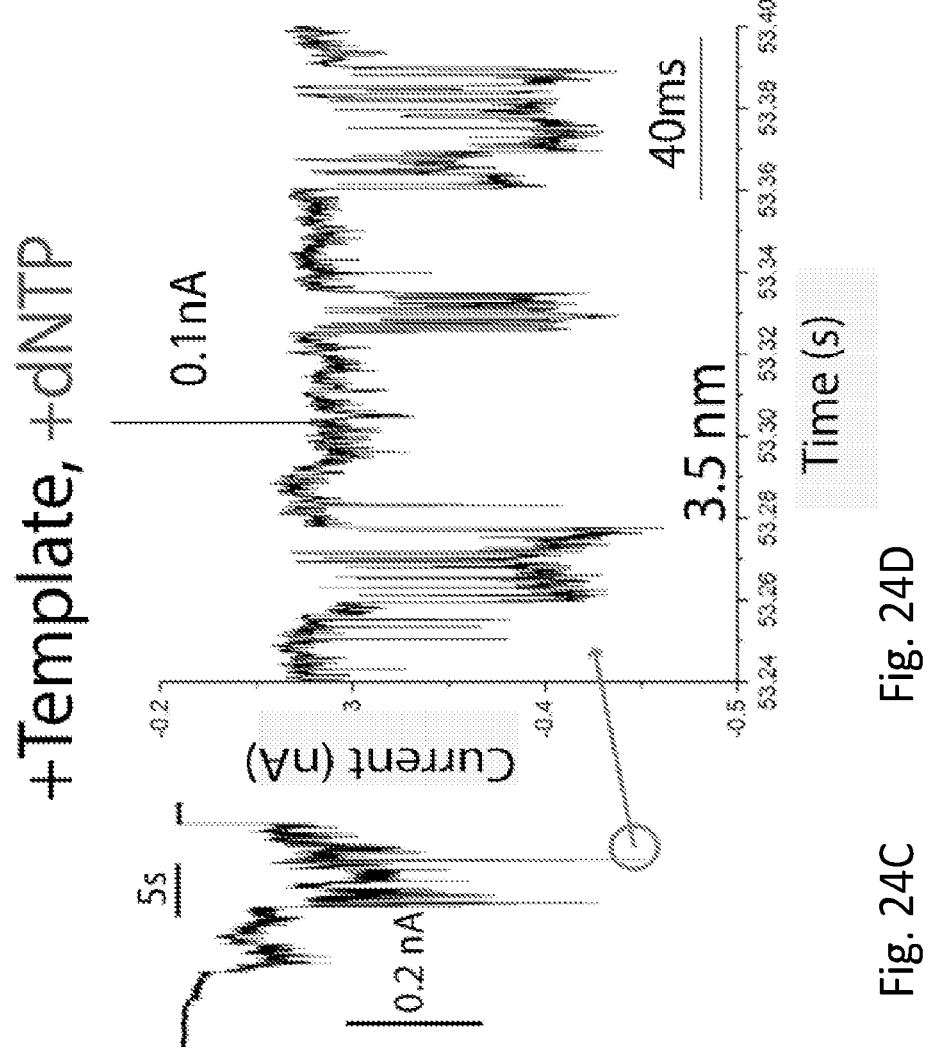
Figure 24E:
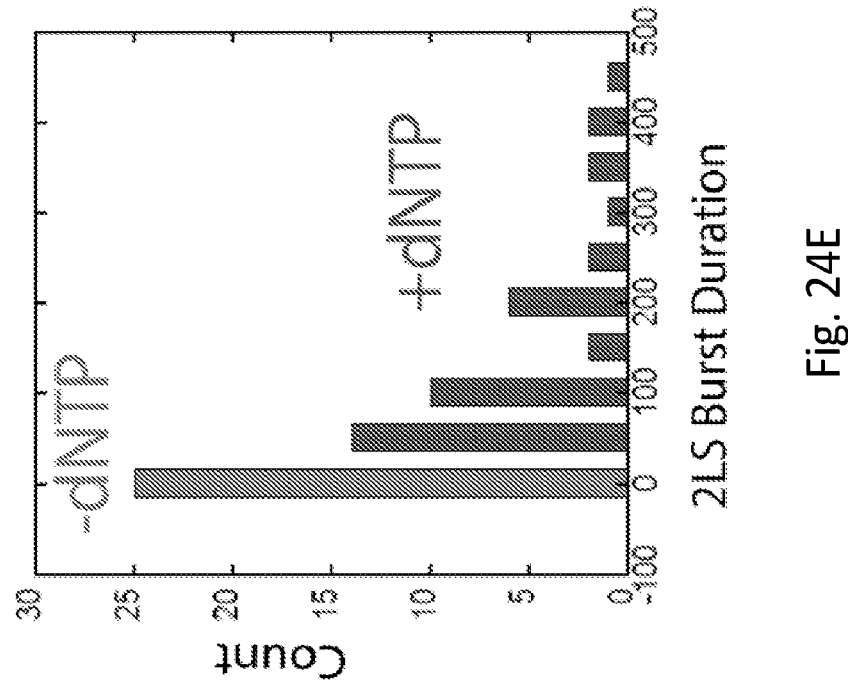

The Gen I polymerase with a single contact was first studied. Bursts of noise were clearly visible when the polymerase was activated on addition of the complementary dNTPs (FIG. 24A). However, currents were generally low (c.f., the conductance distribution in FIG. 14A) as were the signal levels. It was for this reason that we constructed the bis-functionalized polymerases that yield the higher conductance features seen in FIGS. 14B and 14C. FIG. 16A shows a typical I(t) trace for an d(A)$_{10}$ single stranded template in the presence of all four dNTPs (black trace, mainly obscured by the overlaid red trace) in the polymerization buffer (Methods). Large changes in the background current obscure the fluctuations, so the background was removed using an asymmetric least squares (ALS) fit. The ALS accurately follows the background without distorting the noise signals (FIGS. 25A-25D). (Attempts to remove the background with a median filter distorted the noise signals.) The ALS fit to the raw data is superimposed on it in FIG. 16A. The flattened noise trace, obtained by subtracting the ALS fit from the raw data, is shown in FIG. 16B. The noise signals are quite large, in excess of a nA in this case, and occur in bursts with pauses in between them, though no discernable repeat pattern was found. A control signal of similar overall DC conductance was selected (FIG. 16C), taken in a buffer containing only dATP, dCTP and dGTP, lacking the necessary dTTP. Following the same subtraction procedure outlined for the active molecule, a noise trace is obtained, as shown in FIG. 16D. The result is clearly not random noise, because it coincides exactly with the period for which the molecule is contacted. The same behavior was seen in eight other control experiments. So clearly, both active and inactive polymerases produce electrical noise. Given the variable background signal and the stochastic nature of the fluctuations, can we distinguish active from inactive polymerase? Inspection of the details of the noise signals at a higher time resolution offers a clue. FIG. 16E shows a trace containing both large (LF) and small (SF) fluctuations. If the size of the fluctuations were compared from the control experiment (–dTTP) with the size distribution of the fluctuations for the active polymerase (+dTTP) (measured at about the same background current), the current fluctuations in the active polymerase are much larger (FIG. 16F). The runs of similar background current were compared, because inspection of many traces indicates that the size of the current fluctuations increases with the background current.

Figures 17A, 17B, 17C, 17D:
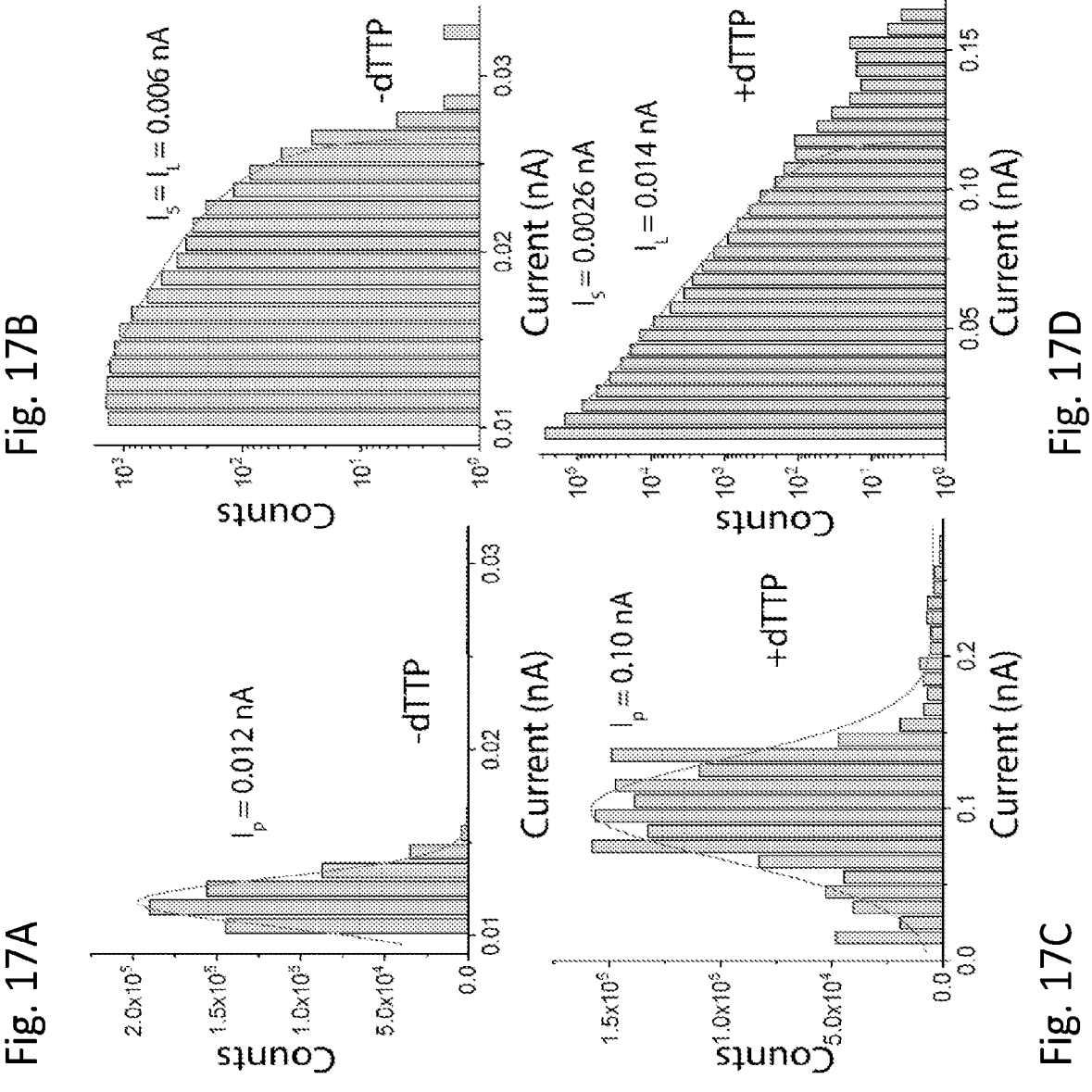
FIGS. 17A-17E show small and large fluctuations defined in terms of baseline current. Larger signals are obtained with the higher-conductance contacts. To quantify this, the base-line levels in a given run are quantified by fitting a Gaussian model to the distribution of measured currents, characterized by Gaussian peak current, $I_P$(FIG. 17A, 17C). A two expo-nential fit ($I_S$, $I_L$) is used to model the distribution of noise signal amplitudes. When the complementary base is absent (FIG. 17B) the fit converges to one value, $I_S$=$I_L$ in all cases.
Figure 17E:
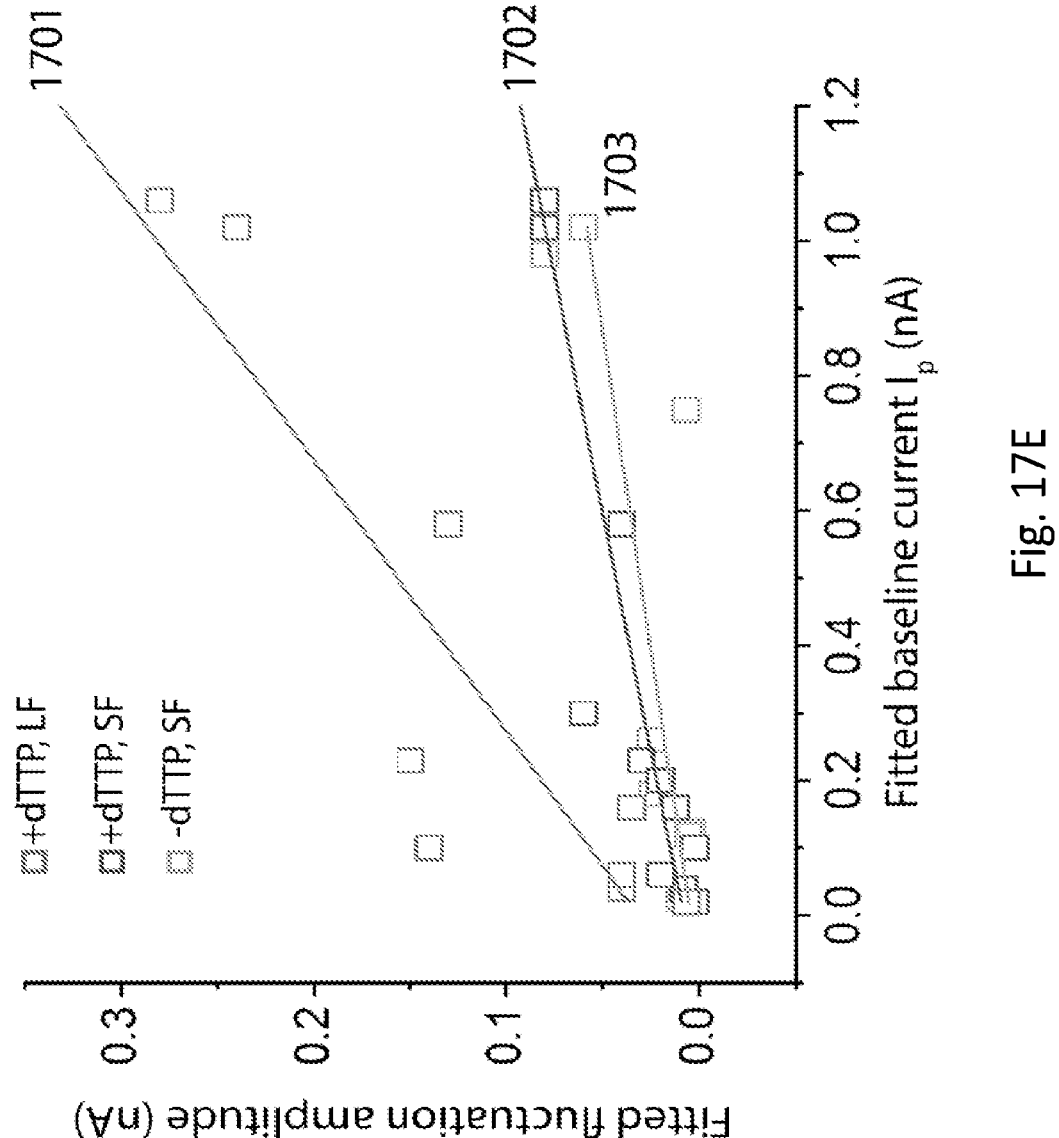

In order to quantify the relationship between the size of the fluctuations and the background current, the distributions of both were studied for a number of molecules with, and without dTTP present in the buffer solution. For each molecule, the ALS fitted baseline currents were binned as shown by the examples in FIGS. 17A, 17C. Many of these distributions could be fitted by a Gaussian. However, some could not—for example, the background can jump between two or three levels. In these cases, the largest peak that was clear of the background was fitted. The peak of the fitted Gaussian, I$_p$, was then used to characterize the baseline for that run. Example of the binned noise signals are given in in FIGS. 17B, 17D. To characterize these a double exponential distribution was used:

$$N(i) = A_1\exp\left(-\frac{i}{i_S}\right) + A_2\exp\left(-\frac{i}{i_L}\right)$$

where i is the current in a given bin of the histogramed current distribution. In the case of the experiments in which dTTP was withheld (e.g., FIG. 17B), the fits all converged to a single exponential (i$_s$=i$_L$). For recordings with dTTP present, most of the fits converged on the double exponential distribution with i$_s$<i$_L$ (4 of 13 molecules showed the small peaks only). The results are summarized in FIG. 17E.

Activated molecules (+dTTP) showed both large and small fluctuations. The controls (−dTTP) showed only small fluctuations, essentially equal to the small fluctuations also seen in the active polymerases. There is an approximately linear relation between background current and fluctuation amplitude as shown by the three linear fits. For the large fluctuations, characteristic of active polymerases, $i_L=(0.25\pm0.026)$ $i_p$ (i is the 1/e value of the fit, so larger and smaller spikes are observed also). For the small fluctuations, present in both active an inactive polymerases, $i_s=(0.06\pm0.01)i_p$. Thus, the active state can be identified by the presence of fluctuations that are about 25% of the baseline current, while fluctuations in the inactive state are about 10% of the baseline current. Not all polymerase molecules contacted were active as indicated by the lack of large fluctuations in 4 of the 13 molecules studied. On the other hand, none of the eight −dTTP control runs showed large fluctuations (Table 1).

Figures 28A, 28B:
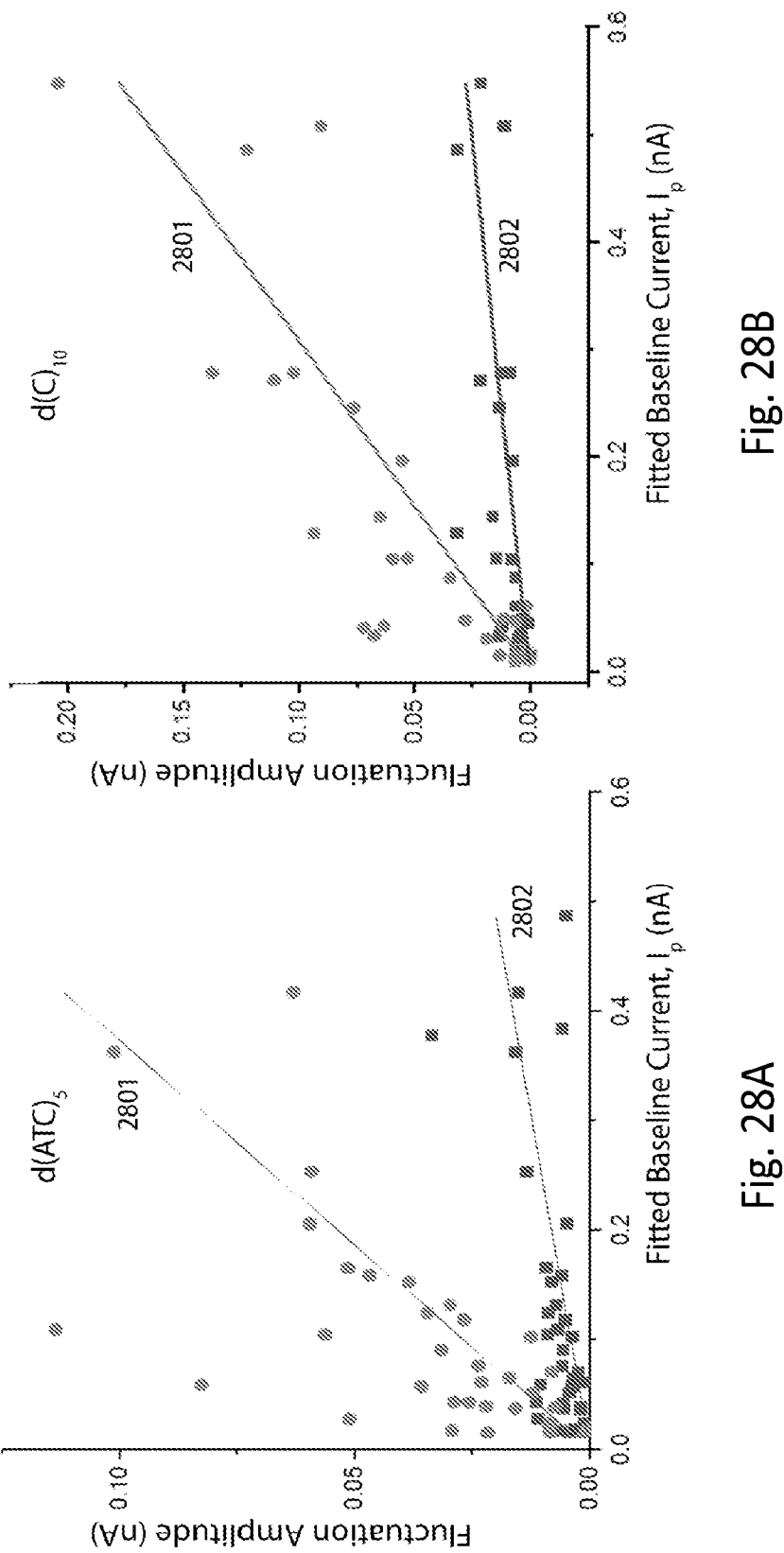
FIGS. 28A and 28B illustrate fluctuations for active and inactive polymerases. Values of $I_L$ (2801) and $I_S$ (2802) plotted vs the associated value of baseline current ($I_P$) for 38Φ29 molecules actively transcribing the $d(ATC)_5$ template FIG. 28A and for 25 molecules transcribing $d(C)_{10}$ (FIG. 28B). The analysis follows that presented in FIGS. 17A-17E for $d(A)_{10}$. Lines are linear fits yielding $i_L$=0.27 (±0.03)$I_p$ and $i_S$=0.04(±0.01)$I_p$ for $d(ATC)_5$ and $i_L$=0.32 (±0.03)$I_p$ and $i_S$=0.05(±0.007)$I_p$ for $d(C)_{10}$.

This analysis was repeated using data obtained in 38 runs in which $d(ATC)_5$ was used as the template, with the results shown in FIGS. 28A-28B. The fitted amplitude distributions for the large fluctuations (LF) show considerable variation, but the trends observed for $d(A)_{10}$ (FIGS. 17A-17E) are reproduced well with $i_L=0.27(\pm0.03)I_p$ and $i_s=0.04(\pm0.01)I_p$ for the small amplitudes.

In order to confirm the association of large fluctuations (by which we now mean 25%, or more, of the baseline current) with polymerase activity experiments were carried out with different templates in different conditions. In each case, the DNA template consisted of a 15 base double-stranded region connected by a 9 base loop with the ssDNA template extending from the 5' end of the hairpin. The ssDNA templates were $(dA)_{10}$, $(dC)_{10}$, $(dA)_{10}(dC)_{10}$ and $(dTAC)_5$. Positive experiments were carried out in the reaction buffer (1 mM phosphate buffer, pH=7.4, 4 mM TCEP, 10 mM $MgCl_2$ with 1 mM dNTPs and 1 µM template). In the control experiments, one critical ingredient was withheld as listed below in Table 1 (where they are labeled as control, C). In addition, measurements were carried out using nonhydrolyzable dNTPs. Each of the runs was analyzed as described above for $(dA)_{10}\pm$dTTP.

TABLE 1

Occurrence of large fluctuations (fraction of measured molecules) for various experimental conditions. NH = non-hydrolyzable dNTPs. Large fluctuations are identified by a machine fit converging on a two component distribution of fluctuations.

| Experimental Conditions | Control/ Active | Fraction Large Fluctuations |
|---|---|---|
| $(dA)_{10}$ +dNTPs +$Mg^{2+}$ | A | 0.69 |
| $(dA)_{10}$ +dATP, +dCTP, +dGTP, −dTTP, +$Mg^{2+}$ | C | 0 |
| $(dC)_{10}$ +dNTPs +$Mg^{2+}$ | A | 0.52 |
| $(dA)_{10}(dC)_{10}$ +dNTPs +$Mg^{2+}$ | A | 0.44 |
| $(dATC)_5$ +dNTPs +$Mg^{2+}$ | A | 0.52 |
| $(dA)_{10}(dC)_{10}$ −dNTPs +$Mg^{2+}$ | C | 0 |
| $(dA)_{10}(dC)_{10}$ +dNTPs −$Mg^{2+}$ | C | 0 |
| $(dA)_{10}(dC)_{10}$ +dTTP −dGTP, +$Mg^{2+}$ | C | 0.32 |
| $(dA)_{10}(dC)_{10}$ NH-dNTPs +$Mg^{2+}$ | C | 0 |
| No template +dNTPs +$Mg^{2+}$ | C | 0 |

Figures 26A, 26B:
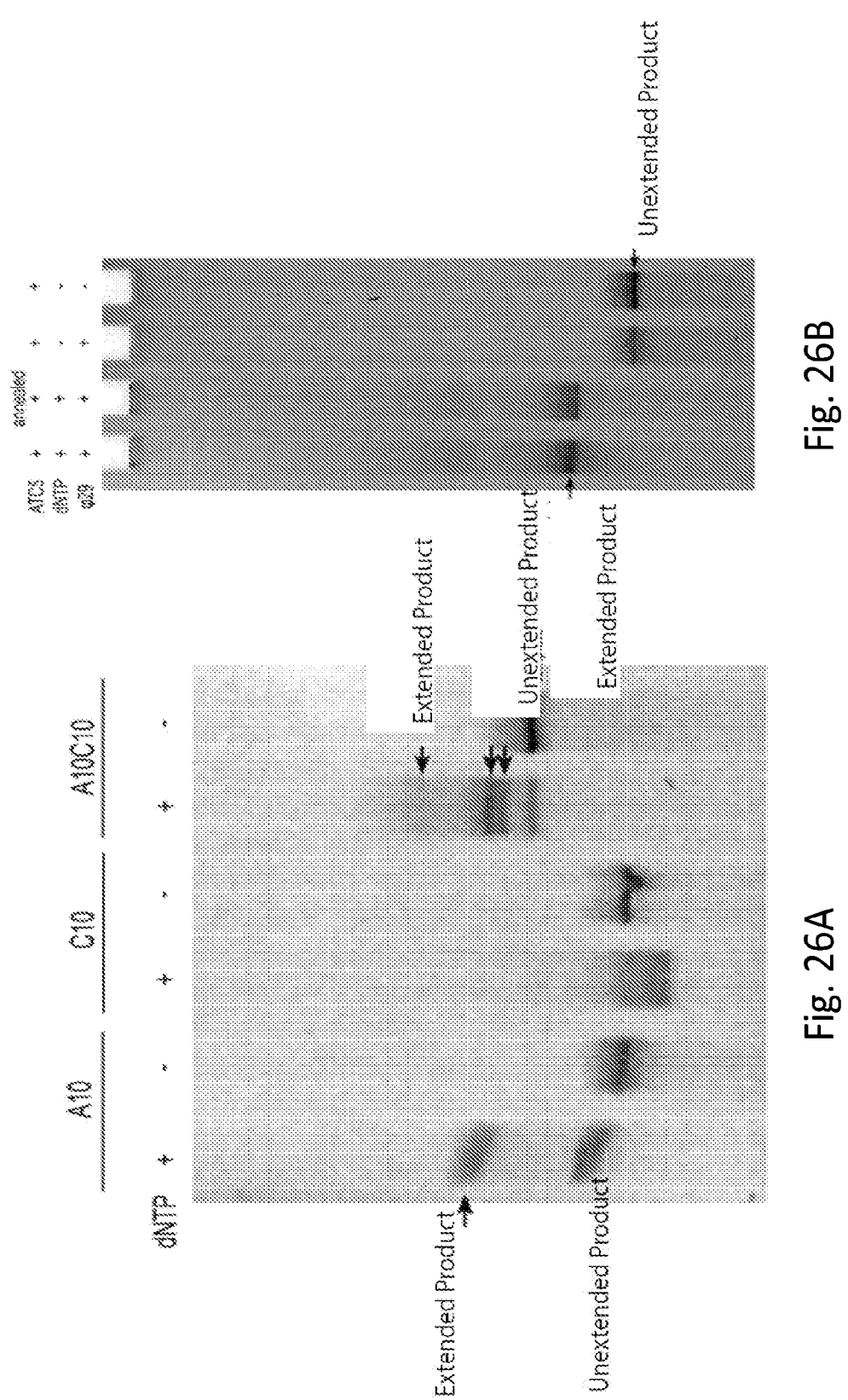
FIGS. 26A and 26B show homopolymer templates fail to extend fully. In particular.
Figures 27A, 27B:
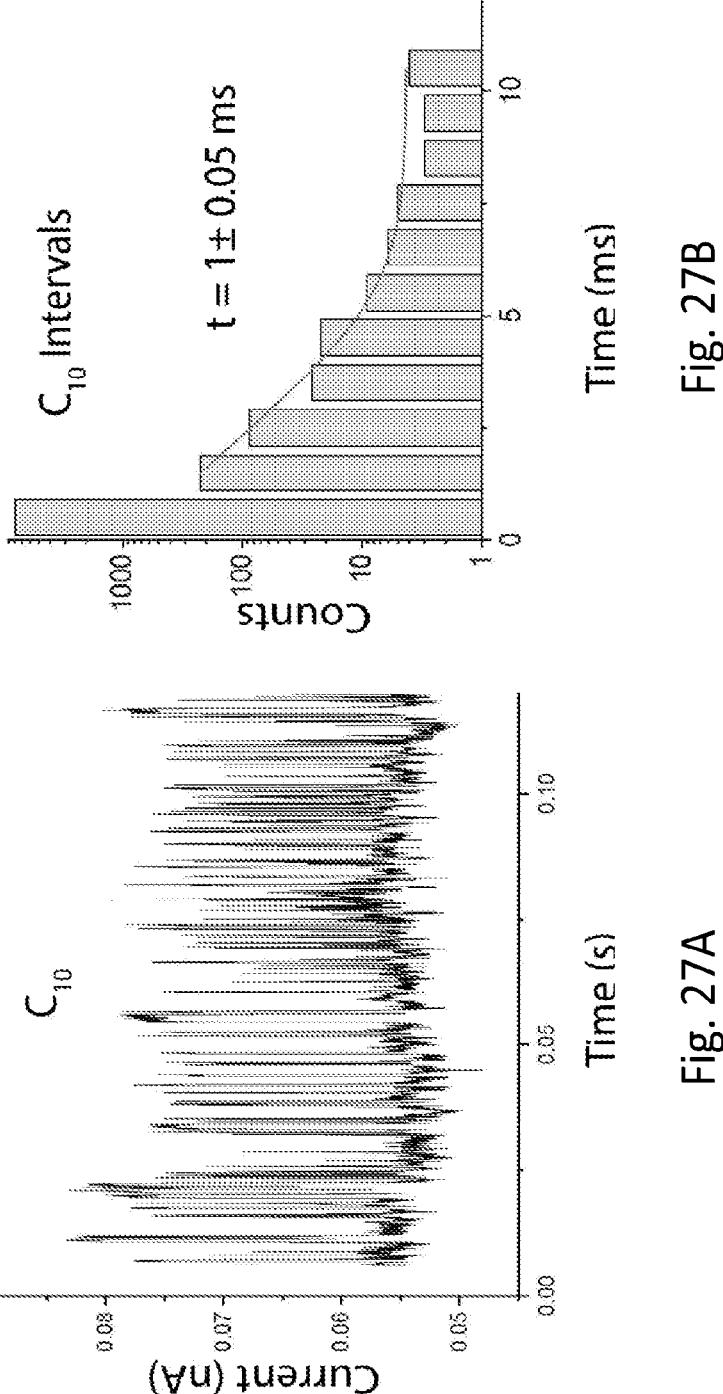
FIGS. 27A-27C show how noise signals from $d(C)_{10}$ are dense despite incomplete polymerization.
Figure 27C:
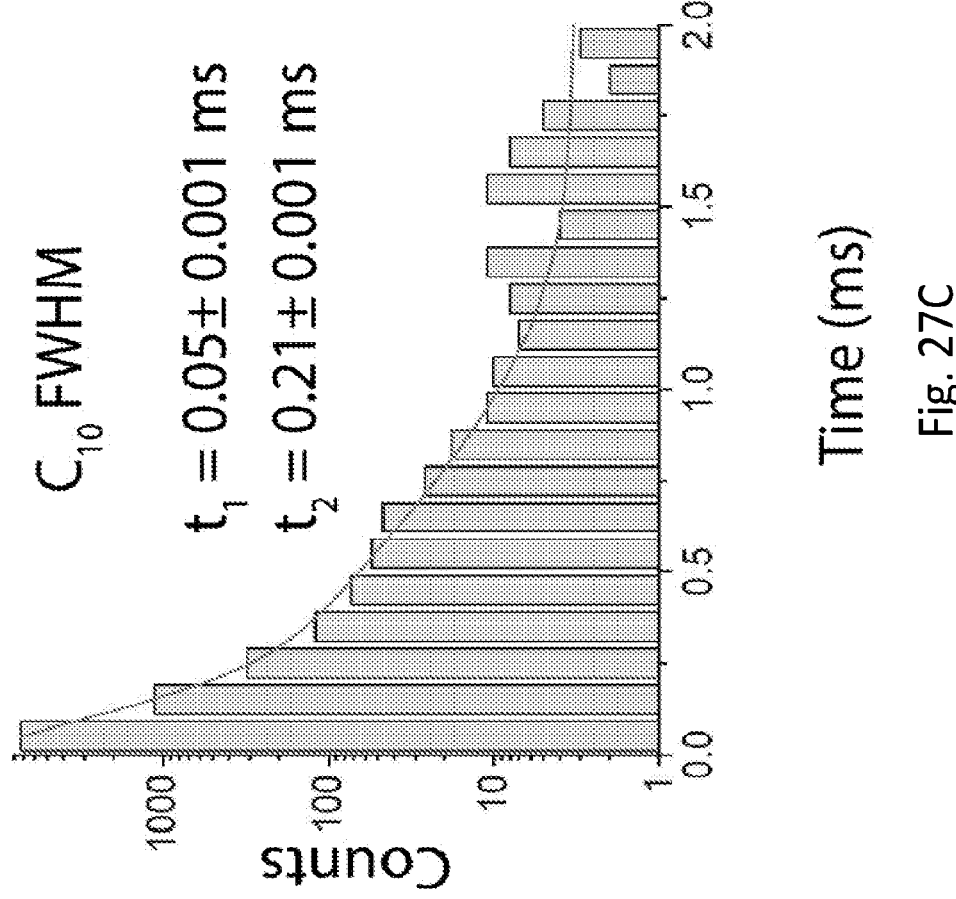

Withholding any one of the ingredients critical to polymerase function appears to abolish the large fluctuations. An interesting exception was $(dA)_{10}(dC)_{10}$ in the presence of dTTP only. One expects that the polymerase would reach the end of the A tract and then stall for want of the missing dGTP nucleotide, but that is not the case. In order to investigate the behavior of the polymerase further, denaturing gels of the polymerization reaction for all four templates were run. Because the primer is terminated in a hairpin, the denatured polymerization product produces a higher molecular weight feature on the gel, with no feature at the molecular weight of the primer if the reaction goes to completion. The results are seen in FIGS. 26A and 26B. Though single-stranded homopolymers have been used for studies of a different polymerase motion previously it is known that polymerases tend to stall as they encounter secondary structure in a single-stranded DNA template. The gels show that the only template that is fully extended is $d(ATC)_5$. $d(A)_{10}$ is fully extended in a significant fraction of events. $d(C)_{10}$ does not appear to be extended at all, which is quite surprising because the noise signals from this template are quite dense (FIGS. 27A-27C). The $d(A)_{10}d(C)_{10}$ is extended in a fraction of cases, but only to the end of the A tract. Thus, it is likely that the polymerase falls off this template, allowing for polymerization to start again in the presence dTTP only, accounting for the observation of activity in the absence of dGTP (Table 1). Longer pauses are observed in this experiment as might be consistent with the polymerase falling off and having to bind a new template.

Figures 18A, 18B, 18C, 18D:
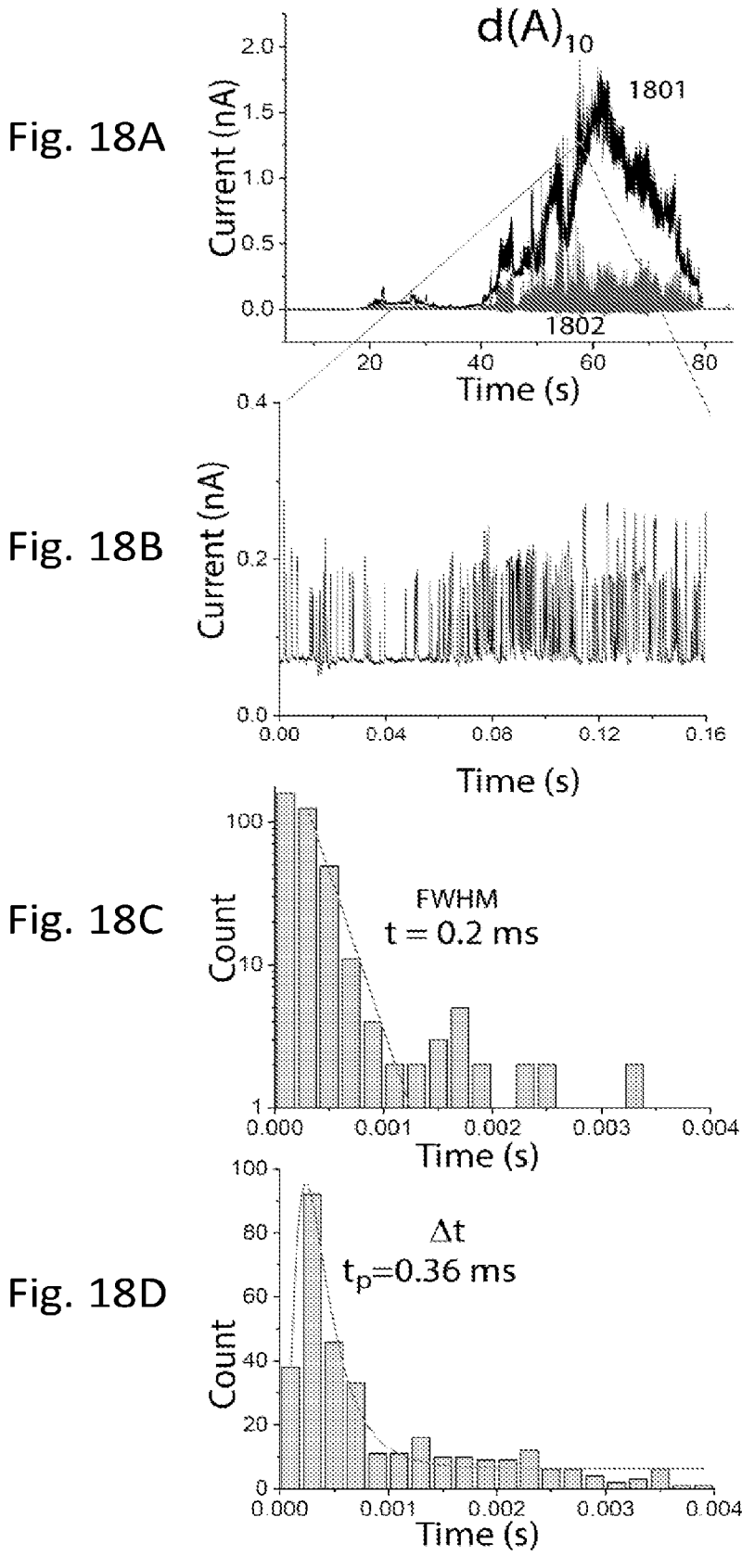
FIGS. 18A-18H illustrate comparing noise characteristics from two sequences. Representative raw (1801) and background subtracted signals (1802) for $d(A)_{10}$ (FIG. 18A) and $d(ATC)_5$ (FIG. 18E). 160 ms samples of noise are shown in (FIG. 18B) and (FIG. 18F). These are raw data selected for having a constant background current. They illustrate the "25% rule" approximately, though small fluctuations appear to be absent in the run of $d(ATC)_5$ data shown.
Figures 18E, 18F, 18G, 18H:
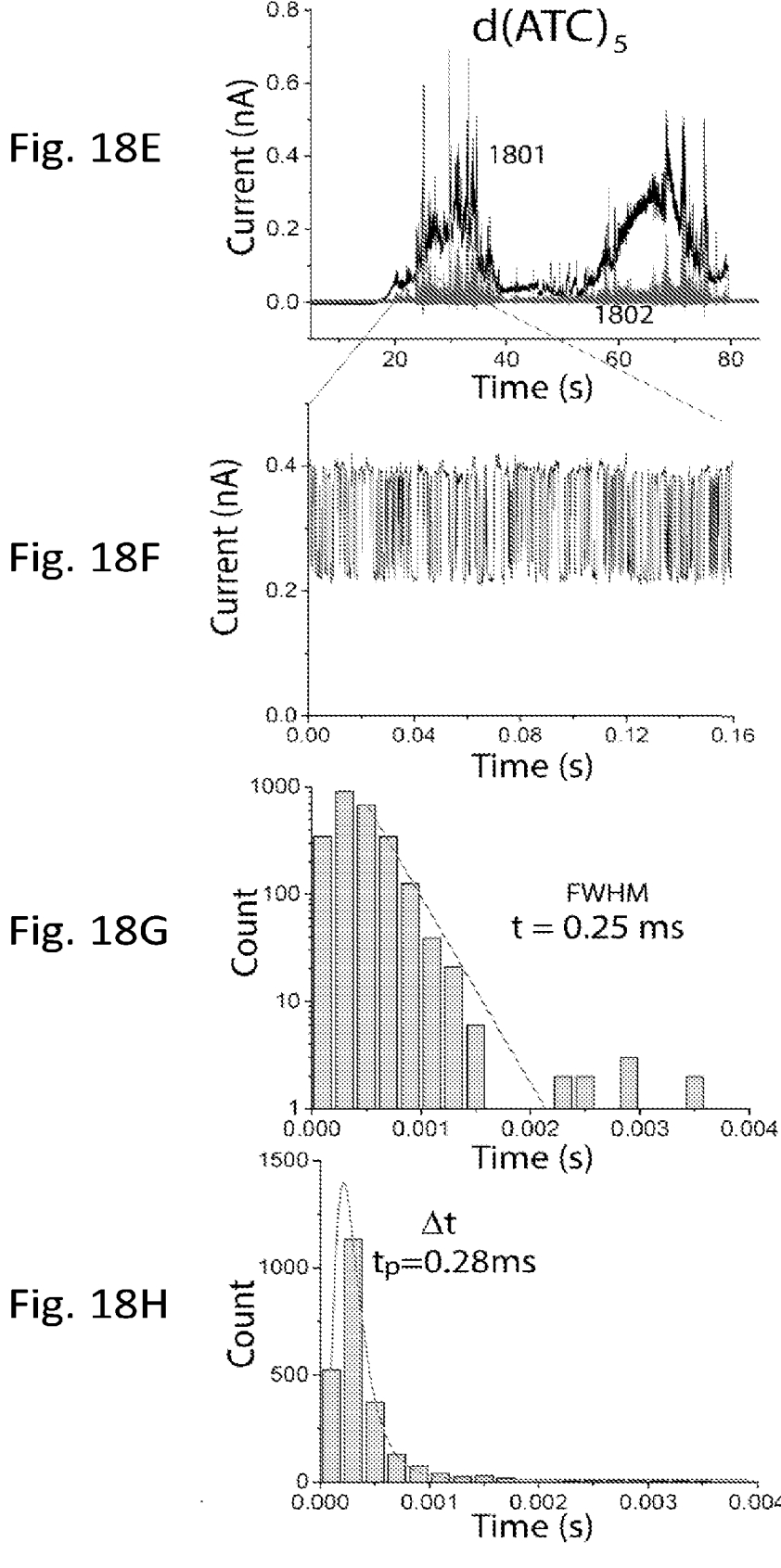

The details of the noise for two different sequences were studied to investigate whether any of the noise features changed as the template sequence was changed. Homopolymer templates could not be compared because of the poor activity of the enzyme on C tracts, so we have compared $d(A)_{10}$ and $d(ATC)_5$. FIG. 18A shows raw data for $d(A)_{10}$ (a) and $d(ATC)_5$ (e) with the extracted noise signature plotted below. Although the flattening algorithm does not distort the signal significantly, the amplitude of fluctuations is affected by changes in the baseline current, as discussed above. For this reason, regions where the baseline was constant and the noise signal is dense were looked for. Two representative samples are shown in FIGS. 18B and 18F. The difference in these noise signals is noticeable. All of the runs like this in the A or C homopolymers had significant amplitude fluctuations. Since the baseline current (and therefore the contact) was constant in the regions examined, these fluctuations reflect the behavior of the polymerase. On the other hand, the ATC polymer signals have many regions where the fluctuation amplitude (at constant baseline current) was constant, for times of up to 0.5 s, the longest constant baseline signal obtained. This difference may be related to the difference in processivity observed in the biochemical measurements (FIGS. 26A and 26B). It is striking that signals obtained from the $d(C)_{10}$ template are similar to those from $d(A)_{10}$ (FIGS. 27A-27C) despite the fact that $d(C)_{10}$ is barely extended. So the rather chaotic signals observed in both A and C homopolymers may reflect stochastic motion of the polymerase on these templates. In contrast, the readily processed $d(ATC)_5$ yields regions of steady signal that might prove easier to interpret. The peak widths (FIGS. 18C and 18G) and the distribution of intervals between pulses (FIGS. 18D and 18H) show that there are some differences in the peak characteristics and peak frequencies between the two templates.

Figure 29:
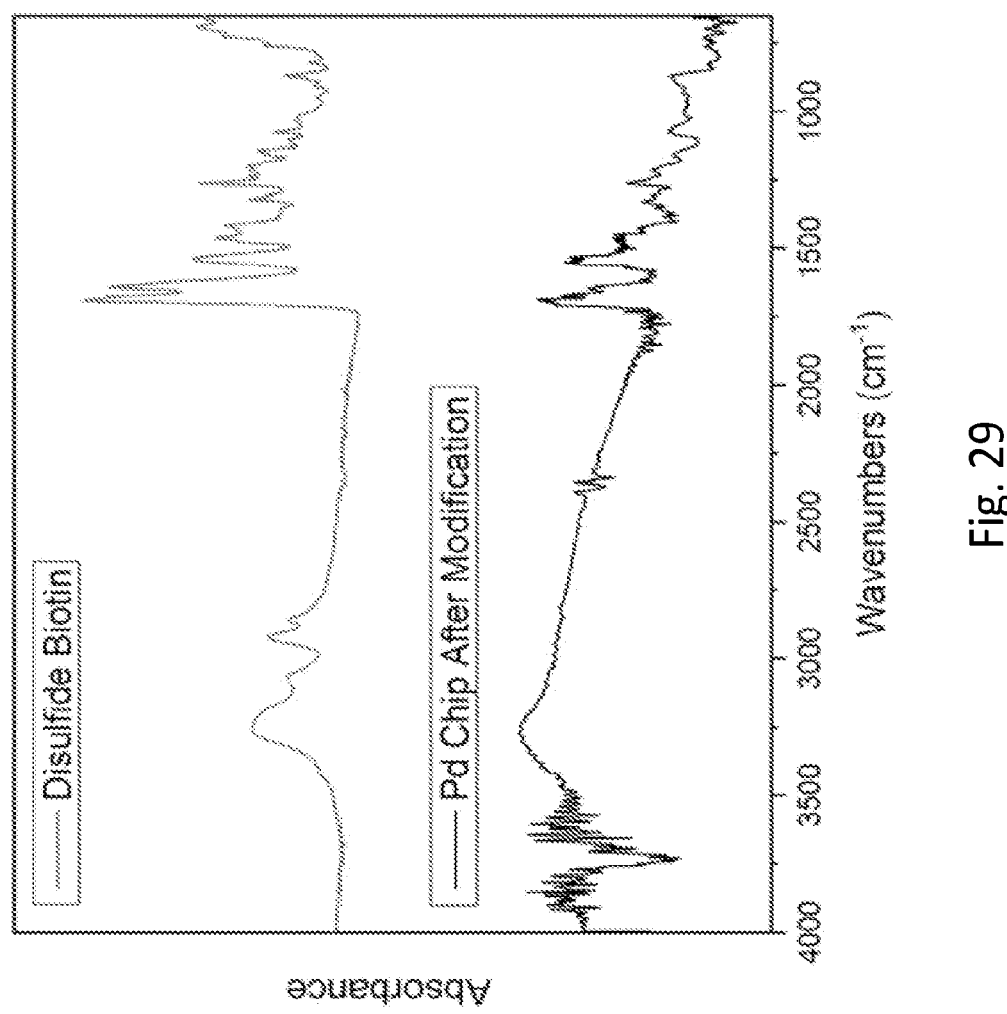
FIG. 29 shows Fourier Transform Infrared (FTIR) scans showing biotin functionalization of Pd.
Figures 30A, 30B, 30C, 30D:
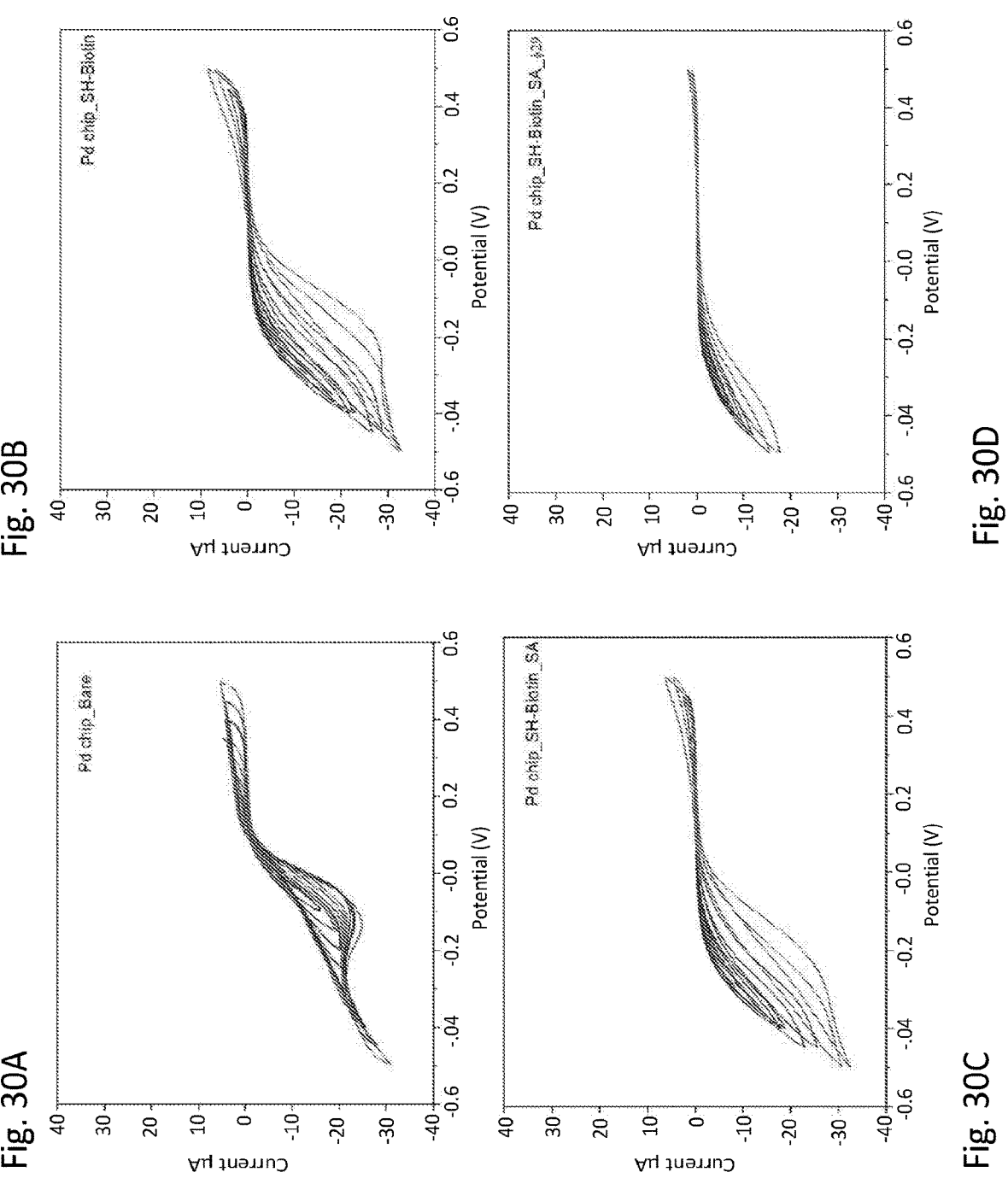
FIGS. 30A-30D shows CV scans of functionalized Pd. The range of operating potentials for the electrodes was determined by cyclic voltammetry.

Additionally, FIG. 29 shows Fourier Transform Infrared (FTIR) scans showing biotin functionalization of Pd. Further, FIGS. 30A-30D shows CV scans of functionalized Pd. The range of operating potentials for the electrodes was determined by cyclic voltammetry. Pd substrates were cut into 0.5 cm×4.0 cm in size and used as the working electrode, with an active cell area of about 0.5 cm×1.0 cm. The substrate was treated with a hydrogen flame before functionalization. Cyclic voltammetry was performed on a potentiostat (Model AFCBP1, Pine Instruments), using a Pt wire as the counter electrode and an Ag/AgCl (3M KCl) as the reference electrode. The maximum sweep range is from −0.5 V to +0.5 V, with a sweep rate of 10 mV/s, starting from ±0.05 V and increasing the scan range on 0.05V increments. (FIG. 30A) Bare Pd. (FIG. 30B)) Functionalized with SH-Biotin (50 μM, overnight). (FIG. 30C) With streptavidin added (1 μM, 0.5 h). (FIG. 30D) And after addition of Gen III Φ29 polymerase (1 μM, 2 hours). Two repeated sweeps are shown at the highest bias, showing some instability in the adsorbate.

Figures 31A, 31B, 31C, 31D:
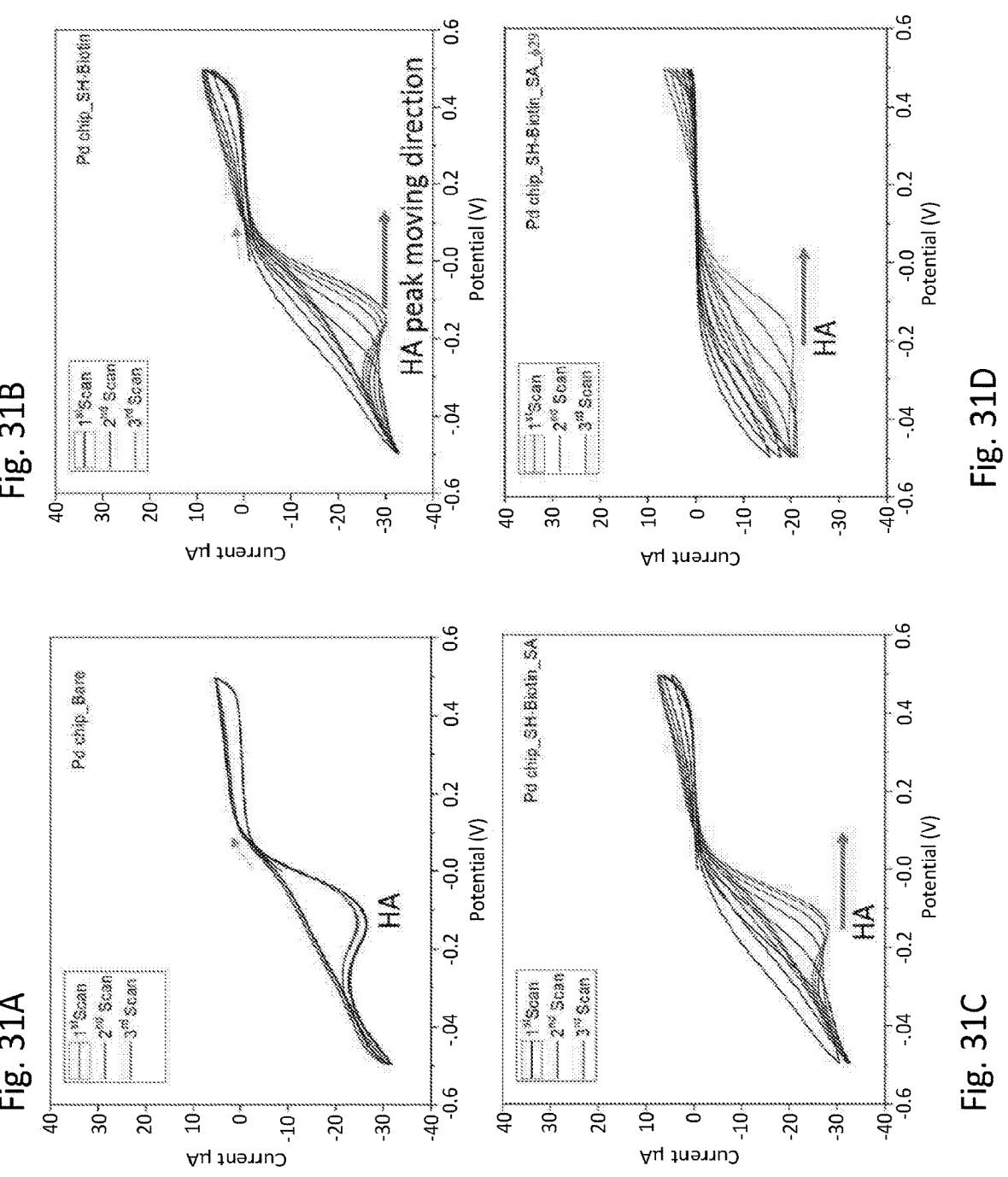
FIGS. 31A-31D show sweeps to negative potentials destabilize thiol-bound adsorbates illustrating how electrode potentials that destabilze thiol-bound adsorbate molecular films were determined.
Figures 32A, 32B, 32C, 32D:
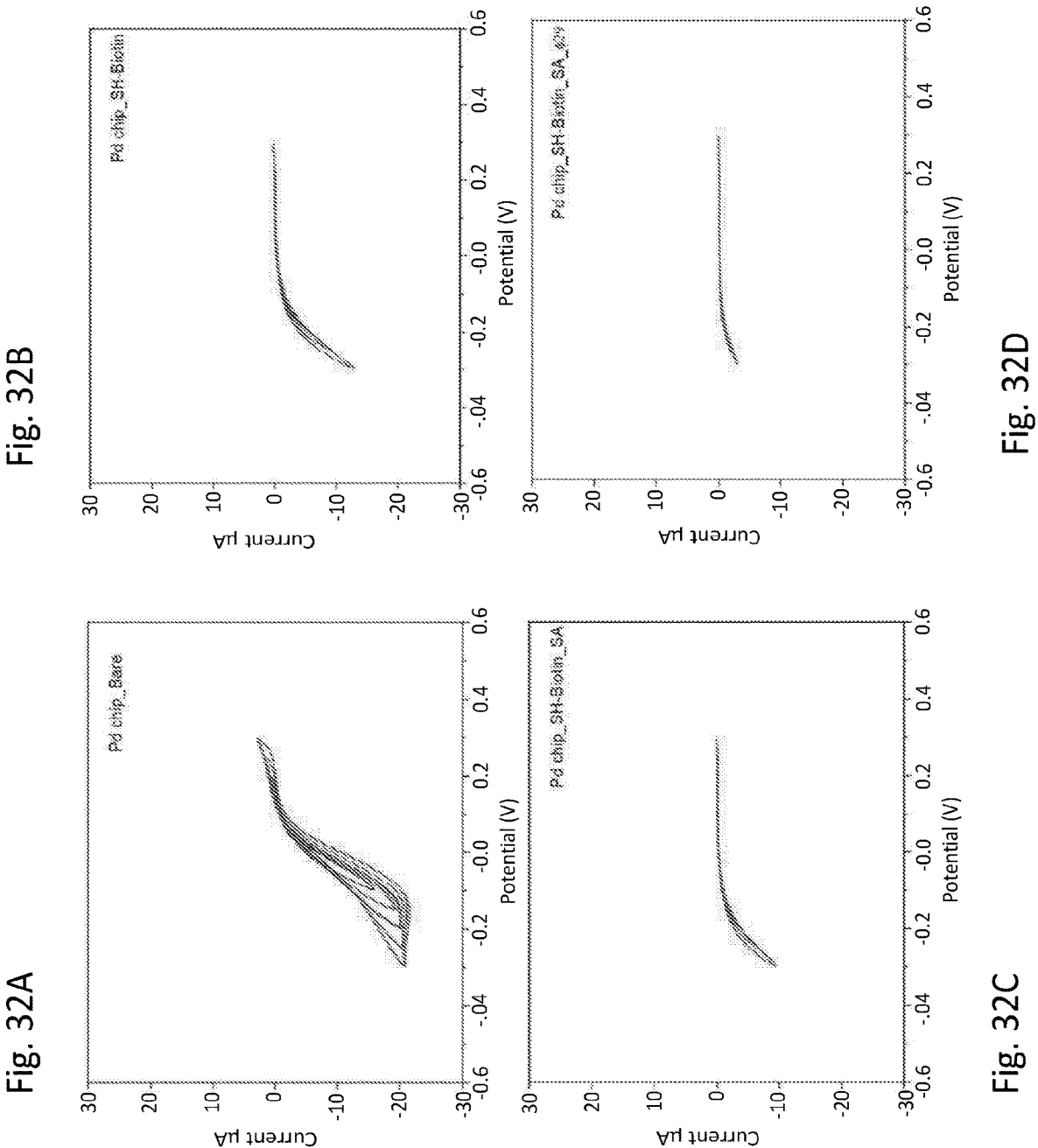
FIGS. 32A-32D show electrodes are passivated by biomolecular adsorbates in the potential range used for electronic measurements.

FIGS. 31A-31D show sweeps to negative potentials destabilize thiol-bound adsorbates illustrating how electrode potentials that destabilize thiol-bound adsorbate molecular films were determined. FIG. 31A shows repeated sweeps on bare Pd reproduce well (HA is the hydrogen adsorption peak). On functionalization with biotin (FIG. 31B), biotin plus streptavidin (FIG. 31C) and biotin plus streptavidin plus Φ29 polymerase (FIG. 31D), the HA peak, initially moved to more negative potentials relative to bare Pd, moves up towards the potential observed in bare Pd, consistent with stripping of the adsorbate by thiol reduction.

FIGS. 32A-32D show electrodes are passivated by biomolecular adsorbates in the potential range used for electronic measurements. In particular, FIGS. 32A-32D show how cyclic voltammetry was used to determine a range of potentials over which electrodes are passivated by biomolecular adsorbates. (FIG. 32A) Repeated sweeps on bare Pd. On functionalization with biotin (FIG. 32B), biotin plus streptavidin (FIG. 32C) and biotin plus streptavidin plus Φ29 polymerase (FIG. 32D) the electrode becomes increasingly passivated. These measurements illustrate that these electronically conductive films do not exchange charge with ions in solution.

CONCLUSIONS

Engineering two contact points into a polymerase yields features in the conductance distribution that are approximately 3 to 10 times larger than those observed with only one engineered contact and a second, non-specific, contact. The conductance of the complex of streptavidin and doubly biotinylated Φ29 is further increased if biotin is used to anchor the streptavidin to the electrodes in place of the usual anchoring by means of thiolating surface lysines. There are significant changes in the conductivity as polymerase Φ29 undergoes the open to closed transition and these changes can be detected dynamically as the occurrence of rapid noise spikes that have an amplitude of about 25% (or more) of the background current. There are similar, but much smaller, signals generated when the polymerase is not active. These small signals are also proportional to the background current (approximately 6%) and are present in both resting and active polymerase. This observation of a proportionality between the signal amplitude and the background current has implications for models of the mechanism of signal generation. Measurements of the electronic decay length in protein molecules show that the overall conductance has a large contribution from a small contact conductance, which limits the overall conductance significantly. The measurements of electronic decay length also show that the decay length is on the order of the protein size, so that it is impossible to distinguish between a slow exponential decay and a resistive model in which the decay of current scales with 1/(length). The two models predict different dependencies of the measured current on internal changes in the molecule. In a resistor model, where the contact resistance is $R_C$, the internal molecular resistance is R and the change associated with a conformational transition is $\delta R$, the fractional change in current on undergoing the transition is $(\delta i/i = \delta R/(R_C + R + \delta R))$. In a model based on transition probability, the current fluctuation is directly proportional to the change associated with the conformational transmission multiplied by the probability of charge injection, so again proportional to the baseline current. However, the resistive model implies a non-linear relationship between Oi and i because of the dependence of the slope on $R_C$.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

We claim:

1. A device for sequencing nucleic acids, comprising:

at least a first electrode and a second electrode, the first and second electrode are separated by a gap; and a polymerase comprising two attachment sites, a first attachment site for attachment of the polymerase to the first electrode and a second attachment site for attachment of the polymerase to the second electrode, wherein at least the first attachment site of the polymerase is specifically chemically modified for attachment to the first electrode;

wherein the two attachment sites are separated by a distance of at least about 1 nm and when the polymerase is attached to the first and second electrodes, the first attachment site and the second attachment site do not undergo movement relative to each other that exceeds 10% of their separation when the polymerase undergoes open-to-closed conformational changes, and wherein the two attachment sites of the polymerase are in an inactive region of the polymerase.

2. The device of claim 1, wherein one of the two attachment sites is located on an N-terminus of the polymerase.

3. The device of claim 1, wherein the polymerase is a DNA polymerase.

4. The device of claim 3, wherein the DNA polymerase is phi29 polymerase.

5. The device of claim 1, wherein the polymerase is an RNA polymerase.

6. The device of claim 5, wherein the RNA polymerase is a polio virus 3D RNA dependent RNA polymerase.

7. The device of claim 1, wherein the polymerase is modified to incorporate a ligand-binding site.

8. The device of claim 1, wherein the polymerase is a biotinylated polymerase.

9. The device of claim 8, wherein the biotinylated polymerase is attached to the first electrode and/or second electrode via streptavidin.

10. The device of claim 1, wherein the polymerase is modified to incorporate a non-canonical amino acid residue that allows for click-chemistry attachment of one or more other chemical groups to the first electrode and/or second electrode.

11. The device of claim 10, wherein the non-canonical amino acid is 4-Azido-L-phenylalanine.

12. The device of claim 1, wherein atomic coordinates for the first and second attachment points are the same to within 10% when the polymerase is in an open or closed conformation.

13. The device of claim 1, wherein the first electrode and second electrode comprise a metal selected from the group consisting of gold, platinum, palladium, and ruthenium or alloy thereof.

14. The device of claim 1, wherein the first electrode and second electrode are co-planar.

15. The device of claim 1, further comprising a dielectric substrate, wherein the first electrode is disposed on the dielectric substrate and an insulating dielectric layer disposed on the first electrode and the second electrode is disposed on the insulating dielectric layer; and a passivation layer disposed on the second electrode.

16. A system, comprising the device of claim 1 and a nucleic acid template.

17. The system of claim 16, wherein the nucleic acid template is a double stranded DNA template comprising at least one nick of more than one nucleotide.

18. The system of claim 17, wherein the at least one nick of more than one nucleotide is of nine or more nucleotides.

19. The system of claim 16, wherein the nucleic acid template is a circular DNA comprising a double stranded region.

20. The system of claim 16, wherein the nucleic acid template is a primed single-stranded RNA.

21. A method of determining the number of nucleic acids repeated in a nucleic acid template sequence comprising:

(a) introducing a solution comprising a nucleic acid template to the device of claim 1;

(b) measuring a first current generated when a bias is applied to the device;

(c) introducing a solution comprising a dNTP to the device under conditions that allow for incorporation of the dNTP complementary to the nucleic acid template;

(d) measuring a second current generated in step (c);

(e) removing the solution comprising the unincorporated dNTP;

(f) repeating steps (c) to (e);

(g) obtaining a signal stream from the current generated in step (b) and step (d), wherein the signal stream comprises at least one pause and at least one burst;

(h) identifying sections of current signal that fluctuate between two levels of current for an amount of time of greater than about 40 ms; and (i) determining that the nucleotide has been repeated in the nucleic acid template sequence if the signal stream comprises a pause that is about twice the length of a plurality of pauses in the signals stream.

22. A method of determining the identity of a nucleotide being incorporated into a nucleic acid template sequence, the method comprising:

(a) introducing a solution comprising a nucleic acid template to the device of claim 1;

(b) measuring a first current generated when a bias is applied to the device;

(c) introducing a solution comprising a dNTP to the device under conditions that allow for incorporation of the dNTP complementary to the nucleic acid template;

(d) measuring a second current generated in step (c);

(e) removing the solution comprising the unincorporated dNTP;

(f) repeating steps (c) to (e);

(g) obtaining a signal stream from the current generated in step (b) and step (d), wherein the signal stream comprises at least one pause and at least one burst;

(h) determining the identity of the incorporated nucleotide from the burst signal.

23. A method of sequencing a nucleic acid, comprising:

(a) introducing a solution comprising a nucleic acid template to device of claim 1, wherein the nucleic acid template comprises all possible 16 combinations of two sequential bases in the sequence;

(b) introducing a solution comprising a dNTP to the device under conditions that allow for incorporation of the dNTP complementary to the nucleic acid template;

(c) obtaining a signal stream from repeat sequences in the nucleic acid template, wherein the signal stream comprises at least one pause and at least one burst;

(d) using a signal analysis to characterize the burst signal of each incorporated dNTP; and (e) applying the signal analysis for sequencing a nucleic acid of unknown sequence.

24. The method of claim 21, wherein fluctuations that signal an active polymerase activity are those 25% or more of the background current whereas fluctuations up to 10% characterize an inactive polymerase.

25. The method of claim 21, wherein the nucleic acid template is a double stranded DNA template comprising at least one nick of more than one nucleotide.

26. The method of claim 25, wherein the at least one nick of more than one nucleotide is of nine or more nucleotides and the polymerase is phi29 DNA polymerase.

27. The method of claim 21, wherein the nucleic acid template is a circular DNA comprising a double stranded region.

28. The method of claim 21, wherein the nucleic acid template is a primed single-stranded RNA and the polymerase is an RNA polymerase, such as a polio virus 3D RNA dependent RNA polymerase.

29. The method of claim 28, wherein the primed single-stranded RNA is a hairpin primed single stranded RNA.

* * * * *